US011059939B2

(12) United States Patent
Lemcoff et al.

(10) Patent No.: US 11,059,939 B2
(45) Date of Patent: Jul. 13, 2021

(54) DICYCLOPENTADIENE DERIVATIVES AND POLYMERS THEREOF

(71) Applicant: B.G. Negev Technologies and Applications Ltd., at Ben-Gurion University, Beer-Sheva (IL)

(72) Inventors: N. Gabriel Lemcoff, Yakum (IL); Amos Ben Asuly, Kibbutz Beit Kama (IL); Yakov Ginzburg, Ramat-Gan (IL); Sukdeb Saha, West Bengal (IN)

(73) Assignee: B.G. Negev Technologies and Applications Ltd., at Ben-Gurion University, Beer-Sheva (IL)

( * ) Notice: Subject to any disclaimer, the term of this patent is extended or adjusted under 35 U.S.C. 154(b) by 36 days.

(21) Appl. No.: 15/769,398

(22) PCT Filed: Oct. 20, 2016

(86) PCT No.: PCT/IL2016/051139
§ 371 (c)(1),
(2) Date: Apr. 19, 2018

(87) PCT Pub. No.: WO2017/068588
PCT Pub. Date: Apr. 27, 2017

(65) Prior Publication Data
US 2019/0202976 A1 Jul. 4, 2019

Related U.S. Application Data

(60) Provisional application No. 62/244,297, filed on Oct. 21, 2015.

(51) Int. Cl.
*C08F 32/08* (2006.01)
*C07C 43/188* (2006.01)
(Continued)

(52) U.S. Cl.
CPC .............. *C08G 61/08* (2013.01); *C07C 43/18* (2013.01); *C07C 43/188* (2013.01);
(Continued)

(58) Field of Classification Search
None
See application file for complete search history.

(56) References Cited

U.S. PATENT DOCUMENTS

| 4,391,823 A | 7/1983 | Boxler et al. |
| 6,020,443 A | 2/2000 | Woodson et al. |

(Continued)

FOREIGN PATENT DOCUMENTS

| CN | 101845056 A | 9/2010 |
| JP | 3-98597 | 4/1991 |
| JP | 2003-055442 A | 2/2003 |

OTHER PUBLICATIONS

G. C. Vougioukalakis and R. H. Grubbs. "Ruthenium-Based Heterocyclic Carbene-Coordinated Olefin Metathesis Catalysts". Chem. Rev. 2010, 110(3), 1746-1787. (Year: 2010).*

(Continued)

*Primary Examiner* — Richard A Hunh

(74) *Attorney, Agent, or Firm* — Marshall, Gerstein & Borun LLP

(57) ABSTRACT

Dicyclopentadiene (DCPD) derivatives of following general formula (I); their preparation and use thereof, especially as monomers in polymerization reactions, such as olefin polymerization or ring-opening metathesis polymerization (ROMP).

(Continued)

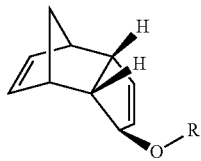

(I)

12 Claims, 78 Drawing Sheets

(51) Int. Cl.
| | |
|---|---|
| *C08G 61/08* | (2006.01) |
| *C07C 69/013* | (2006.01) |
| *C07D 233/60* | (2006.01) |
| *C07C 43/18* | (2006.01) |
| *C08F 2/60* | (2006.01) |
| *C08F 4/40* | (2006.01) |
| *C08F 2/10* | (2006.01) |

(52) U.S. Cl.
CPC .......... *C07C 69/013* (2013.01); *C07D 233/60* (2013.01); *C08F 32/08* (2013.01); C07C 2603/68 (2017.05); C08F 2/10 (2013.01); C08F 2/60 (2013.01); C08F 4/40 (2013.01); C08G 2261/135 (2013.01); C08G 2261/143 (2013.01); C08G 2261/1422 (2013.01); C08G 2261/1424 (2013.01); C08G 2261/1426 (2013.01); C08G 2261/3325 (2013.01); C08G 2261/418 (2013.01); C08G 2261/74 (2013.01); C08G 2261/76 (2013.01)

(56) References Cited

U.S. PATENT DOCUMENTS

| | | |
|---|---|---|
| 9,082,981 B1 | 7/2015 | Lu et al. |
| 2014/0087136 A1 | 3/2014 | Osaku |
| 2014/0155511 A1 | 6/2014 | Lemcoff et al. |

OTHER PUBLICATIONS

Shao et al., "C₁-Symmetric Dicyclopentadienes as New Chiral Diene Ligands for Asymmetric Rhodium-Catalyzed Arylation of N-Tosylarylimines", Organic Letters, vol. 12, No. 17, 2010, pp. 3820-3823.

Iranpoor et al., "Cerium ((V), as a Selective and Efficient Catalyst for Alcoholyses of Allylic and Tertiary Benzylic Alcohols", Tetrahedron, vol. 50, No. 6, 1994, pp. 1859-1870.

Shao et al., Easily Accessible Chiral Dicyclopentadiene Ligands for Rhodium-catalyzed Enantioselective 1,4-addition Reactions, Tetrahedron Letters vol. 53, No. 22, 2012, pp. 2733-2735.

Gong et al., ROMP of Acetoxy-substituted Dicyclopentadiene to a Linear Polymer with a High $T_G$, RSC Advances, vol. 5, No. 33, 2015, pp. 26185-26188.

Extended European Search Report in EP Application No. 16857049.7 dated Jun. 13, 2019, 9 pages.

Ito et al., "Optical Resolution of 3a,4,7,7a-Tetrahydro-4,7-methano-1 H-indene Derivatives", Bull. Chem. Soc. Japan, vol. 58 (12), Dec. 1985, pp. 3631-3632.

Gong et al., "ROMP of acetoxy-substituted dicyclopentadiene to a Linear Polymer with a High $T_g$", RSC Advances, vol. 5(33), Mar. 20, 2015, pp. 26185-26188.

Sutthasupa et al., "Recent Advances in Ring-Opening Metathesis Polymerization, and Application to Synthesis of Functional Materials", Polymer Journal, vol. 42, Oct. 13, 2010, pp. 905-915.

Vidaysky et al., "Light-induced Olefin Metathesis", Beilstein J. Org. Chem., 6, Nov. 23, 2010, pp. 1106-1119.

Gharpure et al., "Topologically Driven Tandem Radical Cyclization-based Strategy for the Synthesis of oxa- and aza-cages", Tetrahedron Letters 50, 2009, pp. 7162-7165.

Kotha et al, "Synthesis of a Tricyclic Lactam via Beckmann Rearrangement and Ring-rearrangement Metathesis as Key Steps", Beilstein Journal of Organic Chemistry, 11, 2015, pp. 1503-1508.

Kotha et al, "Diversity-Oriented Approach to Carbocycles and Heterocycles Through Ring-rearrangement Metathesis, Fischer Indole Cyclization, and Diels-Alder Reaction as Key Steps," Eur. J. Org. Chem, 2014, pp. 5582-5590.

Kotha et al., "Design and Synthesis of Oxa-bowls via Diels-Alder Reaction and Ring-rearrangement Metathesis as Key Steps", Tetrahedron Letters 55, 2014, pp. 5781-5784.

Amoore et al., "Odor as an Aid to Chemical Safety: Odor Thresholds Compared With Threshold Limit Values and Volatilities for 214 Industrial Chemicals in Air and Water Dilution", Journal of Applied Toxicology, vol. 3, No. 6, 1983, pp. 272-290.

Elmer et al., "Exploring the Reversibility of the Ring-Closing Metathesis Mediated Cross-linking of Dendrimers", Macromolecules, 40, 2007, pp. 8114-8118.

Diesendruck et al., "A Latent S-Chelated Ruthenium Benzylidene Initiator for Ring-Opening Metathesis Polymerization", J. Polym. Sci. Part A: Polym. Chem 47, 2009, pp. 4209-4213.

Tzur et al., "Latent Ruthenium Catalysts for Ring Opening Metathesis Polymerization (ROMP)", Handbook of Metathesis vol. 3: Polymer Synthesis, Second Edition, 2015, pp. 283-312.

Ginzburg et al., "Hoveyda-Type Olefin Metathesis Complexes", Olefin Metathesis: Theory and Practice, First Edition, 2014, pp. 437-451.

Search Report and Written Opinion in International Application No. PCT/IL2016/051139 dated Feb. 15, 2017, 8 pages.

\* cited by examiner

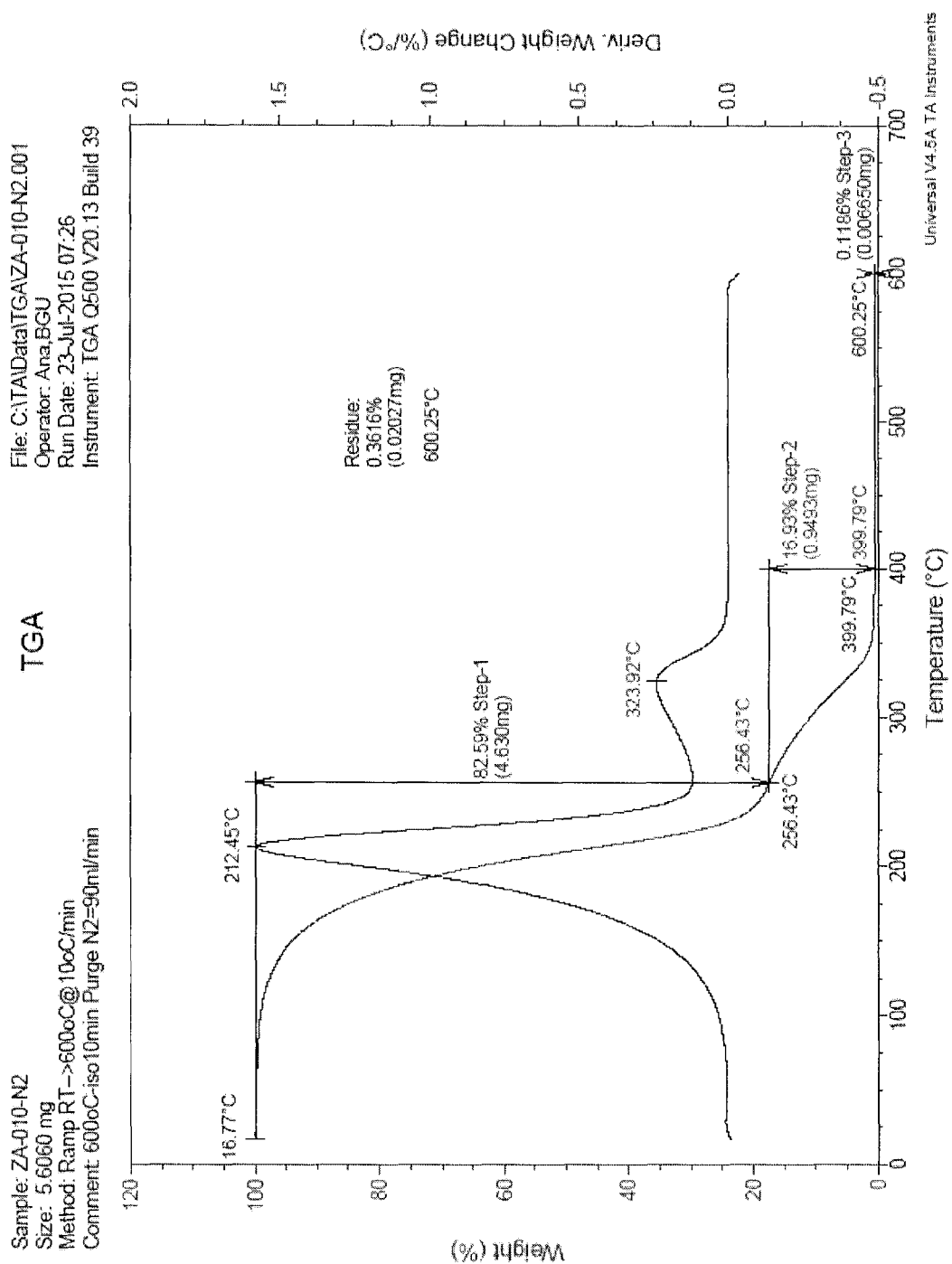

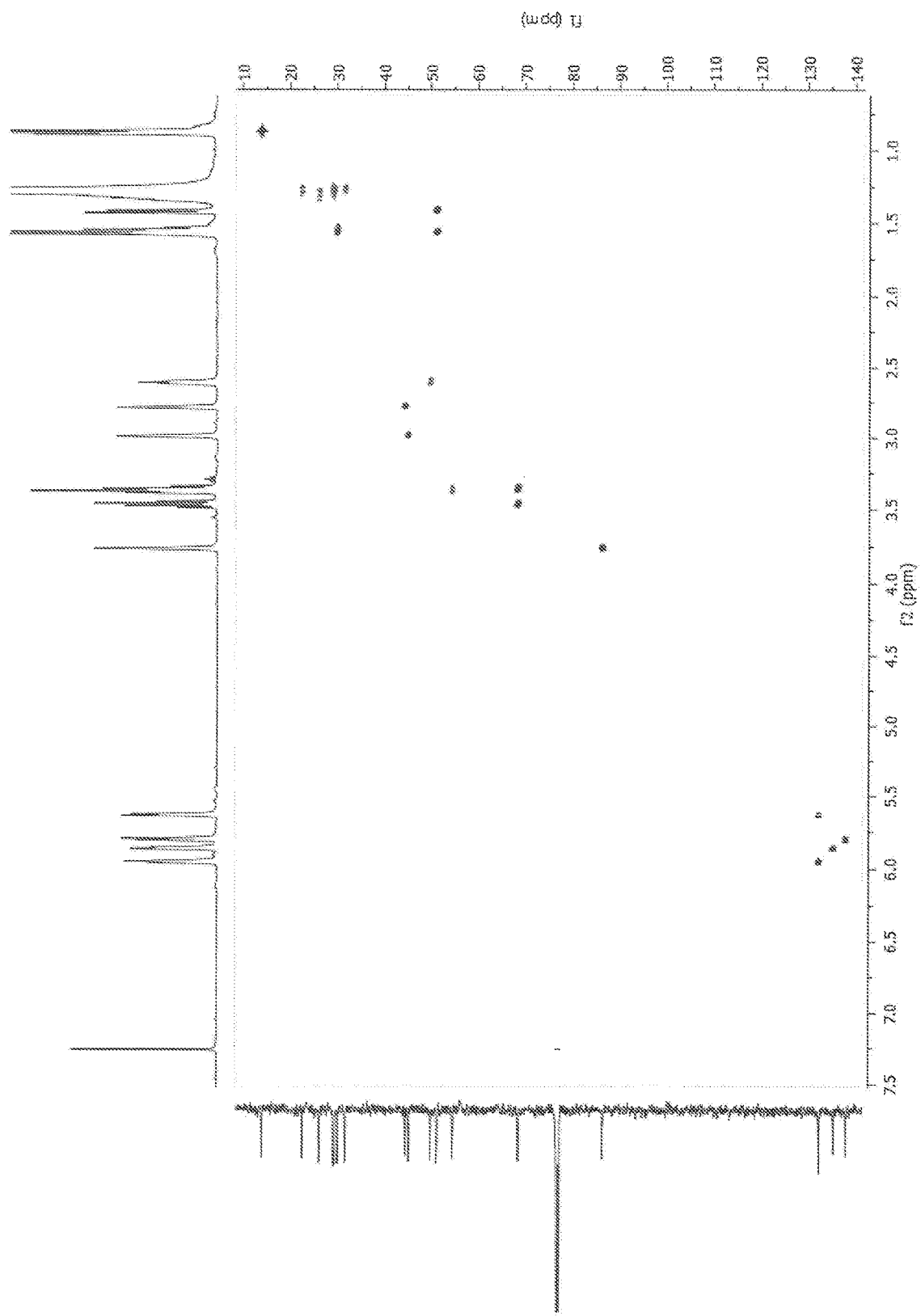

p-DCPD-OH - 37°    copolymer - 44°    p-DCPD-OOPr - 61°

DICYCLOPENTADIENE DERIVATIVES AND POLYMERS THEREOF

The invention relates to dicyclopentadiene (DCPD) derivatives, their preparation and use thereof, especially as monomers in polymerization reactions.

DCPD derivatives can be used as monomers in polymerization reactions, either in olefin polymerization or in ring-opening metathesis polymerization (ROMP). For example, with the aid of olefin polymerization catalysts, copolymers can be formed with ethylene or styrene by polymerizing only the norbornene double bond. Using ring-opening metathesis polymerization, the homopolymer is formed.

DCPD derivatives can be used to produce a wide range of resins, including aromatic hydrocarbon resins, unsaturated polyester resins, phenolics and epoxies.

Gharpure and Porwal (Tetrahedron Letters. Volume 50, Issue 51, 23 Dec. 2009, Pages 7162-7165) disclose the propargylic ether of DCPD. Kotha S. et al. (Beilstein J. Org. Chem. 2015, 11, 1503-1508) disclose the ketone derivative of DCPD and two stereoisomeric oximes prepared therefrom. Kotha S. and Ravikumar O. (Eur. J. Org. Chem. 2014, 5582-5590 and Tetrahedron Letters 55 (2014) 5781-5784) disclose several enone, 0-allyl and N-allyl derivatives of DCPD. Gong L. et al. (RSC Adv., 2015, 5, 26185-26188) disclose the acetoxy derivative of DCPD and linear polymer thereof.

Notwithstanding the desirable properties of the polymer of DCPD (pDCPD), the use of DCPD as a ring opening metathesis polymerization (ROMP) monomer is currently limited due to the irritating odour of the monomer, detectable even at 5 ppb levels (J. E. Amoore and E. Hautala, J. Appl. Toxicol., 1983, 3, 272-290) and thus requiring special handling. It has now been found that certain DCPD derivatives are free of the irritating odor and thus possess an important advantage from the environmental, health, safety and industrial handling aspects. In addition, the DCPD derivatives display polymerization behavior similar to the parent DCPD monomer. The polymers obtained thus possess greatly improved physical properties when compared to many of the acrylate and styrene derived polymers.

According to one aspect of the invention there is provided DCPD derivative of general formula (I):

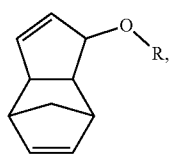

Formula (I)

specifically, endo-DCPD derivative, e.g.:

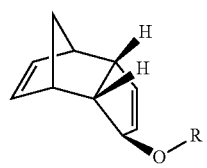

wherein:
R is selected from the group consisting of a linear alkyl ($C_nH_{2n+1}$), branched alkyl ($C_nH_{2n+1}$), a substituted or unsubstituted aryl, a substituted or unsubstituted alkylaryl, a positively charged nitrogen-containing group (in which case the compound of Formula (I) is provided in a form of a salt with a suitable counter-ion), DCPD-O-Me- and ester-forming group of a general formula —C(O)—R', wherein R' is an organic moiety.

As a general remark, monomers described herein are obtained as racemic mixtures. The formula (general Formula (I)) depicted above and other formulae shown below, illustrating endo-DCPD derivatives, are intended to indicate a racemic mixture (and individual stereoisomers/enantiomers).

In some preferred embodiments of the DCPD derivative of general formula (I), R is linear or branched alkyl. The linear alkyl is a chain consisting of 1-20 carbon atoms, e.g. C1 to C8 alkyls are preferred. Preferably, the linear alkyl is selected from the group consisting of methyl, ethyl, n-propyl or n-octyl (compounds of Formulae 1-4).

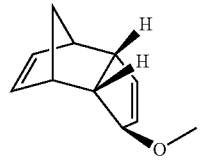

Formula 1

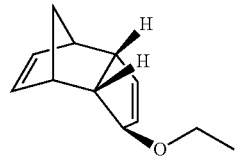

Formula 2

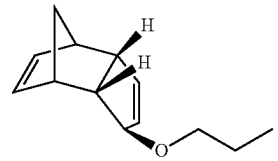

Formula 3

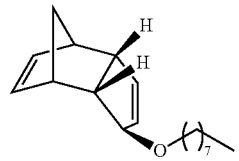

Formula 4

In some preferred embodiments of the DCPD derivative of general Formula (I), R is an aryl. The aryl comprises at least one aromatic ring and may be connected to the DCPD moiety via an alkylene linker (e.g. compound of Formula 5). The aryl may be optionally substituted with one or more of alkyl, halogen, nitro and carbonyl chloride group.

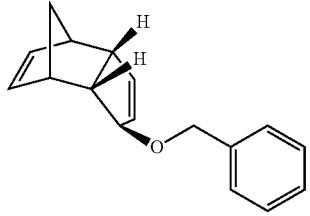

Formula 5

In some preferred embodiments of the DCPD derivative of general Formula (I), R is a positively charged nitrogen-containing group, wherein the positively charged nitrogen may form part of a ring system. In such embodiments, the compound of general Formula (I) is provided in a form of a salt with a suitable counter-ion $Y^-$.

The counter-ion $Y^-$ is provided by any suitable anion. The anion may be a halide, e.g. bromide or iodide, hexafluorophosphate or tetrafluoroborate.

In some preferred embodiments, the positively charged nitrogen-containing group is part of a ring system, e.g. imidazole. Preferably, the positively charged nitrogen of the imidazole ring is connected to the oxygen atom in Formula (I) via a bridging moiety, which is preferably alkylene, such as $-(CH_2)_n-$, wherein n is an integer from 2 to 10; most preferably the alkylene bridge is linear C5, C6 or C7 alkylene. Preferably the imidazole ring may be substituted at one or more of positions 1, 2, 4 and 5, wherein the substituent is preferably an alkyl group; most preferably the imidazole ring is substituted at one or both of positions 1 and 2. The substituent is preferably a methyl group.

In some variants, R is a quaternary ammonium having the formula $[-R^1-N^+R^2R^3R^4Y^-]$. Bridging $R^1$ is a moiety that preferably contains an alkylene chain, and $R^2$, $R^3$ and $R^4$ are preferably independently selected from the group consisting of an alkyl group and an aryl ring.

According to some preferred embodiments of the DCPD derivative of general formula (I), R is selected from the group consisting of 3-pentylene-1-methyl-imidazolium bromide, 3-hexylene-1-methyl-imidazolium bromide, 3-heptylene-1-methyl-imidazolium bromide and 3-pentylene-1,2-dimethyl-imidazolium bromide (compounds of Formulae 6-9).

Formula 6

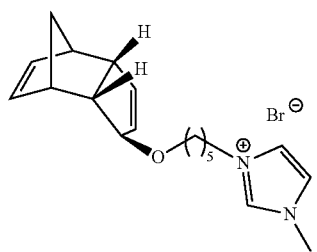

Formula 7

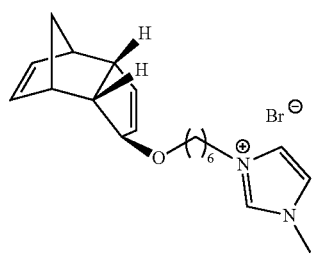

Formula 8

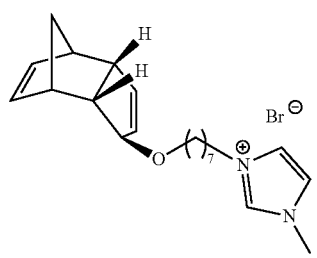

Formula 9

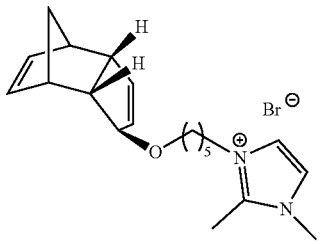

According to one preferred embodiment of the DCPD derivative of general formula (I), R is DCPD-O-Me— (compound of Formula 10).

Formula 10

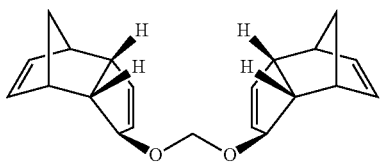

In some preferred embodiments of the DCPD derivative of general Formula (I), R is ester-forming group of a general formula $-C(O)-R'$. Such ester derivatives of DCPD form another aspect of the invention. Thus, according to this aspect of the invention there is provided a DCPD derivative (specifically, endo-DCPD derivative) of general Formula (II):

Formula (II)

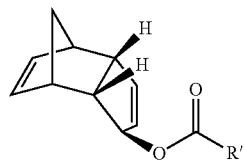

wherein:
R' is an organic moiety which is preferably selected from the group consisting of a linear or branched alkyl ($C_nH_{2n+1}$), substituted or unsubstituted aryl, e.g. phenyl, and a positively charged nitrogen-containing group (in which case the compound of Formula (II) is provided in a form of a salt with a suitable counter-ion). The linear alkyl is a chain consisting of 1-20 carbon atoms, e.g. C2 or C4 alkyls are preferred. R' is not methyl.

According to some preferred embodiments of the DCPD derivative of general Formula (II), R' is an unsubstituted phenyl (compound of Formula 11).

Forumla 11

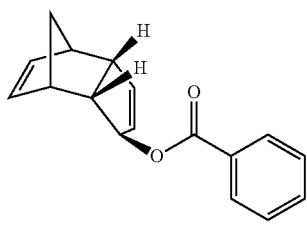

According to some preferred embodiments of the DCPD derivative of general Formula (II), R' is a substituted phenyl, preferably substituted with one or more of alkyl, halogen, nitro and carbonyl chloride group.

According to some preferred embodiments of the DCPD derivative of general Formula (II), R' is the positively charged nitrogen-containing group, as defined above, and the compound of Formula (II) is provided in a form of a salt with a suitable counter-ion Y. In some variants, R' is a quaternary ammonium having a formula [—R$^5$—N$^+$R$^6$R$^7$R$^8$Y$^-$]. Bridging R$^5$ is a moiety that preferably contains an alkylene group such as —(CH$_2$)$_n$—, wherein n is preferably an integer from 2 to 10; or a phenylene group [—(C$_6$H$_4$)—], and R$^6$, R$^7$ and R$^8$ are preferably independently selected from the group consisting of an alkyl group and an aryl ring. In certain preferred embodiments of such DCPD derivatives of general Formula (II), R$^5$ is phenylene, each of R$^6$, R$^7$ and R$^8$ is methyl and Y$^-$ is halogen, preferably I$^-$, or hexafluorophosphate (compounds of Formulae 12 and 13).

Formula 12

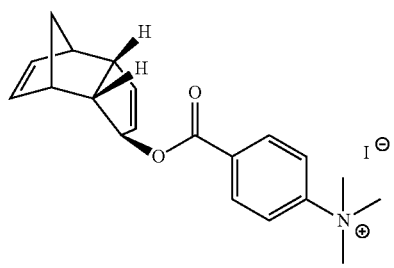

Formula 13

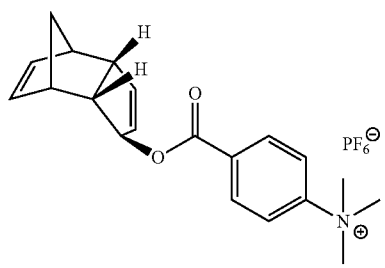

According to another aspect of the invention, provided herein is a process for the preparation of DCPD derivative of Formula (I) starting from hydroxydicyclopentadiene (DCPD-OH) (specifically, endo-hydroxydicyclopentadiene).

For example, regarding the synthesis of DCPD derivatives of general Formula (I) wherein R is an alkyl, these compounds can be prepared by reacting hydroxydicyclopentadiene (DCPD-OH) with a corresponding haloalkane compound. For example, compounds of Formulae 1, 3 and 4 were prepared according to the reaction scheme shown below:

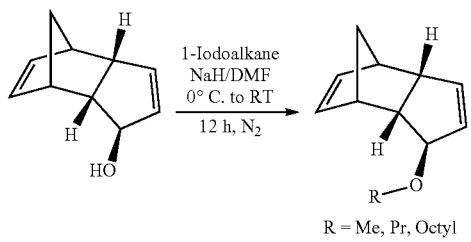

R = Me, Pr, Octyl

Thus, provided herein is a process for the preparation of DCPD derivative of Formula (I) wherein R is an alkyl, comprising combining hydroxy-DCPD in the presence of a base, with a haloalkane of the formula R-Hal, in a suitable solvent, and isolating of the DCPD derivative.

In a specific embodiment provided herein is a process for the preparation of DCPD derivative of Formula (I) wherein R is an alkyl, comprising:

a) dissolving hydroxydicyclopentadiene in a suitable solvent in the presence of a base to form a solution;

b) adding a haloalkane R-Hal to the solution of hydroxydicyclopentadiene to form a reaction mixture;

c) stirring the reaction mixture, preferably at room temperature, preferably under inert atmosphere, to form the neutral DCPD derivative of Formula (I);

d) isolating the neutral DCPD derivative of Formula (I) from the reaction mixture.

Turning now to an exemplary synthesis of the DCPD salts of general Formula (I), bearing the positively-charged nitrogen-containing group and a counter-ion, these salts can be prepared by reacting a compound of Formula (III)

Formula (III)

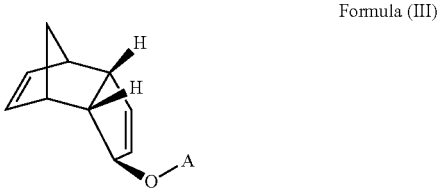

wherein A is —(CH$_2$)$_n$-Hal, wherein n is an integer from 2 to 10 and Hal is halogen, with a tertiary amine. The tertiary amine may be a nitrogen(s)-containing ring, e.g. imidazole, or is an NR$^2$R$^3$R$^4$, wherein R$^2$, R$^3$, and R$^4$ are defined as above. The anion of the salt may be readily exchanged. The compounds of Formula (III) can be prepared by a process comprising combining hydroxy-DCPD (DCPD-OH) in presence of a base, with a dihaloalkane of a formula Hal$^1$-(CH$_2$)$_n$-Hal$^2$, wherein Hal$^1$ and Hal$^2$ may be the same or different, in a suitable solvent, and optionally isolating of the O-haloalkyl-DCPD derivative.

Thus, for example, compounds of Formulae 6, 7 and 8 were prepared according to the reaction scheme shown below:

Step 1

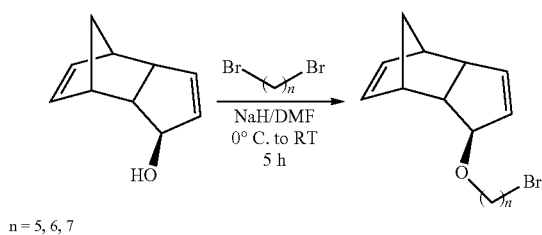

n = 5, 6, 7

Step 2

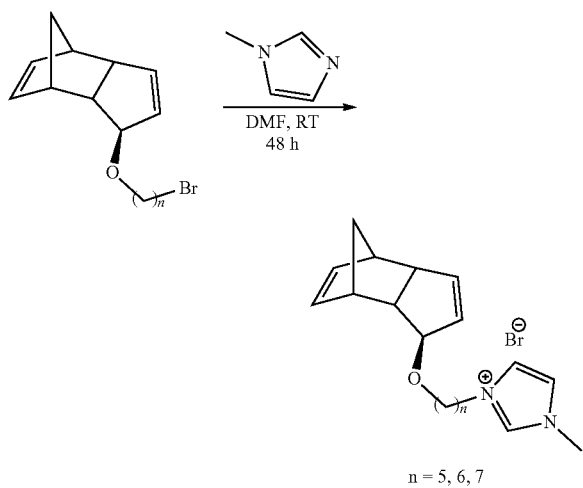

n = 5, 6, 7

For preparation of compound of Formula 9, Step 2 was carried out with 1,2-dimethylimidazole (instead of N-methyl imidazole).

In a specific embodiment, provided herein is a process for the preparation of quaternary imidazolium DCPD derivative of Formula (I), comprising:
a) dissolving hydroxydicyclopentadiene in a suitable solvent in the presence of a base to form a solution;
b) adding a dihaloalkane $Hal^1$-$(CH_2)_n$—$Hal^2$, wherein $Hal^1$ and $Hal^2$ may be same or different, and wherein n is 5, 6, or 7, to the solution of hydroxydicyclopentadiene to form a reaction mixture;
c) stirring the reaction mixture, preferably at room temperature, preferably under inert atmosphere, to form an O-haloalkoxy DCPD derivative of Formula (IIIa);

Formula (IIIa)

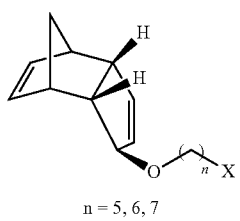

n = 5, 6, 7

(where X is halogen)
d) isolating the O-haloalkoxy DCPD of Formula (IIIa) from the reaction mixture;
e) dissolving the O-haloalkoxy DCPD of Formula (IIIa) in a solvent to form a solution;
f) adding an imidazole compound to the solution of O-haloalkoxy DCPD of Formula (IIIa) to form a reaction mixture;
g) stirring the reaction mixture, preferably at room temperature, preferably under inert atmosphere, to form the imidazolium DCPD derivative salt of Formula (I);
h) isolating the imidazolium DCPD derivative salt of Formula (I) from the reaction mixture.

Alternatively, the reaction is a one-pot reaction.

As for the compound of Formula 10, it was prepared according to the reaction scheme shown below:

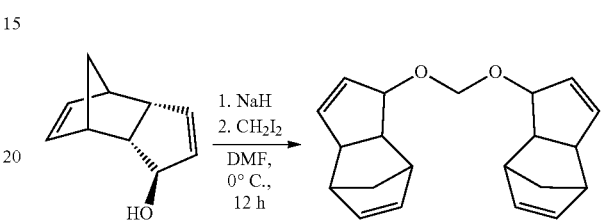

Turning now to the synthesis of the compounds of general Formula (II), these compounds can be prepared by reacting hydroxydicyclopentadiene (DCPD-OH) with an appropriate acyl halide, of a formula R"—C(O)-Hal, wherein R" is preferably selected from the group consisting of a C2, C3 or C4 linear alkyl; substituted or unsubstituted aryl, e.g. phenyl; and a tertiary amine group, e.g. an —$R^5$—$NR^6R^7$, wherein $R^5$, $R^6$, and $R^7$ are defined as above; and Hal is a halogen, preferably a chloride, in the presence of a base. In the case when R" is —$R^5$—$NR^6R^7$, the resultant intermediate is further reacted with a haloalkane $R^8$-Hal wherein $R^8$ is defined above, to quarternize the amine, i.e. to obtain the salts of Formula (II) with R' being a positively charged nitrogen-containing group. The acyl halide derivatives are usually readily obtained from the corresponding acids R"—COOH that are readily available starting materials.

In a specific embodiment the process for the preparation of DCPD derivative of Formula (II), comprises:
a) dissolving hydroxydicyclopentadiene in a suitable solvent in the presence of a base, to form a solution;
b) adding an acyl chloride compound R"—C(O)—Cl, wherein R" is an alkyl or aryl, to the solution of hydroxydicyclopentadiene to form a reaction mixture;
c) stirring the reaction mixture, preferably at a temperature from 0° C. to room temperature, preferably under inert atmosphere, to form a DCPD derivative of Formula (II);
d) isolating the DCPD derivative of Formula (II) from the reaction mixture.

More specifically, the synthesis of the salts of Formula (II), can be carried out by first converting an aminocarboxylic acid, e.g. N,N-dimethylamino benzoic acid, to the respective chloride, e.g. N,N-dimethylamino benzoyl chloride; reacting the acyl chloride R"—C(O)—Cl, wherein R" is —$R^5$—$NR^6R^7$, e.g. N,N-dimethylamino benzoyl chloride, with hydroxydicyclopentadiene e.g. in presence of a base, e.g. triethyl amine, as described above, to yield the tertiary amine DCPD derivative intermediate, e.g. N,N-dimethylamino benzoyl derivative of DCPD; and reacting the tertiary amine, e.g. N,N-dimethylamino benzoyl derivative of DCPD, with a suitable haloalkane $R^8$-Hal, in a solvent, such as DMF.

Thus, for example, compound of Formula 12 was prepared according to the reaction scheme shown below:

Step 1:

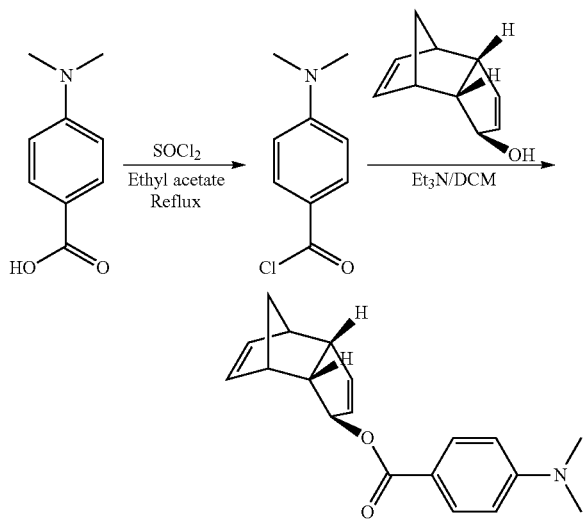

Step 2

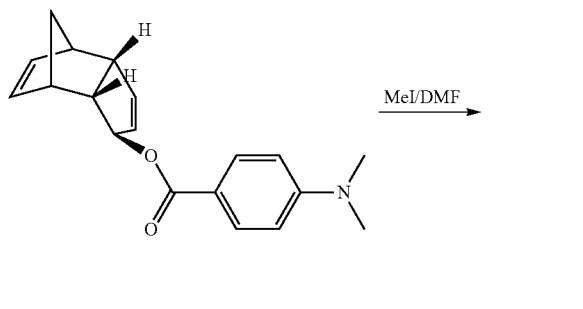

The counter-ion may be exchanged by conventional reactions, for example the compound of Formula 13 was prepared by reacting an aqueous solution of compound of Formula 12 with NH₄PF₆ according to the reaction scheme shown below:

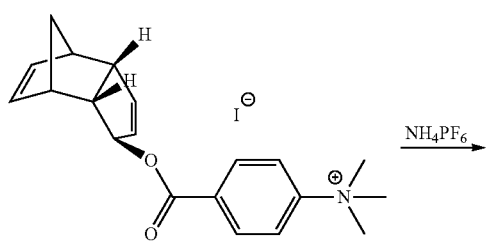

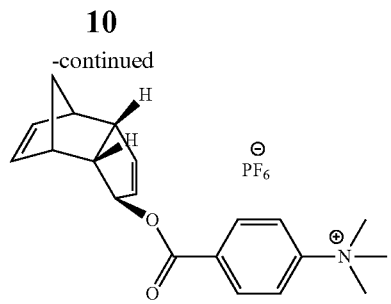

In a specific embodiment, provided herein is a process for the preparation of quaternary ammonium DCPD derivative of Formula (II), comprising:

a) dissolving hydroxydicyclopentadiene in a suitable solvent in the presence of a base, to form a solution;

b) adding the solution of hydroxydicyclopentadiene to a solution of N,N-dialkylaminobenzoyl chloride to form a reaction mixture;

c) stirring the reaction mixture, preferably at room temperature, preferably under inert atmosphere, to form a N,N-dialkylaminobenzoyl DCPD of Formula (IV), wherein both of $R^6$ and $R^7$ are methyl;

Formula (IV)

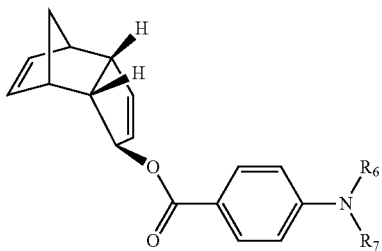

d) isolating the DCPD ester of Formula (IV) from the reaction mixture;

e) dissolving the DCPD ester of Formula (IV) in a solvent to form a solution;

f) adding a haloalkane to the solution of the DCPD ester of Formula (IV) to form a reaction mixture;

g) stirring the reaction mixture, preferably at room temperature, preferably under inert atmosphere, to form the quaternary ammonium DCPD derivative of Formula (II);

h) isolating the quaternary ammonium DCPD derivative of Formula (II) from the reaction mixture; and optionally i) exchanging the counter-ion.

The synthesis of the DCPD derivatives of Formulae (I) and (II) takes place in a solvent. Suitable solvents for synthesis of DCPD derivatives of Formula (I) include polar aprotic solvents, such as tetrahydrofuran (THF), diethyl ether, dioxane and dimethylformamide (DMF). Suitable solvents for synthesis of DCPD derivatives of Formula (II) include polar aprotic poor nucleophiles, such as dichloromethane (DCM), tetrahydrofuran (THF), diethyl ether and dioxane.

In preparation of DCPD derivatives of Formulae (I) and (II), hydroxydicyclopentadiene is combined together with the solvent/solvent mixture in a reaction vessel at a suitable molar ratio, for example, of about 1:1.2 to 1:1.5, inclusive, with a suitable reactant (such as for example, without being limited to, a haloalkane, a dihaloalkane) added to the solution. The so-formed solution is kept under stirring, preferably at a room temperature or on ice (e.g. at 0° C.), preferably for not less than 12 hours. The stirring is preferably conducted under inert atmosphere.

On completion of the reaction, the product, i.e., the DCPD derivative of Formula (I) or (II), is isolated in a liquid or solid form (depending on the properties of the DCPD derivative at room temperature) using conventional techniques. For example, neutral DCPD derivatives, such as for example compounds of Formulae 1-5, which are liquids at room temperature, were isolated by separating the organic layer, in which DCPD derivative is present, from the reaction mixture, followed by drying, concentrating and subjecting to flash column chromatography for purification. For example, ionic DCPD derivatives, such as for example compounds of Formulae 6-9, 12 and 13, which are gels or solids at room temperature, were obtained by removing the solvent from the reaction mixture, followed by adding of an antisolvent, such as diethyl ether, to allow the gelation or the precipitation of the product.

The compounds of Formula (I) and (II) can be prepared by reacting hydroxydicyclopentadiene (DCPD-OH) as explained in detail above. The starting material in the aforementioned reactions, namely, hydroxydicyclopentadiene, can be prepared, for example, from endo-dicyclopentadiene.

Thus, for example, hydroxydicyclopentadiene (DCPD-OH) was prepared from endo-dicyclopentadiene according to the reaction scheme shown below:

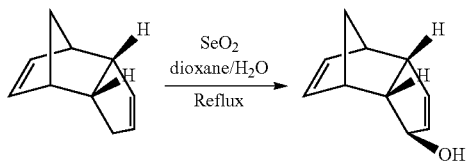 [SMILES: C1=C[C@H]2C3C=CC(C3)[C@H]2C1 ; O[C@@H]1C=C[C@H]2C3C=CC(C3)[C@@H]12]

DCPD derivatives of general formula (I) or (II) are highly reactive intermediates that can be used, for example, in the manufacturing of a wide range of resins and polymers, i.e. aromatic hydrocarbons, unsaturated polyesters, phenolics and epoxies. Such uses form additional aspects of the invention.

Thus, the invention also relates to a process for polymerizing a monomer of Formulae (I) or (II). In a preferred embodiment the process comprises mixing the monomer of Formula (I) or (II) with a catalyst, optionally in a solvent, and optionally activating the catalyst. Preferably the catalyst is a ruthenium based catalyst.

In some preferred embodiments of a process for polymerizing a monomer of Formulae (I) or (II), the polymer is formed by a ring-opening metathesis polymerization (ROMP) reaction.

Some DCPD derivatives of general Formula (I) or (II) were polymerized according to the ring opening metathesis polymerization (ROMP) reaction scheme shown below (the reaction took place under heating, e.g. at 70° C., either with Grubbs' $2^{nd}$ generation catalyst (e.g. (1,3-bis(2,4,6-trimethylphenyl)-2-imidazolidinylidene)dichloro (phenylmethylene)(tricyclohexylphosphine)ruthenium), commercially available from Sigma Aldrich) or with sulfur-chelated ruthenium complex, as described in Ginzburg, Y. et al. Organometallics, 2011, 30, 3430-3437):

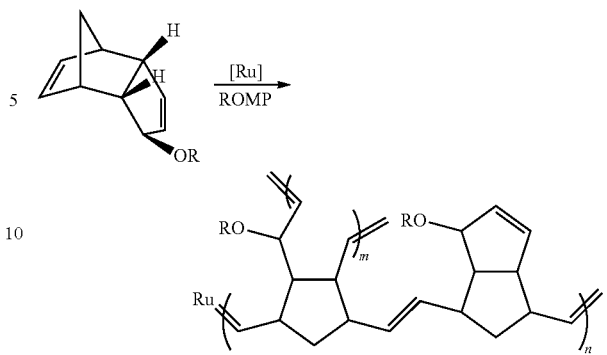

In the above reaction scheme, n indicates the degree of polymerization, m indicates the degree of cross-linking and Ru is a catalyst residue, e.g. a coordinated ruthenium group.

Other useful catalysts for polymerization of some neutral monomers of general Formulae (I) and (II) are described in (a) Diesendruck C. E., et al. J. Polym. Sci. Part A: Polym. Chem. 2009, 47, 4209-4213; (b) Grubbs, R. H. in Handbook of Metathesis, Volume 3: Polymer Synthesis, 2nd Ed, Wiley: New York, 2015; (c) Ginzburg, Y., et al., Organometallics, 2011, 30, 3430-3437; (d) Olefin Metathesis Theory and Practice, Edited by Karol Grela, 2014, John Wiley & Sons. ISBN: 978-1-118-20794-9.

Some DCPD derivatives of general Formula (II) were polymerized according to the ring opening metathesis polymerization (ROMP) reaction scheme shown above (the reaction took place at 100° C., with a ruthenium based catalyst cis-Ru—SPh or cis-Ru—S$^i$Pr, described in e.g. Ben-Asuly A. et al. Organometallics, 2009, 28, 4652-4655; Tzur E. et al., J. Organomet. Chem., 2014, 769, 24-28.

Endo-hydroxydicyclopentadiene (DCPD-OH) and a DCPD derivative of Formula 14:

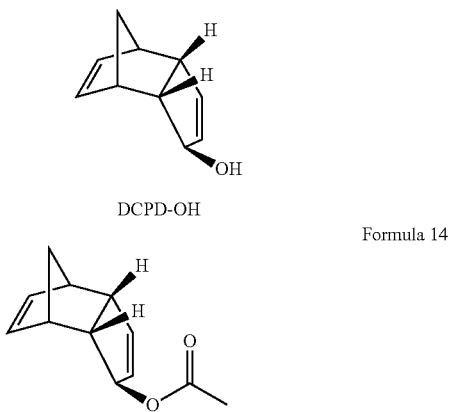

were also polymerized according to the ring opening metathesis polymerization (ROMP) reaction scheme shown above (the reaction took place at 70° C., with Grubbs' $2^{nd}$ generation catalyst).

Quaternary ammonium DCPD derivatives of general formula (I) were polymerized together with neutral monomers to yield covalent ionic crosslinked polymer. For example, the compound of formula 9 was polymerized together with hydroxy-DCPD (DCPD-OH) at a ratio exemplified by 1:50, according to the reaction scheme shown below (the reaction took place at 90° C., with the aid of a suitable catalyst):

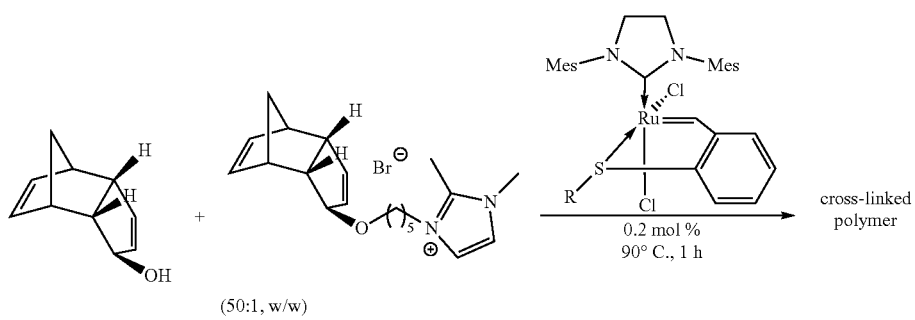

(50:1, w/w)

Polymerization reactions of compounds of Formulae 1-3 resulted in a solid, hard homopolymer. The polymerization reaction of compound of formula 4, resulted in rubbery, flexible and elastic, stretchable homopolymer. The polymer of compound of Formula 14 was also relatively soft, although not as flexible as the polymer of compound of Formula 4.

Copolymerization reactions of any one of a compound of Formula 6-9 with DCPD-OH at a ratio of 1:50, resulted in a solid, hard copolymer.

Copolymerization reactions of any one of a compound of Formula 6-9 with DCPD-OH at a ratio of 1:50 gave the hardest polymers. Whereas, copolymerization reactions of any one of a compound of Formula 6-9 with DCPD-OH at lower ratios, such as for example, 1:10 or 1:5 resulted in soft polymers.

Thus, according to additional aspects of the invention, provided herein is a polymer formed by polymerizing a DCPD derivatives of general Formula (I) or (II), either alone to form a homopolymer or in combination with one or more additional monomers to form a copolymer, at any suitable ratio.

Accordingly, provided herein is a polymer or a copolymer of Formula (V)

Formula (V)

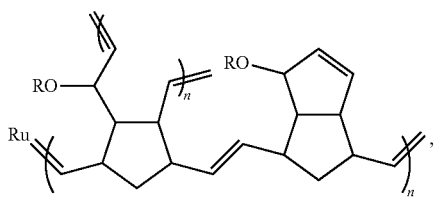

wherein:

R is as defined in Formula (I) above, n indicates the degree of polymerization, m indicates the degree of cross-linking, and Ru is a catalyst residue, e.g. a coordinated ruthenium group.

According to additional aspects, provided herein is a polymerization process, comprising: combining DCPD derivative of general Formula (I) or (II) and a catalyst; and optionally activating the catalyst, e.g. by heating, to form a homopolymer. For example, the process comprises dissolving the DCPD derivative and/or the catalyst in a suitable solvent, to improve homogeneity; and removing the solvent prior to or concomitantly with the heating.

According to additional aspects, provided herein is a polymerization process, comprising: combining DCPD derivative of general formula (I) or (II) and optionally an additional monomer(s) with a catalyst; and optionally activating the catalyst, e.g. by heating, to form a copolymer. For example, the process comprises dissolving the DCPD derivative and/or the catalyst in a suitable solvent, to improve homogeneity; and removing the solvent prior to or concomitantly with the heating.

In addition, provided herein is a polymerizable mixture, comprising a DCPD derivative of general formula (I) or (II), and a catalyst, preferably a ruthenium based catalyst. Also, provided herein is a polymerizable mixture comprising endo-hydroxydicyclopentadiene and a catalyst, preferably a ruthenium based catalyst. In some preferred embodiments the polymerizable mixture comprises endo-hydroxydicyclopentadiene, a catalyst and one or more of a DCPD derivative of general formula (I) or (II). In various preferred embodiments, the polymerizable mixture further comprises a solvent in which the DCPD derivative and/or the additional monomer and/or the catalyst are dissolved, preferably the catalyst is dissolved in a solvent.

The polymerization reactions and the polymerizable mixtures of the present invention employ a catalyst. Preferably, the catalyst/monomer ratio ranges from 1:100 and up to 1:100,000, preferably from 1:500 and up to 1:5,000. Preferably, the catalyst is Grubbs' $2^{nd}$ generation catalyst. Non-limiting examples of preferable catalysts include commercial ruthenium based catalyst for olefin metathesis reactions and sulfur chelated ruthenium catalyst synthesized as described in Kost, T. et al, *Journal of Organometallic Chemistry*, 2008, 693, 2200-2203.

Prior to the polymerization reaction, the monomer(s) and the catalysts are sometimes dissolved in a solvent. Dry solvents are preferred. Non-limiting examples of suitable solvents for the polymerization processes are solvents such as chloroform or dichloromethane (DCM). The solvent is added to the monomer(s)-catalyst mixture, e.g. to obtain homogeneous mixture.

Once all the components of the polymerization reaction are dissolved, the solvent is removed by conventional techniques, e.g., by evaporation, and the reaction mixture is heated to a suitable temperature, preferably between room temperature and about 150° C., inclusive, to allow occurrence of the polymerization reaction. For example, the temperature of the polymerization reaction for neutral DCPD derivatives of general formula (I) or (II) is in the range of 45° C.-90° C., inclusive, more preferably in the range of 50-70° C., inclusive. Preferably, the temperature of the polymerization reaction for ionic (quaternary ammonium) DCPD derivatives of general formula (I) or (II) is in the range of 65° C.-95° C., inclusive, more preferably in the range of 70-90° C., inclusive. The temperature is selected to be above the highest melting point of each monomer, but below the degradation temperature of the catalyst. For example, the sulfur-chelated catalysts may be heated to up to 150° C., whereas Hoveyda catalysts to no more than 120° C. Catalysts responsive to UV irradiation may also be used to advance the polymerization reaction, e.g. described in US2014/0155511 A1.

The polymerization reaction results in a solid hard polymer or in a rubbery flexible polymer, depending on the nature of the monomers. In the case of copolymers, the hardness of the polymer may also depend on the ratio of the monomers that are used for the formation of the copolymer.

Thus, it has now been shown by the present inventors that DCPD derivatives disclosed herein allow for tuning of diverse material properties that go from rubbery thermoset materials to hard glasses and from more hydrophilic surfaces to more hydrophobic. Even though the substituted polymers degrade at somewhat lower temperatures compared with the polymer of endo-DCPD (pDCPD) (less than 10% weight reduction under 200° C. for all), the obtained (odourless) polymers were shown to retain thermal properties similar to those seen in the parent polymer and thus provide for a more appealing alternative for use, e.g. in the field of thermoset polymers produced by ROMP.

The resulting polymers are useful in commercial and industrial applications, including, for example, body panels for cars, trucks, buses and all types of off-highway equipment, wastewater treatment equipment, sewage plants, pipeline valves, filters and more. Such uses form another aspect of the invention.

BRIEF DESCRIPTION OF THE FIGURES

FIG. 2E provides a TGA curve of compound of Formula 1.

FIG. 3F provides a COSY NMR spectrum of compound of Formula 3 in CDCl$_3$.

FIG. 4G provides a HMQC spectrum of compound of Formula 4 in CDCl$_3$.

EXAMPLES

Materials

Figure 1A:
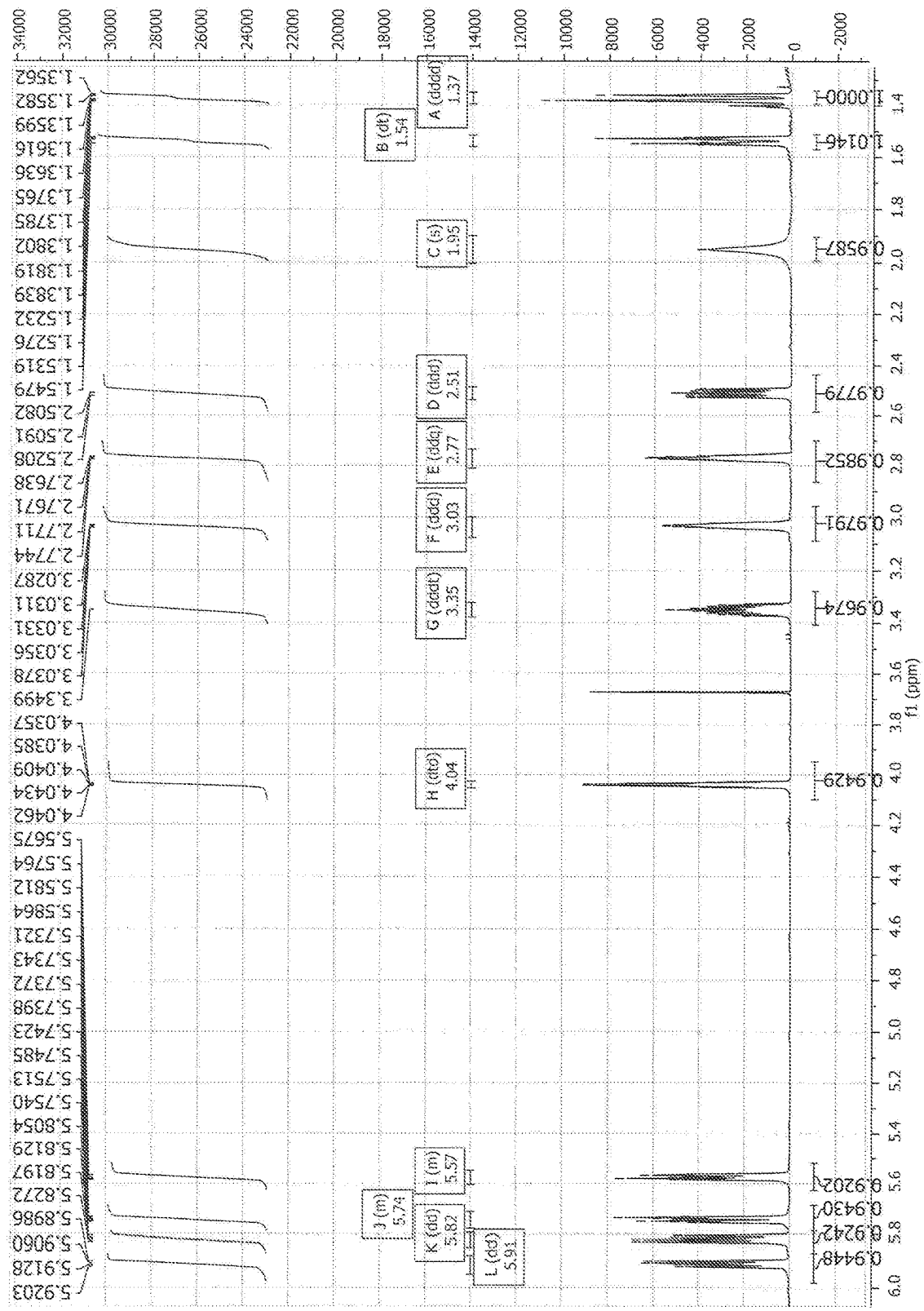
FIG. 1A provides a $^1$H-NMR spectrum of hydroxydicyclopentadiene (DCPD-OH).

All reagents were purchased from usual suppliers and were used without further purification.

Solvents were dried and stored on molecular sieves or alkali metals.

Yields refer to isolated compounds greater than 95% purity as determined by proton Nuclear Magnetic Resonance spectroscopy ($^1$H-NMR) analysis.

Methods $^1$H— and $^{13}$C-NMR spectra were recorded either with Bruker 400 MHz or 500 MHz FT NMR (model Avance-DPX 400 or DPX 500) instruments with chemical shifts reported in ppm relative to the residual in the deuterated solvent or the internal standard tetramethylsilane. HR-MS data were obtained using a thermoscientific LTQU XL Orbitrap HR-MS equipped with APCI (atmospheric pressure chemical ionization). TGA analysis was performed using a Mettler-Toledo instrument model TGA/SDTA851. 5-7 mg sample were heated in a standard 70 μL TGA alumina crucible from room temperature to 600° C., with a heating rate of 10° C./min in nitrogen atmosphere 50 ml/min. The results were analysed by STAR$^e$ software 12.00. The cross-linked thermoset polymers were also subjected to the differential scanning calorimetric analysis (DSC) with a METTLER-TOLEDO DSC 823 and results were evaluated with the STAR$^e$ software. Each sample was subjected to a 2-3 heating cooling cycles. Each cycle contained a heating segment followed by a cooling segment at a heating rate of 5° C./min. The viscoelastic properties of the pDCPD-OR were evaluated from 25° C. to lowest storage modulus (E') temperature with the heating rate of 2° C./min using dynamic mechanical analysis (DMA) (METTLER TOLEDO DMA 1 STARe system) at different frequencies e.g. 0.1 Hz, 1 Hz and 10 Hz while experimental results were evaluated using the STARe software version 14.00. However, for very soft material like pDCPDOOc (the polymer of compound of Formula 4), the measurement was performed in the temperature range −100° C. to 10° C. until the E' reached a minimum value at the same frequencies. The values of the storage modulus (E'), loss modulus (E") and loss tangent (tan δ=E"/E') for multiple frequencies were measured as a function of temperature. FTIR for the thin films was measured by using a Jasco FT/IR-460 Plus Fourier transform infrared spectrometer.

Preparation 1

Preparation of endo-hydroxydicyclopentadiene (DCPD-OH)

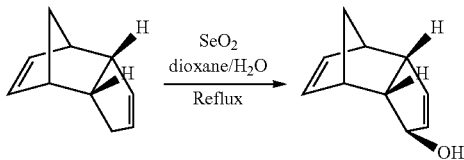 [SMILES: C1=C[C@H]2C3C=CC(C3)[C@H]2C1 ; O[C@@H]1C=C[C@H]2C3C=CC(C3)[C@@H]12]

Endo-dicyclopentadiene (endo-DCPD) (40.0 g, 0.303 mol) was dissolved in 120 ml of 9:1 v/v THF/$H_2O$ solution or in 120 ml of 9:1 v/v dioxane/water solution. Selenium dioxide (40.08 g, 0.361 mol) was added in one portion, the solution was refluxed for 3 hours and cooled to room temperature. The solvent was removed in vacuo and the viscous brown oil was dissolved in 200 ml of diethyl ether, dried on magnesium sulfate, filtered and the solvent again evaporated. The crude brown oil was distilled at 1.5 mbar, the fraction at 74-76° C. was collected to afford 30 g, (67%) as a pale yellow oil which crystallized at 4° C. to a pale yellow solid, M.P. at 30-35° C.

$^1$H NMR (400 MHz, $CDCl_3$) δ 5.91 (dd, J=5.7, 3.0 Hz, 1H), 5.82 (dd, J=5.7, 3.0 Hz, 1H), 5.78-5.71 (m, 1H), 5.61-5.55 (m, 1H), 4.04 (dtd, J=3.3, 2.2, 1.2 Hz, 1H), 3.35 (dddt, J=7.3, 4.2, 3.0, 2.0 Hz, 1H), 3.03 (ddd, J=3.4, 2.4, 1.5 Hz, 1H), 2.77 (ddq, J=5.6, 2.9, 1.4 Hz, 1H), 2.51 (ddd, J=7.2, 4.4, 2.1 Hz, 1H), 1.95 (s, 1H), 1.54 (dt, J=8.1, 1.8 Hz, 1H), 1.37 (dddd, J=8.1, 2.1, 1.4, 0.6 Hz, 1H).

$^{13}$C NMR (101 MHz, $CDCl_3$) δ 137.76, 135.41, 134.63, 132.38, 78.92, 54.64, 53.37, 51.23, 44.77, 44.62.

Figure 1B:
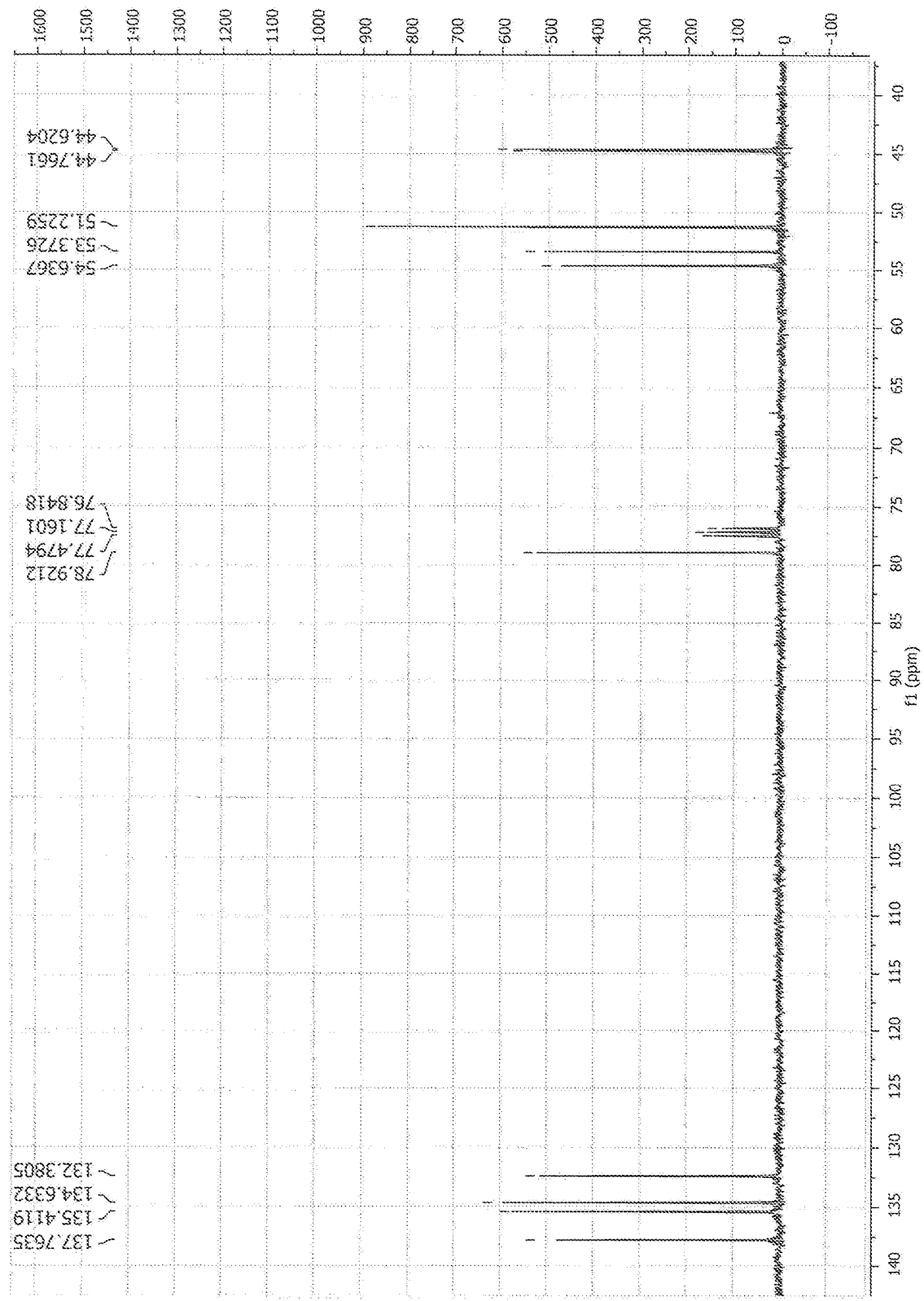
FIG. 1B shows a $^{13}$C-NMR spectrum of hydroxydicyclopentadiene (DCPD-OH).

$^1$H— and $^{13}$C-NMR spectra of hydroxydicyclopentadiene (DCPD-OH) are provided in FIGS. 1A and 1B, respectively.

Figure 1C:
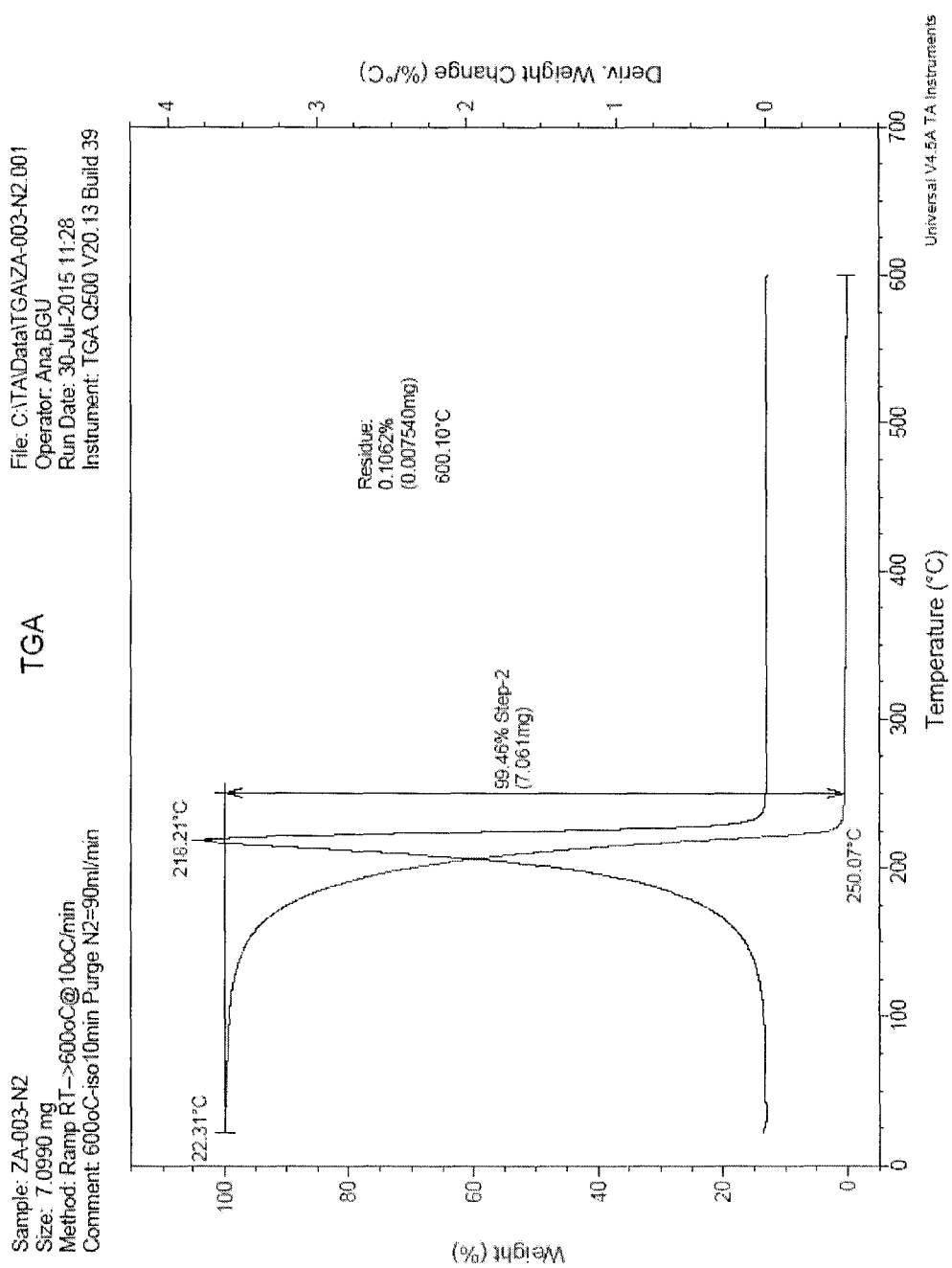
FIG. 1C shows a TGA curve of hydroxydicyclopentadiene.

TGA curve of hydroxydicyclopentadiene (DCPD-OH) is provided in FIG. 1C.

Figure 1D:
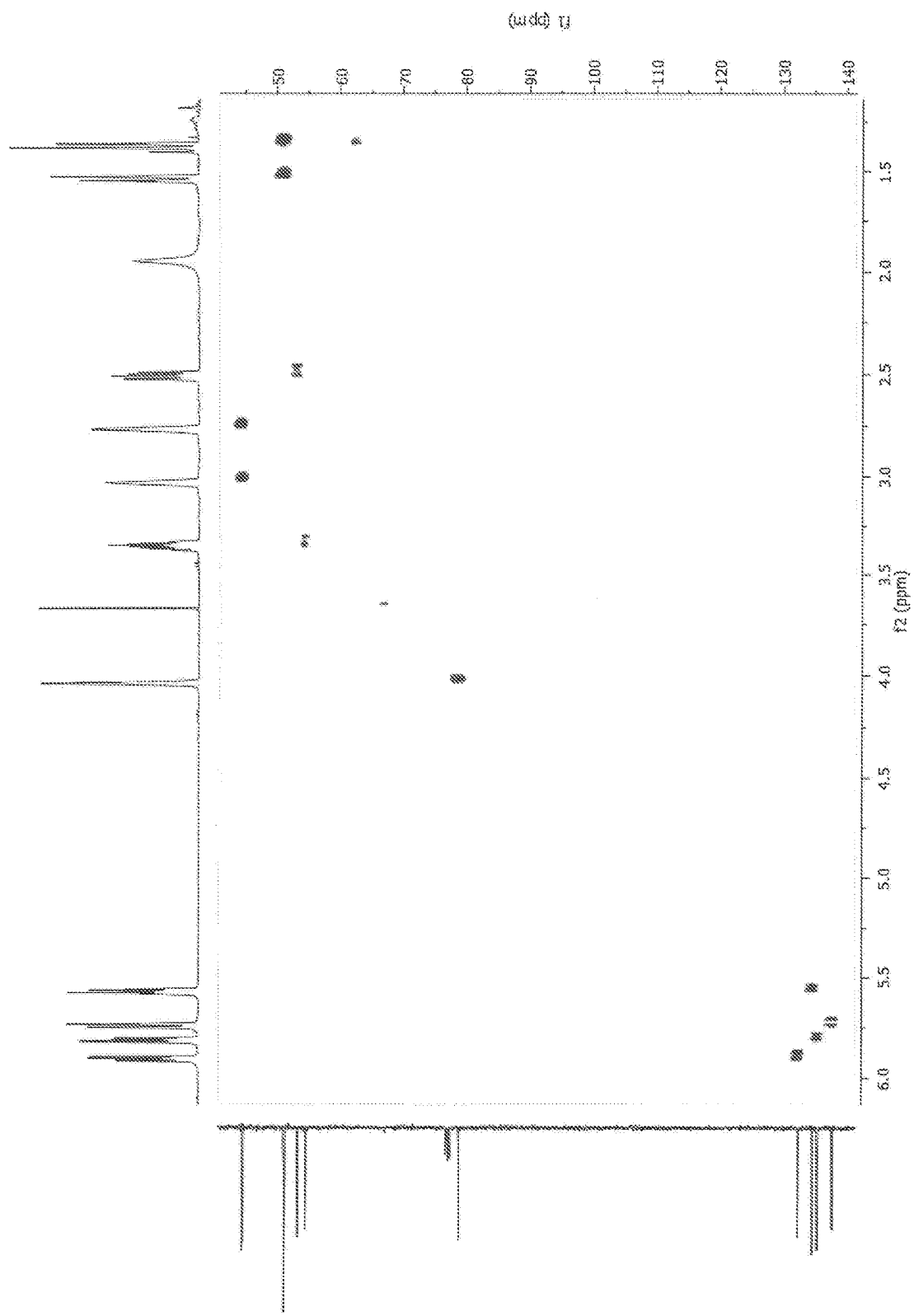
FIG. 1D provides a HMQC spectrum of hydroxyl-dicyclopentadiene (DCPD-OH) in CDCl$_3$.

HMQC spectrum of hydroxydicyclopentadiene (DCPD-OH) in $CDCl_3$ is provided in FIG. 1D.

Example 1

Preparation of Compounds of Formulae 1, 3 and 4, as Performed for the Compound of Formula 4

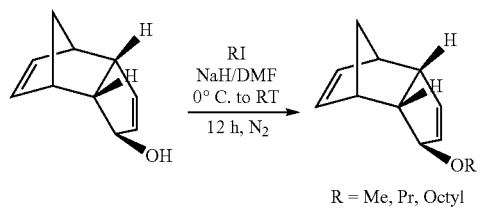

R = Me, Pr, Octyl

A three necked round bottom flask was charged with hydroxydicyclopentadiene (1 gm, 6.75 mmol) and NaH (405 mg, 10.13 mmol, 60%) and subjected to vacuum and then nitrogen, consecutively three times. Then, dry DMF (20 ml) was added to the flask and the reaction mixture was stirred at 0° C. for 10 minutes. A purple colored solution was observed. After that, 1-Iodooctane (2.43 gm, 10.13 mmol) was added through syringe in drop wise fashion, purple color disappeared and a pale white solution was observed during addition. It was then kept for 12 hours stirring at room temperature. After that, it was diluted with ethyl acetate (60 ml) and washed with saturated aqueous $NH_4Cl$ solution. The organic layer was then separated and dried over $MgSO_4$. It was finally concentrated and subjected to flash column chromatography for purification. The expected product was eluted with Ethyl acetate/Petroleum ether (1:19) on silica gel stationary phase as a light yellowish liquid.

Isolated Yield: 1.03 gm (~59%)

All three ethers are liquid at room temperature.

Following are the $^1$H— and $^{13}$C-NMR spectral data for compound of Formula 1:

$^1$H NMR (500 MHz, $CDCl_3$) δ 5.95 (dd, J=5.6, 2.9 Hz, 1H), 5.86 (dd, J=5.6, 3.0 Hz, 1H), 5.82 (d, J=4.9 Hz, 1H), 5.65 (d, J=5.7 Hz, 1H), 3.71 (d, J=1.1 Hz, 1H), 3.40-3.33 (m, 1H), 3.31 (s, 3H), 2.99 (s, 1H), 2.79 (s, 1H), 2.66-2.53 (m, 1H), 1.57 (d, J=8.1 Hz, 1H), 1.43 (d, J=8.1 Hz, 1H).

$^{13}$C NMR (126 MHz, $CDCl_3$) δ 138.66, 135.57, 132.50, 131.96, 88.02, 55.75, 54.84, 51.46, 49.71, 45.36, 44.68.

Figure 2A:
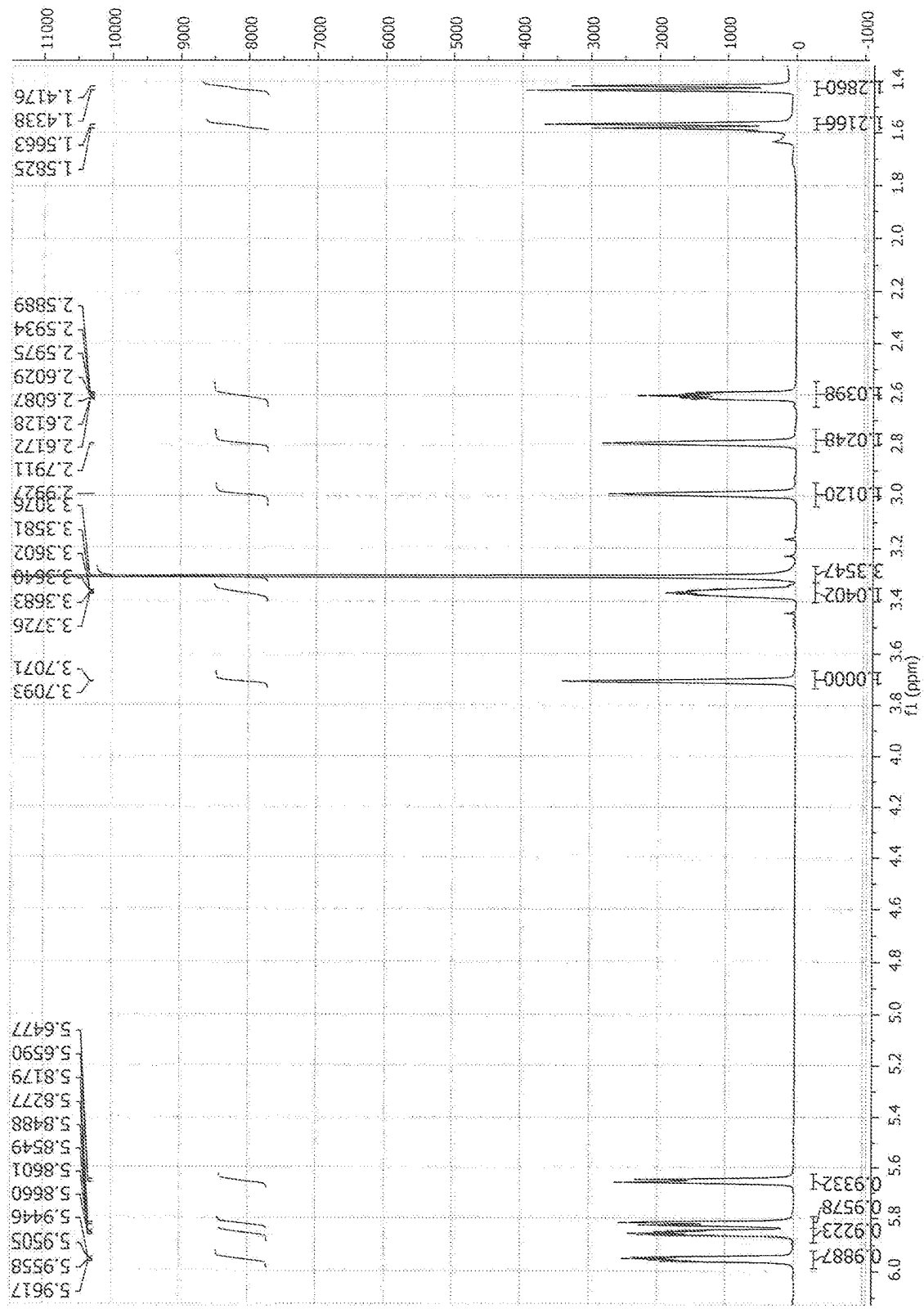
FIG. 2A shows a $^1$H-NMR spectrum of compound of Formula 1.
Figure 2B:
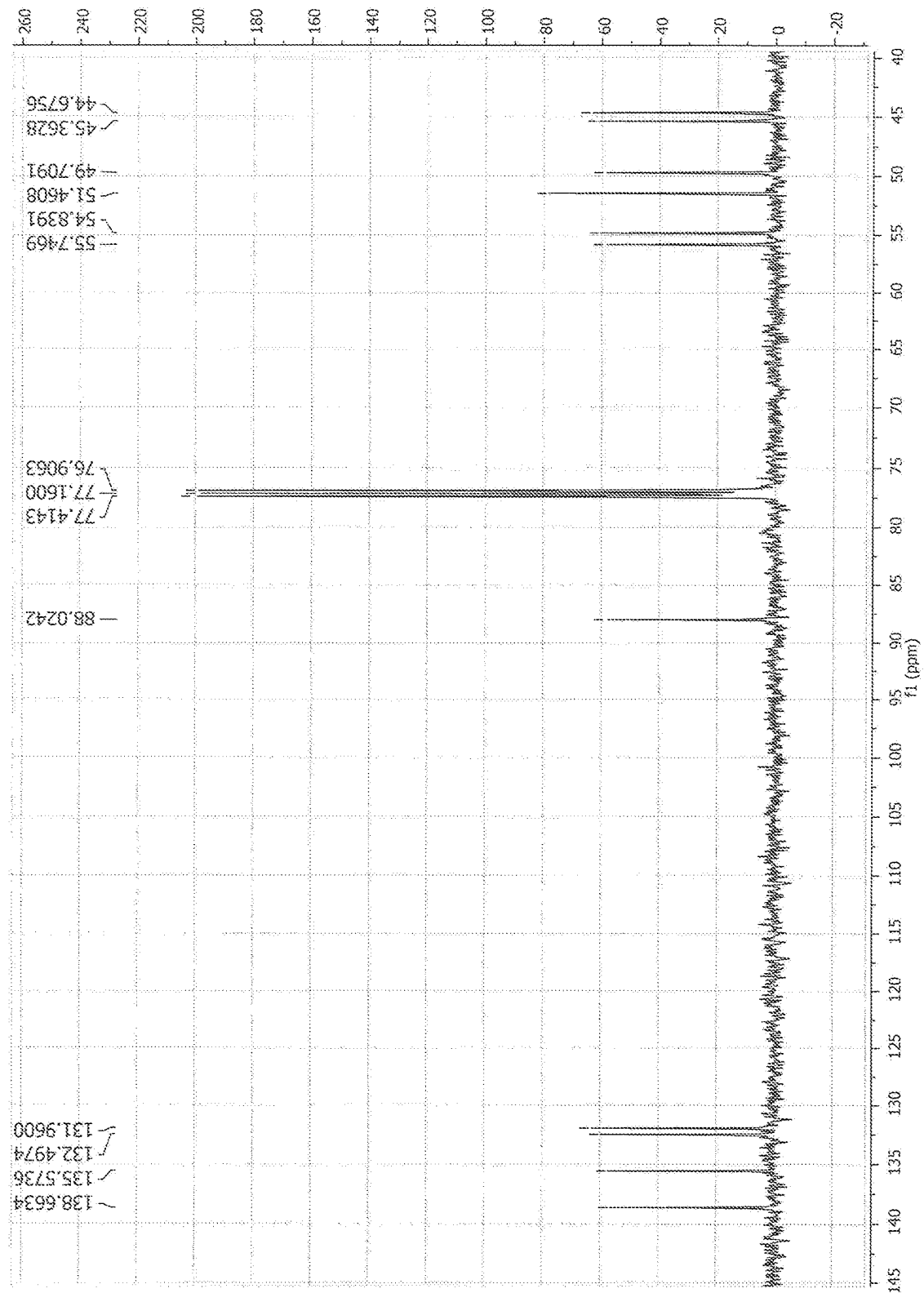
FIG. 2B provides a $^{13}$C-NMR spectrum of compound of Formula 1.

$^1$H— and $^{13}$C-NMR spectra for compound of Formula 1 are provided in FIGS. 2A and 2B, respectively.

Figure 2C:
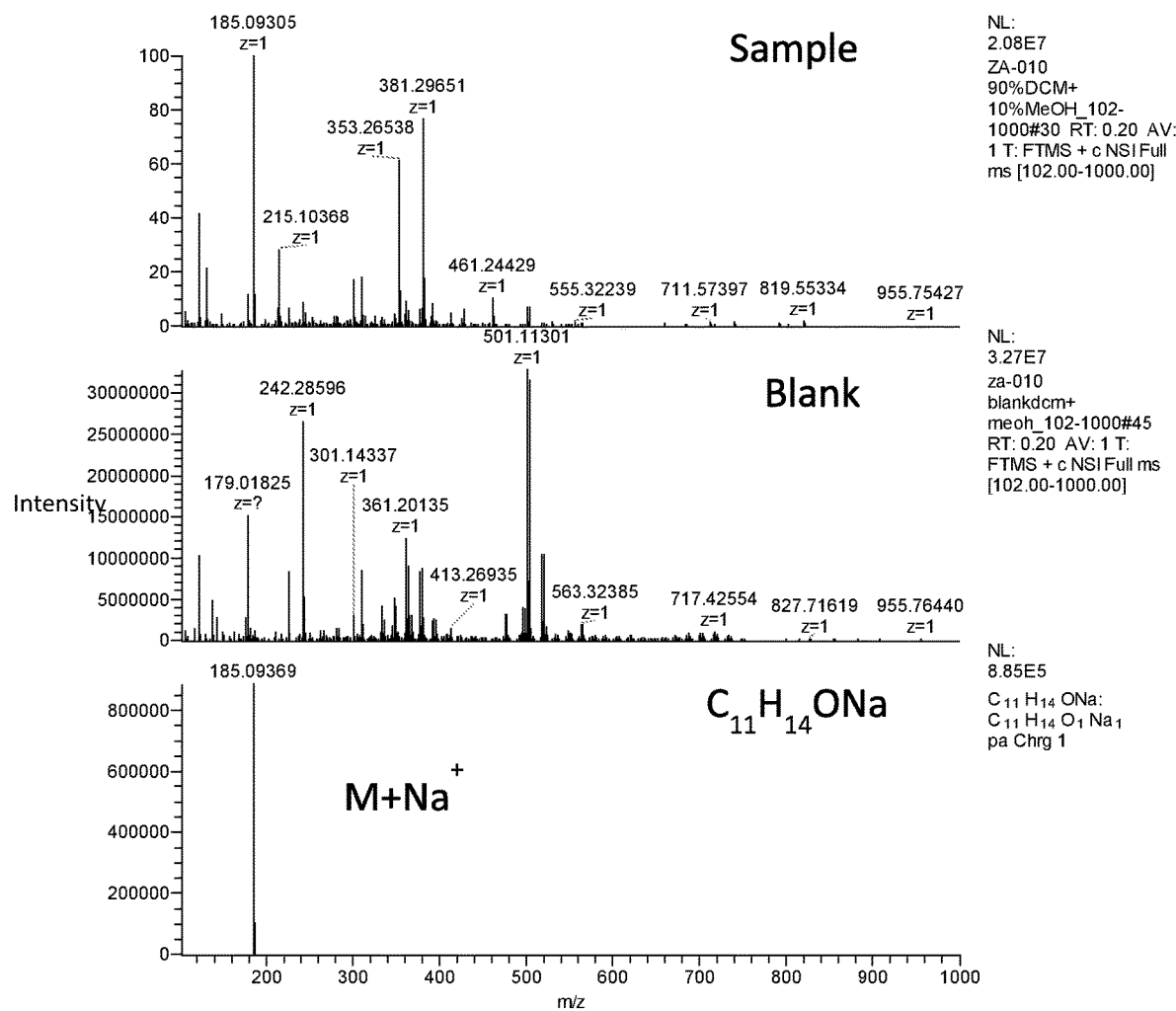
FIGS. 2C and 2D show HRMS spectra of the sodium salt of compound of Formula 1.
Figure 2D:
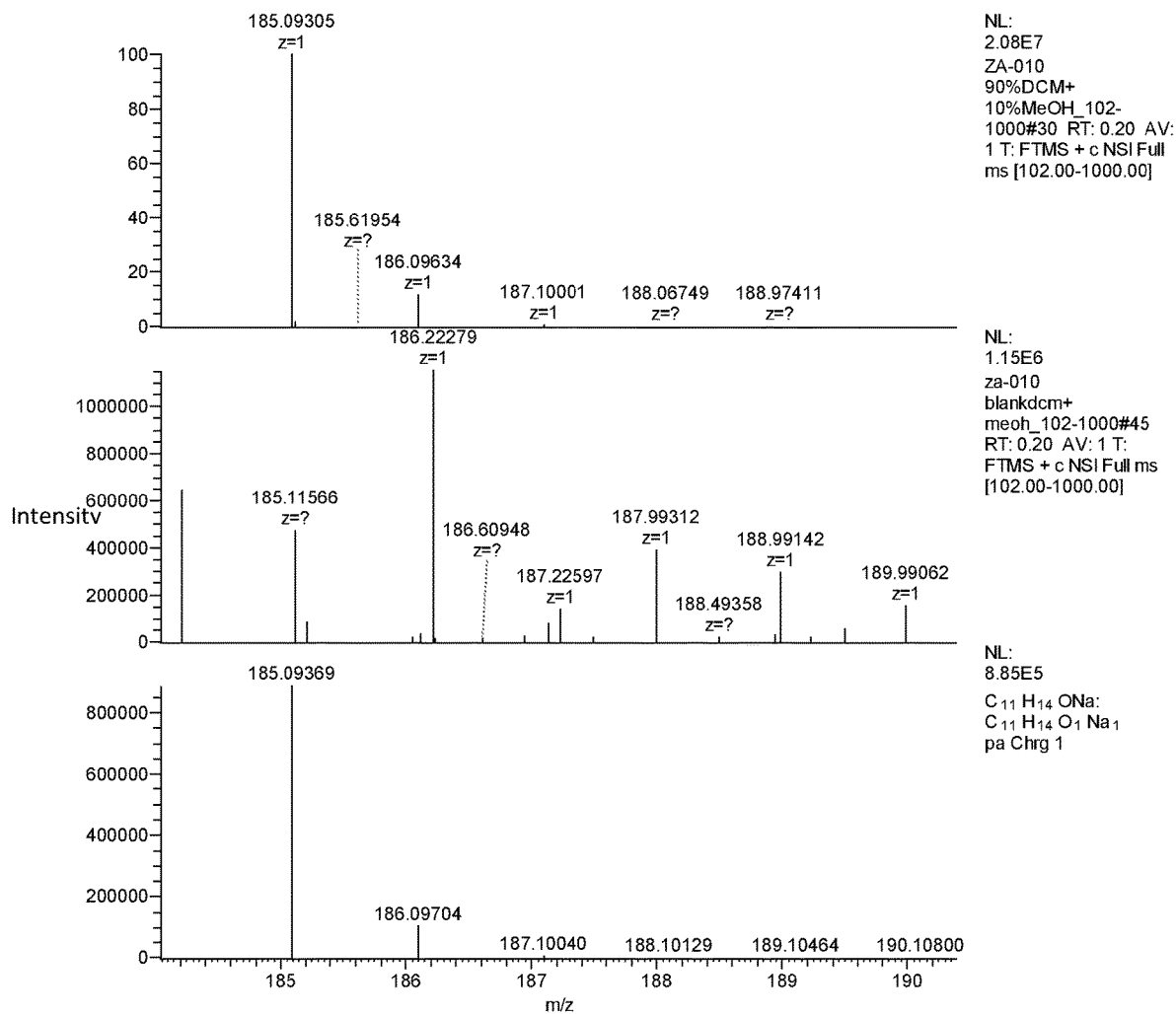

HRMS spectrum for the sodium salt of compound of Formula 1 are provided in FIGS. 2C and 2D.

TGA curve of compound of Formula 1 is provided in FIG. 2E.

Figure 2F:
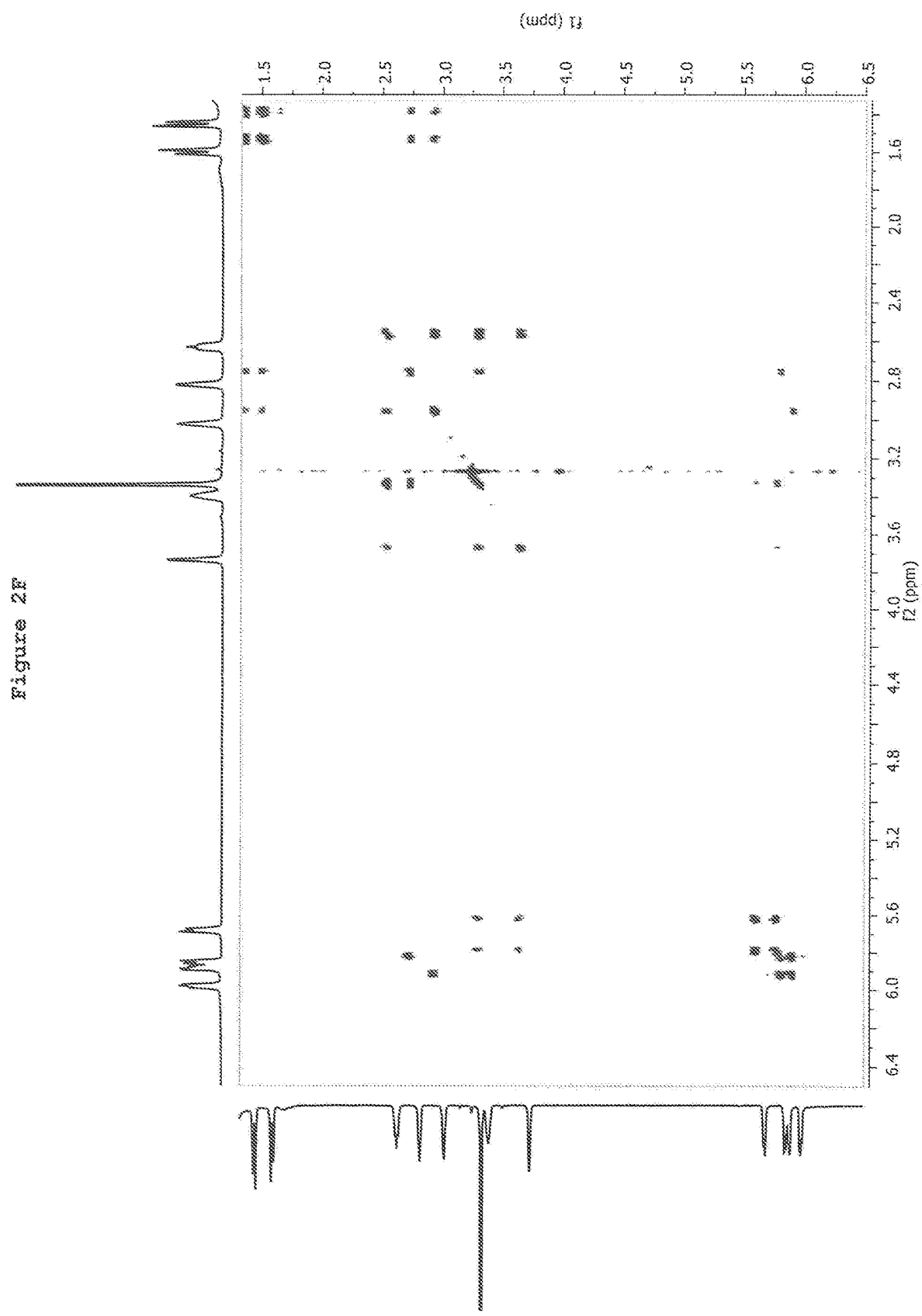
FIG. 2F provides a COSY NMR spectrum of compound of Formula 1 in CDCl$_3$.

COSY NMR spectrum of compound of Formula 1 in $CDCl_3$ is provided in FIG. 2F.

Figure 2G:
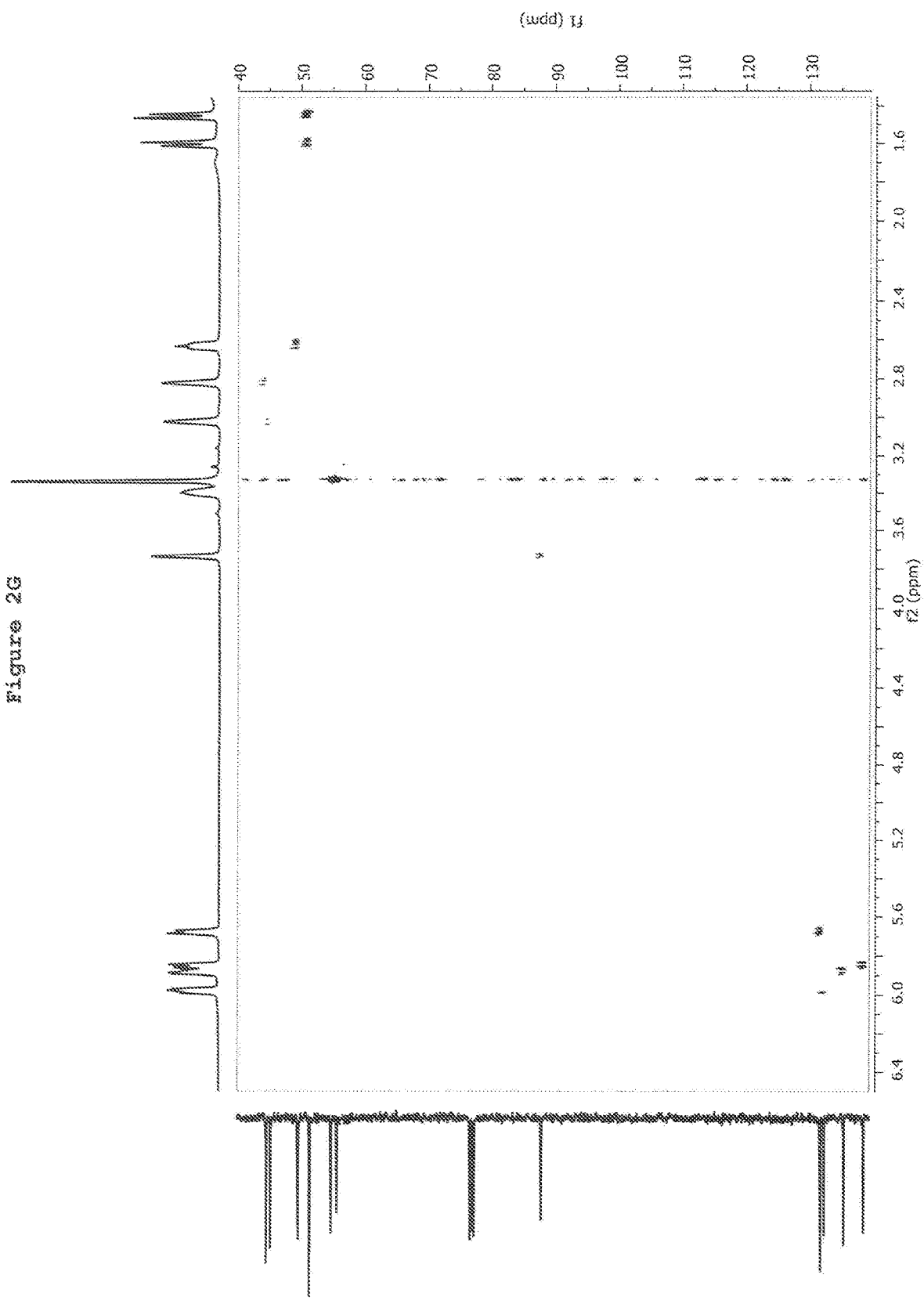
FIG. 2G provides a HMQC NMR spectrum of compound of Formula 1 in CDCl$_3$.

HMQC NMR spectrum of compound of Formula 1 in $CDCl_3$ is provided in FIG. 2G.

Following are the $^1$H— and $^{13}$C-NMR spectral data for compound of Formula 3:

$^1$H NMR (500 MHz, $CDCl_3$) δ 5.95 (dd, J=5.6, 2.9 Hz, 1H), 5.86 (dd, J=5.6, 3.0 Hz, 1H), 5.80 (d, J=5.7 Hz, 1H), 5.72-5.58 (m, 1H), 3.77 (d, J=1.8 Hz, 1H), 3.43 (dt, J=8.8, 6.9 Hz, 1H), 3.39-3.26 (m, 2H), 2.99 (s, 1H), 2.78 (s, 1H), 2.65-2.57 (m, 1H), 1.61-1.54 (m, 3H), 1.41 (d, J=8.1 Hz, 1H).

$^{13}$C NMR (126 MHz, $CDCl_3$) δ 138.24, 135.58, 132.54, 132.50, 86.61, 70.33, 54.85, 51.47, 50.18, 45.37, 44.67, 23.44, 10.84.

Figure 3A:
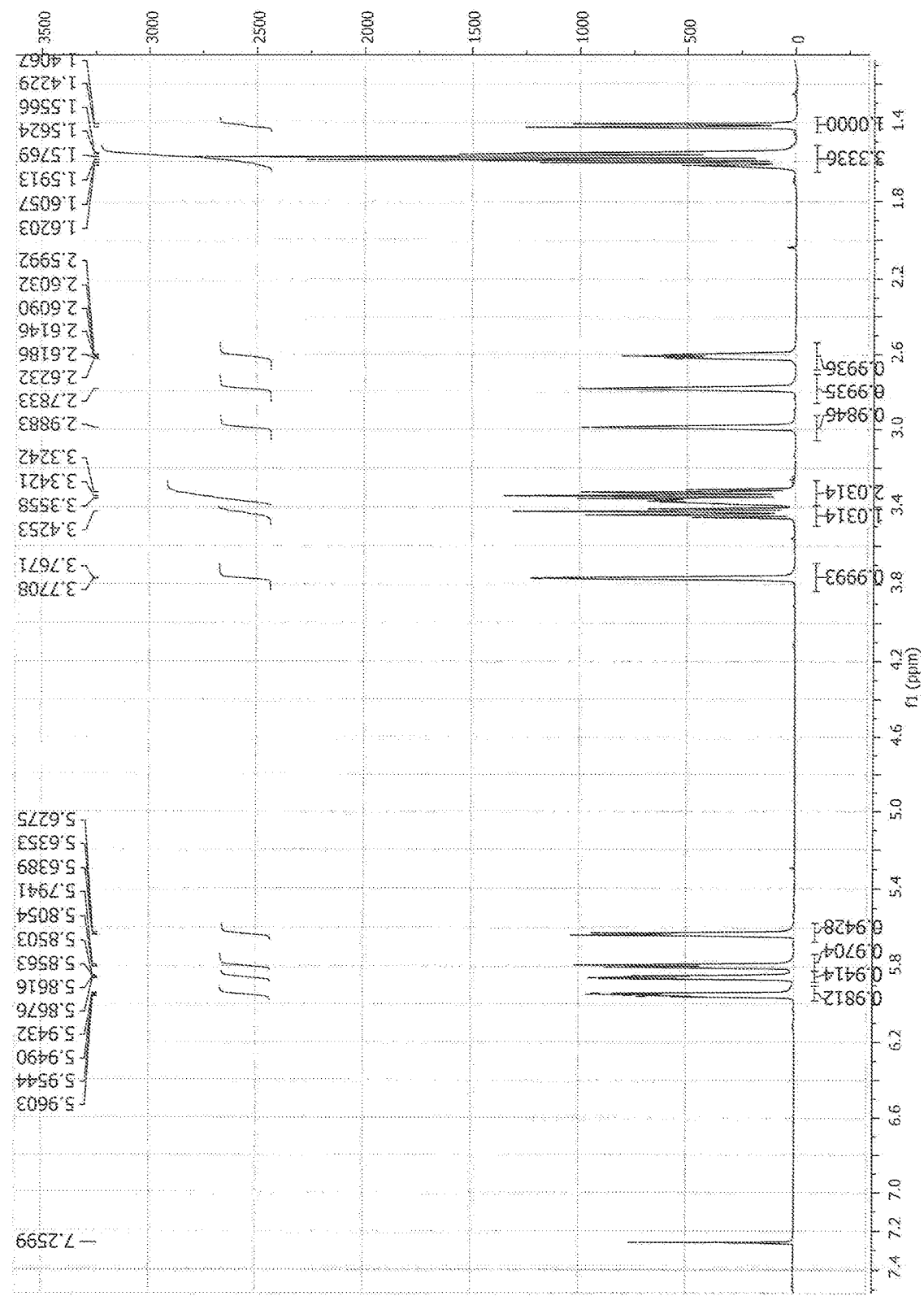
FIG. 3A provides a $^1$H-NMR spectrum of compound of Formula 3.
Figure 3B:
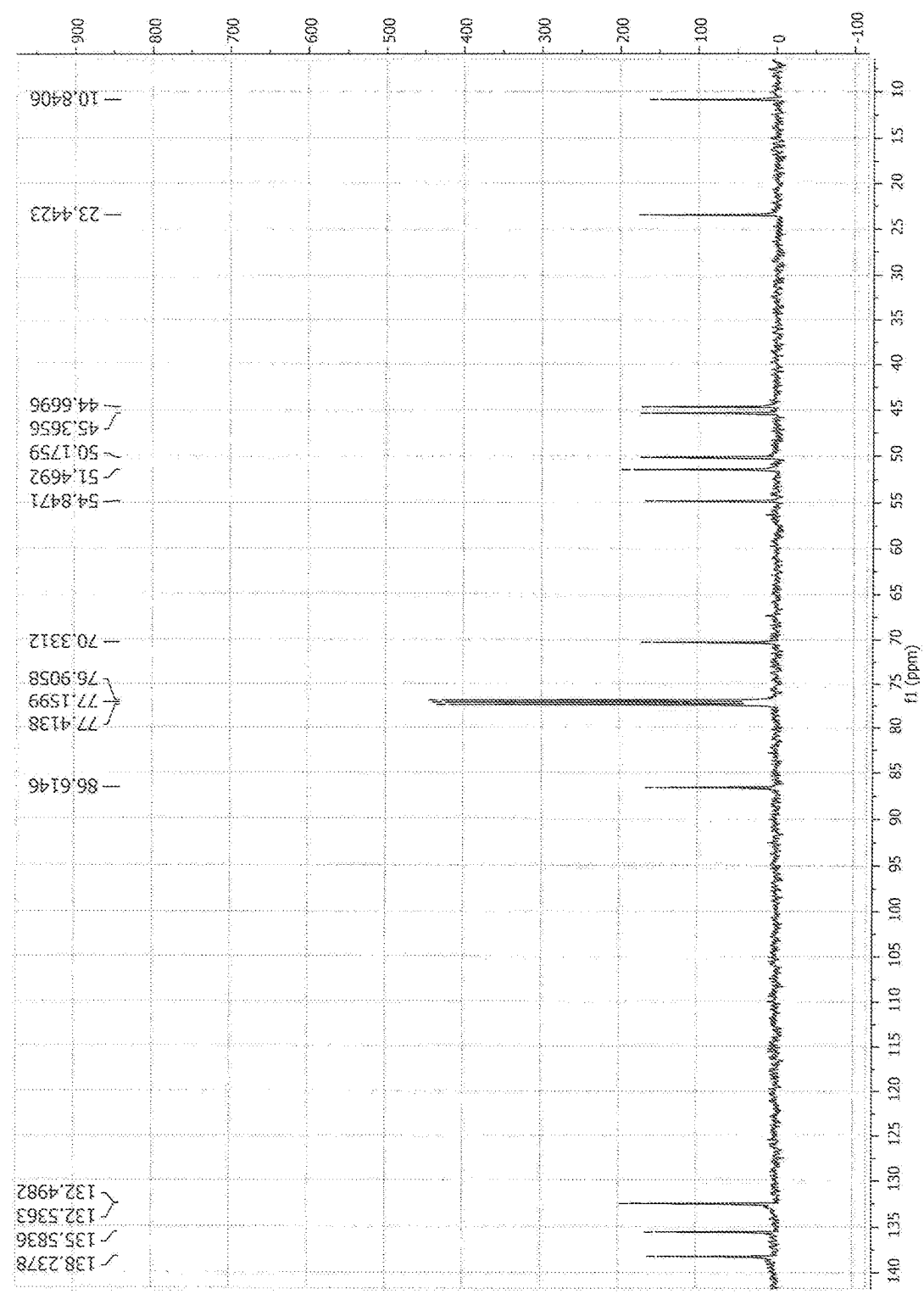
FIG. 3B provides a $^{13}$C-NMR spectrum of compound of Formula 3.

$^1$H— and $^{13}$C-NMR spectra for compound of Formula 3 are provided in FIGS. 3A and 3B, respectively.

Figure 3C:
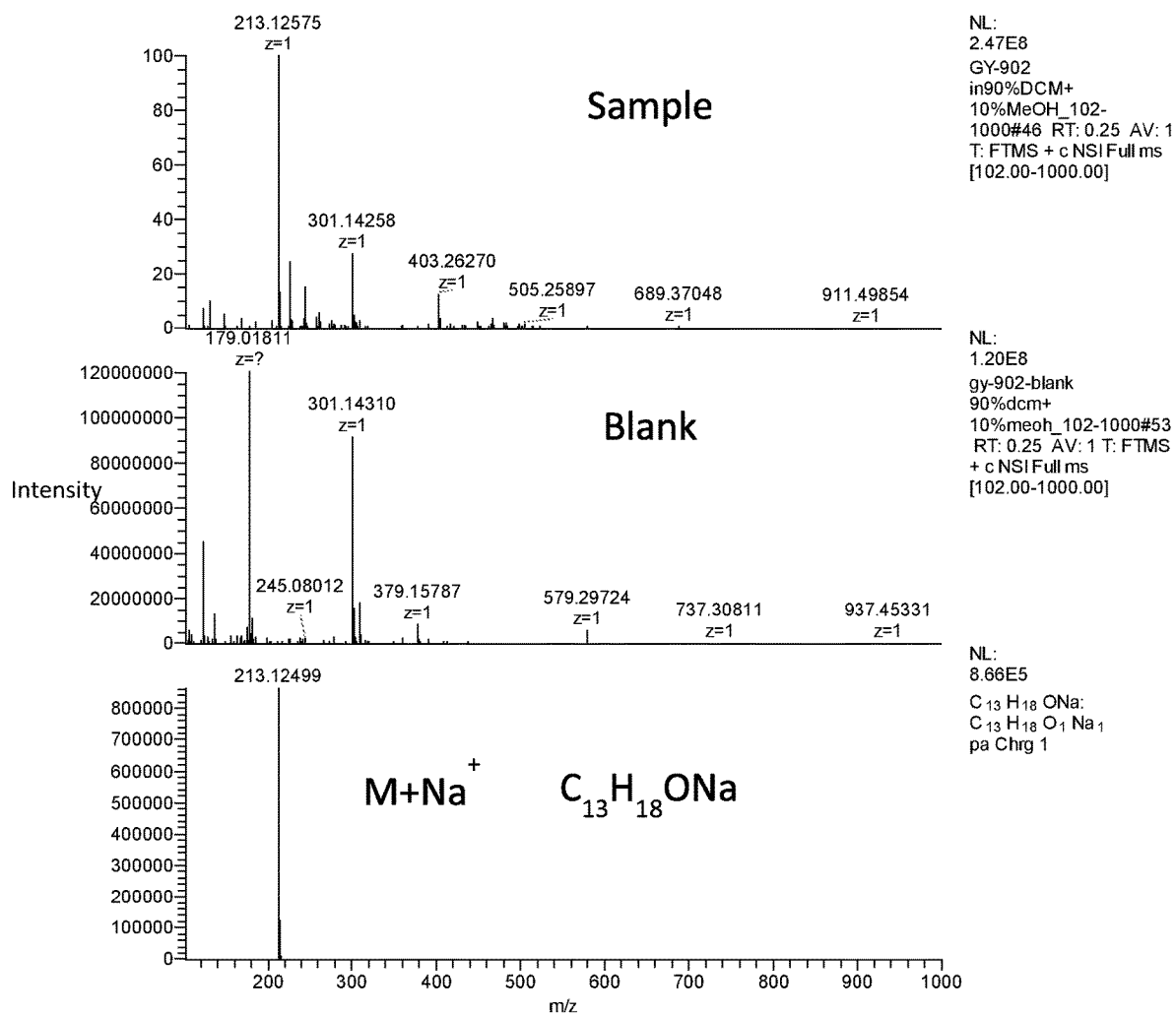
FIGS. 3C and 3D show HRMS spectra for the sodium salt of compound of Formula 3.
Figure 3D:
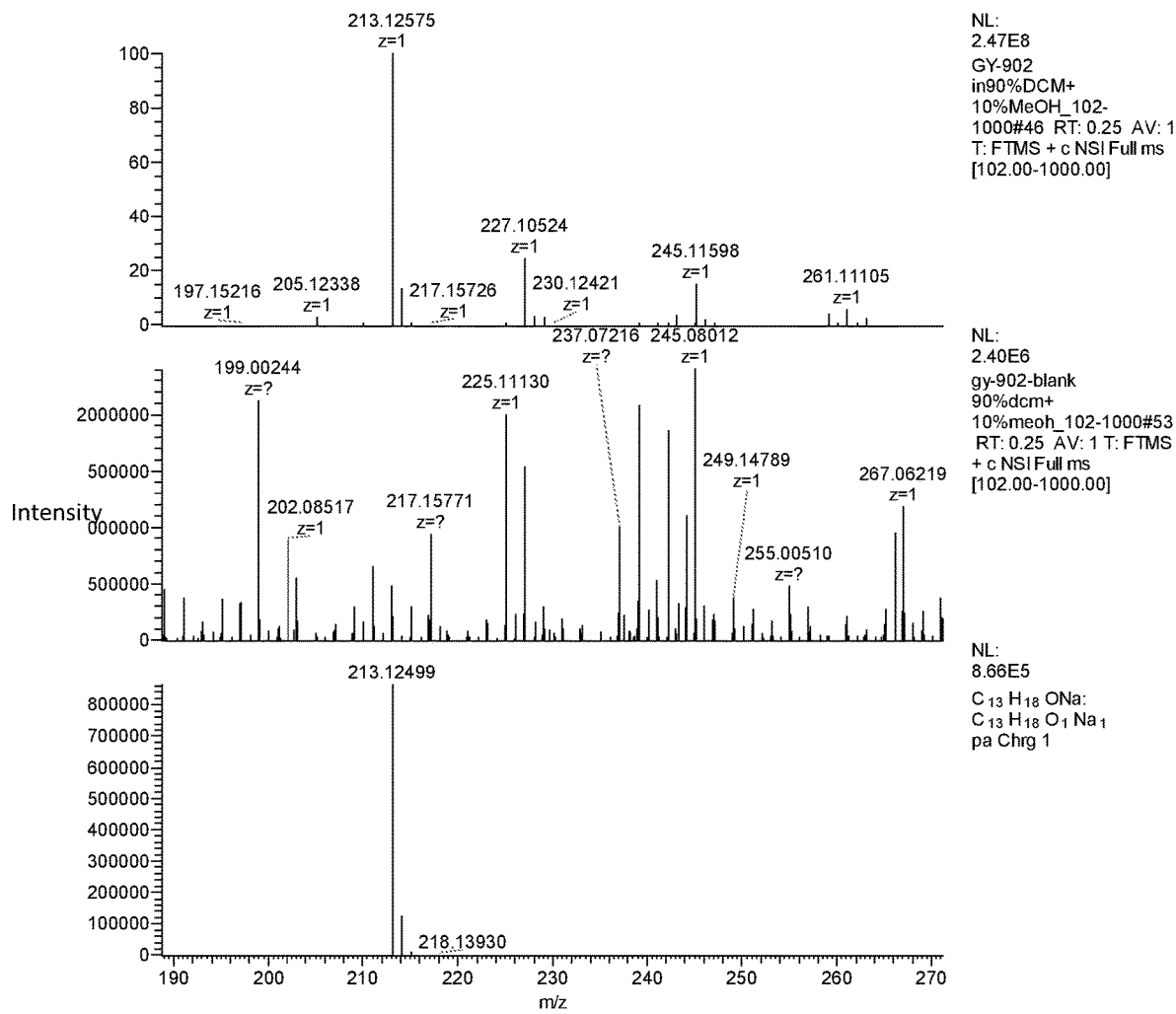

HRMS spectra for the sodium salt of compound of Formula 3 are provided in FIGS. 3C and 3D.

Figure 3E:
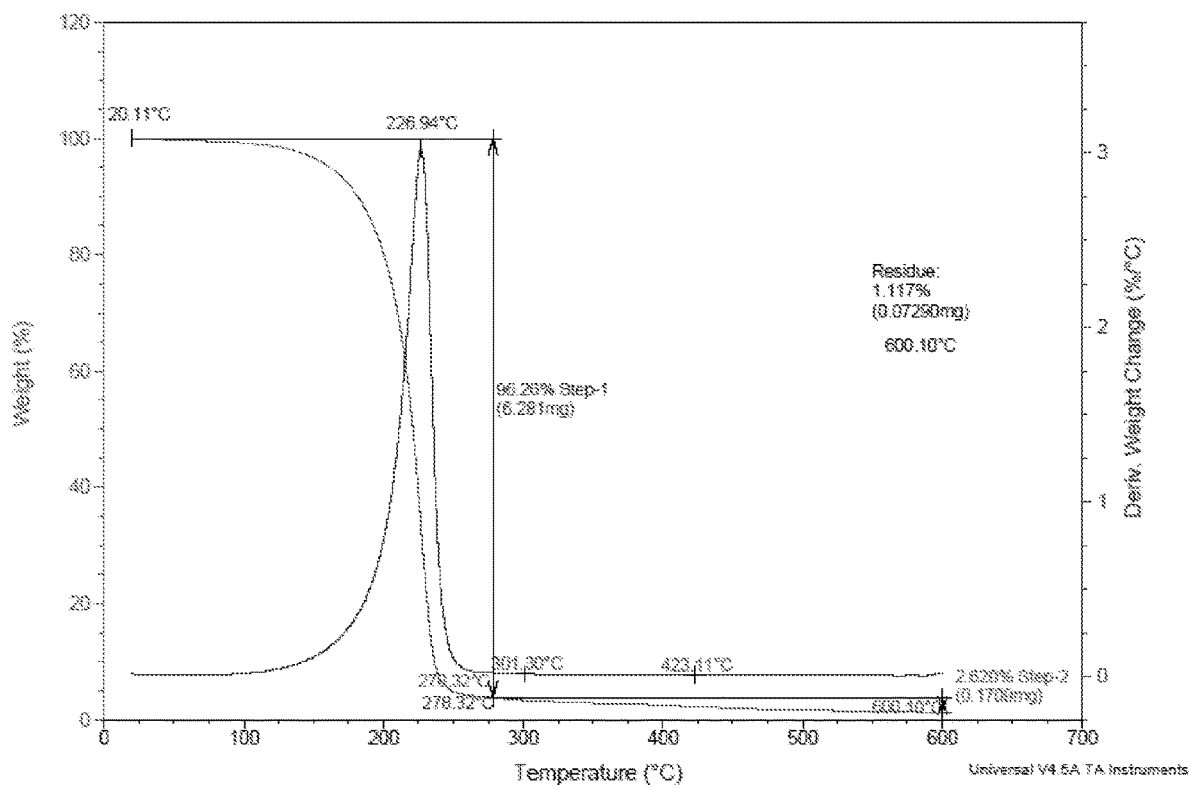
FIG. 3E provides a TGA curve of compound of Formula 3.
Figure 3E:
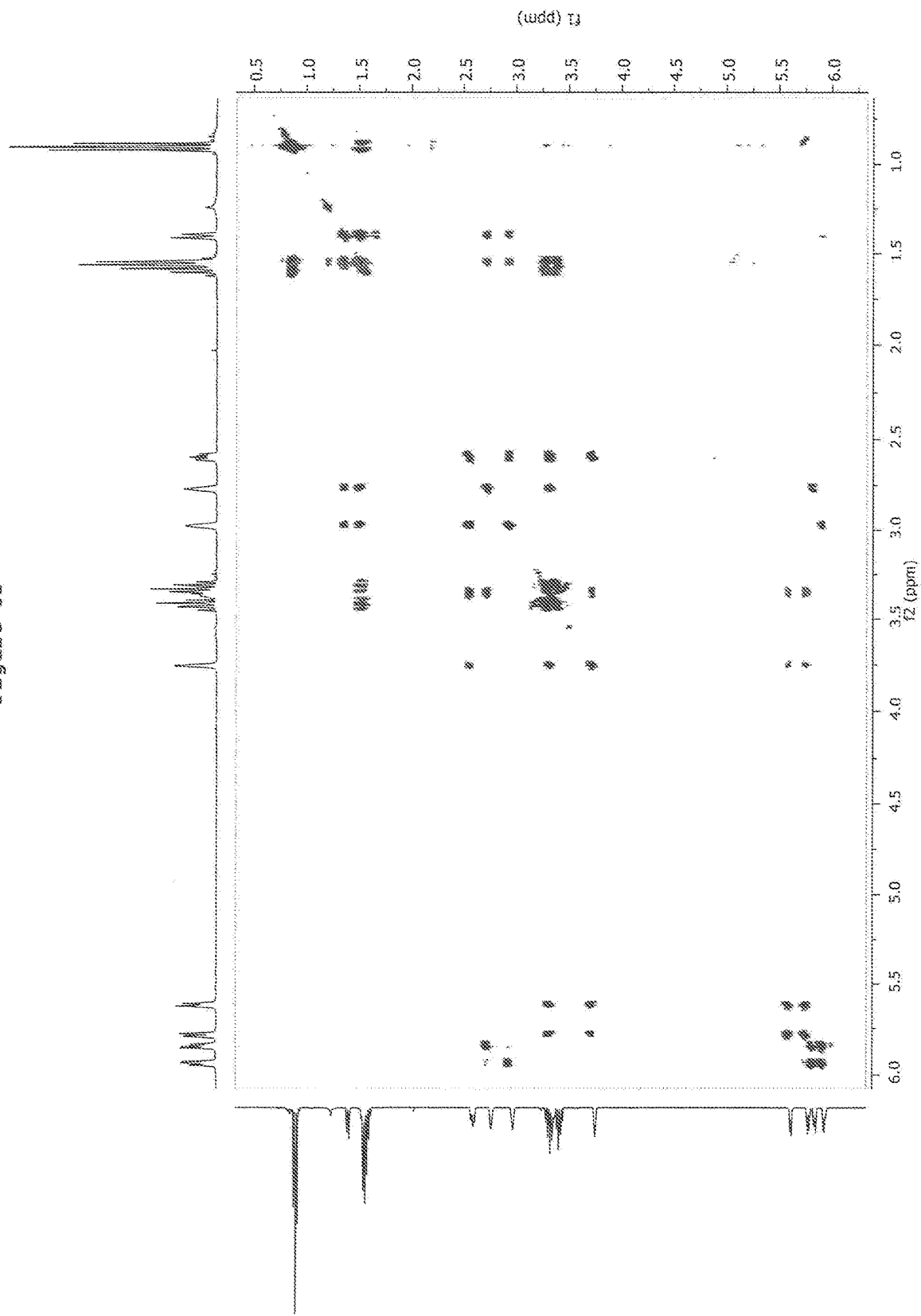

TGA curve of compound of Formula 3 is provided in FIG. 3E.

COSY NMR spectrum of compound of Formula 3 in $CDCl_3$ is provided in FIG. 3F.

Figure 3G:
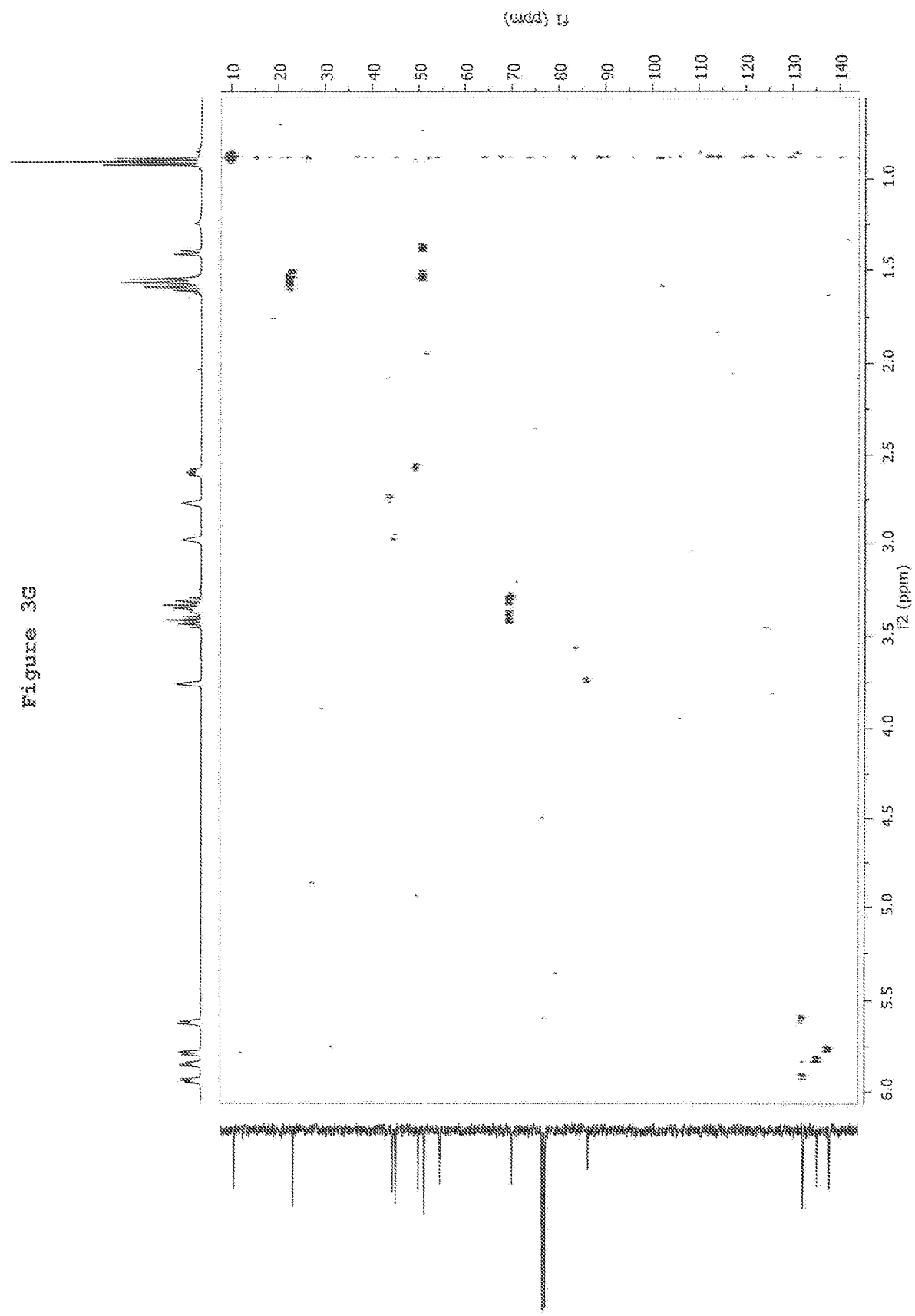
FIG. 3G provides a HMQC NMR spectrum of compound of Formula 3 in CDCl$_3$.

HMQC NMR spectrum of compound of Formula 3 in $CDCl_3$ is provided in FIG. 3G.

Following are the $^1$H— and $^{13}$C-NMR spectral data for compound of Formula 4:

$^1$H NMR (500 MHz, $CDCl_3$) δ 5.95 (dd, J=5.5, 2.9 Hz, 1H), 5.86 (dd, J=5.6, 3.0 Hz, 1H), 5.80 (d, J=5.7 Hz, 1H), 5.63 (d, J=5.7 Hz, 1H), 3.76 (d, J=1.7 Hz, 1H), 3.50-3.43 (m, 1H), 3.40-3.35 (m, 2H), 2.99 (s, 1H), 2.78 (s, 1H), 2.67-2.55 (m, 1H), 1.55 (dd, J=14.5, 7.3 Hz, 3H), 1.42 (d, J=8.1 Hz, 1H), 1.36-1.22 (m, 10H), 0.88 (t, J=6.9 Hz, 3H).

$^{13}$C NMR (126 MHz, CDCl$_3$) δ 138.24, 135.59, 132.56, 132.52, 86.64, 68.74, 54.86, 51.48, 50.19, 45.39, 44.69, 31.98, 30.30, 29.63, 29.41, 26.45, 22.81, 14.24.

Figure 4A:
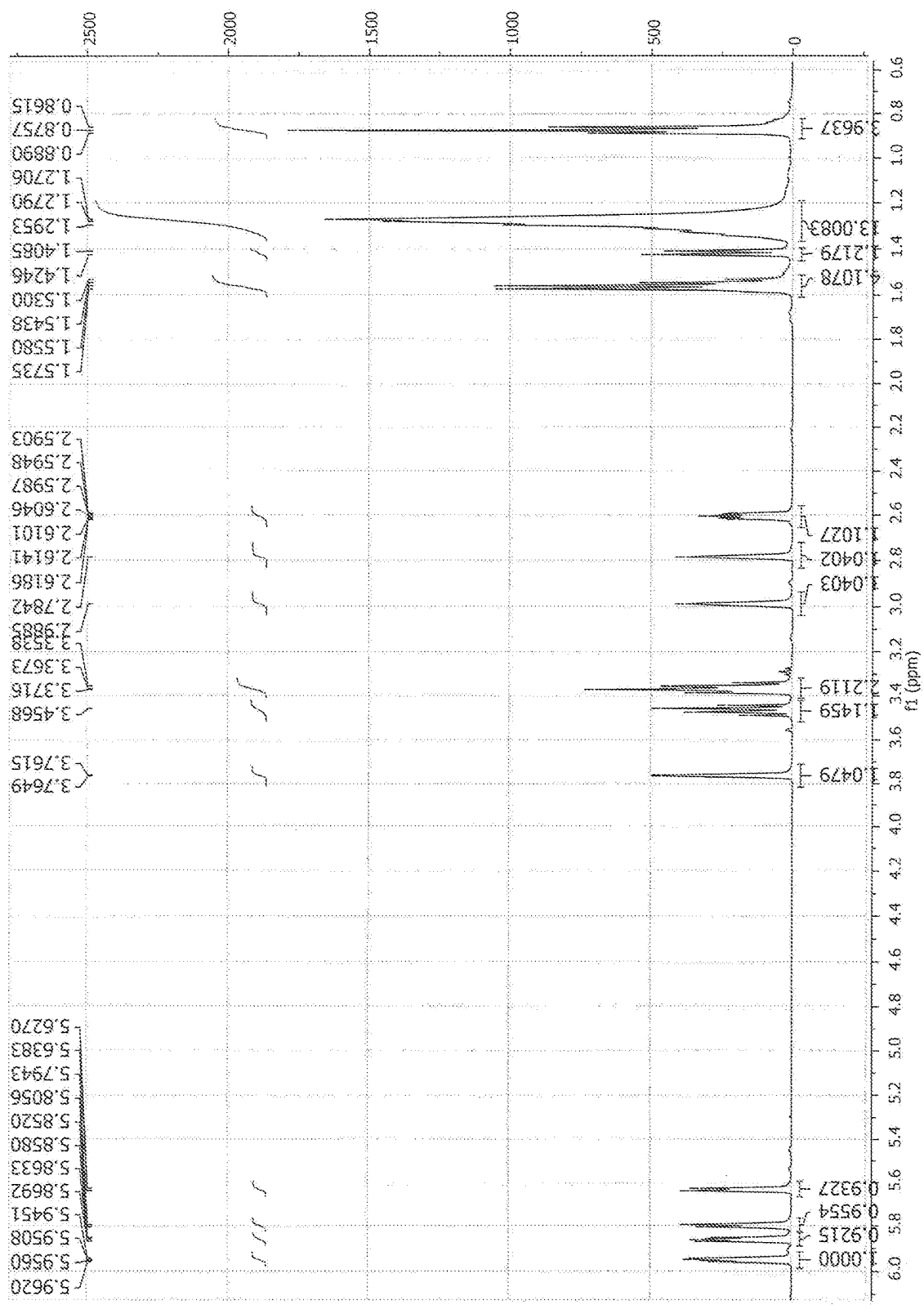
FIG. 4A shows a $^1$H-NMR spectrum of compound of Formula 4.
Figure 4B:
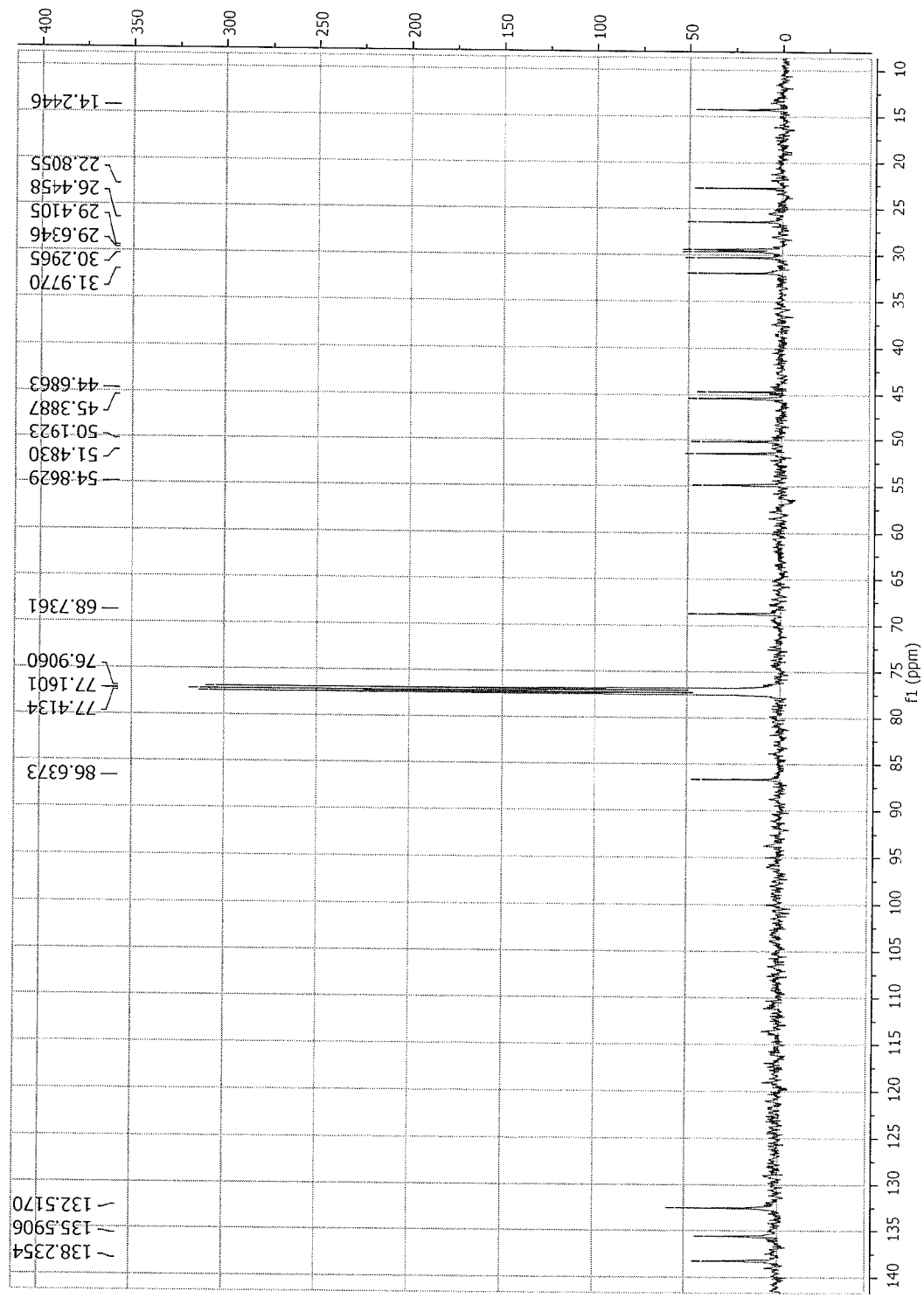
FIG. 4B shows a $^{13}$C-NMR spectrum of compound of Formula 4.

$^1$H— and $^{13}$C-NMR spectra for compound of Formula 4 are provided in FIGS. 4A and 4B, respectively.

Figure 4C:
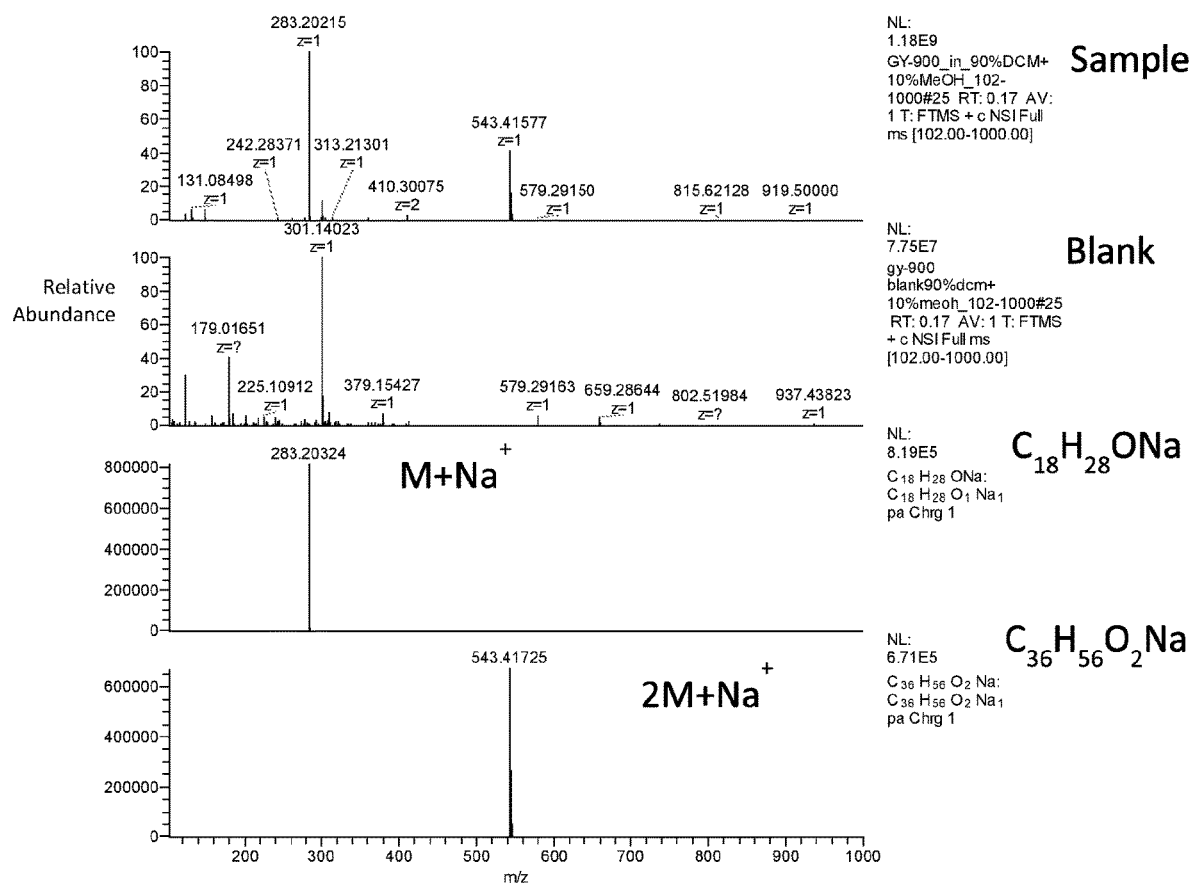
FIGS. 4C and 4D provide HRMS spectra for the sodium salt of compound of Formula 4.
Figure 4D:
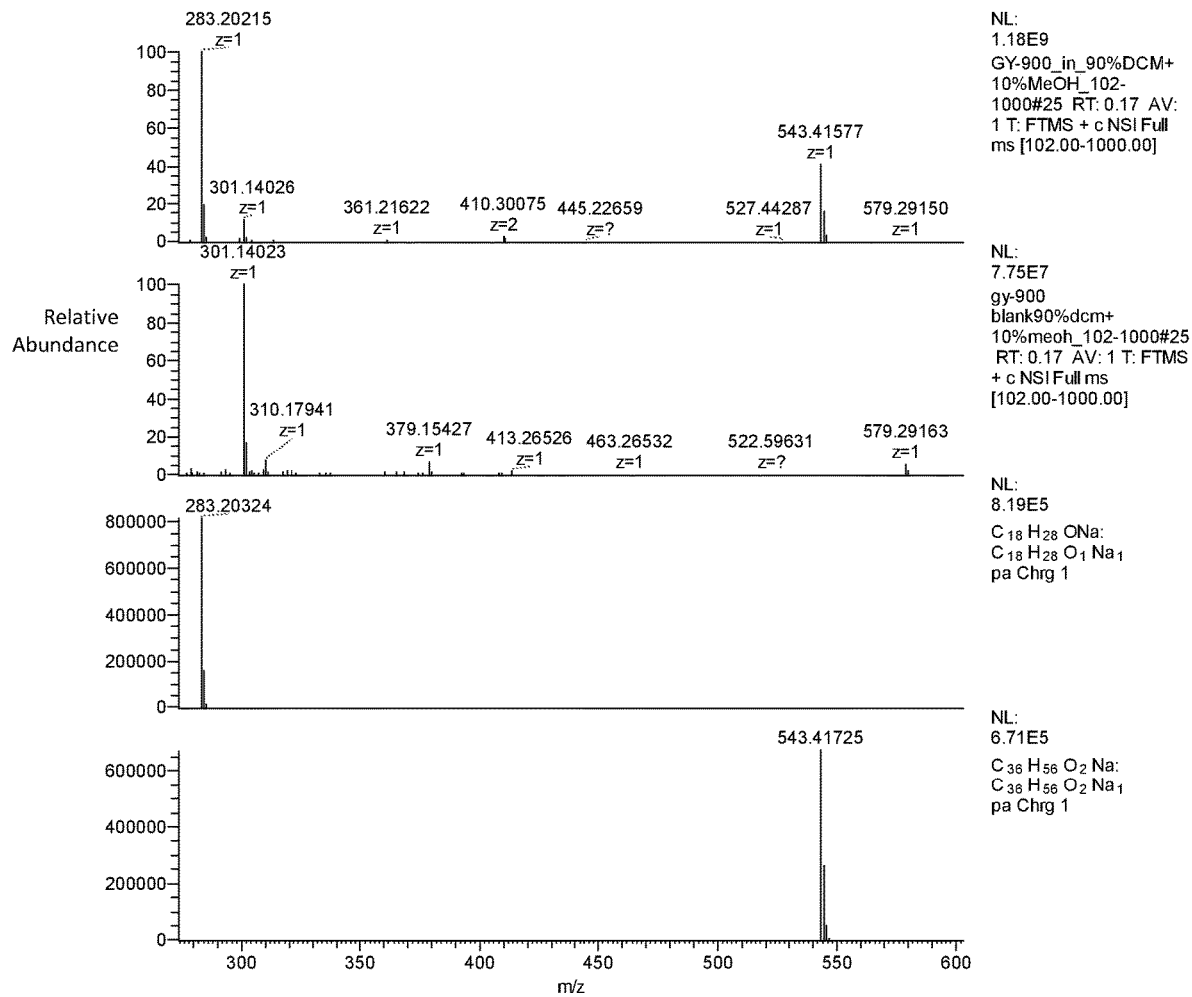

HRMS spectra for the sodium salt of compound of Formula 4 are provided in FIGS. 4C and 4D.

Figure 4E:
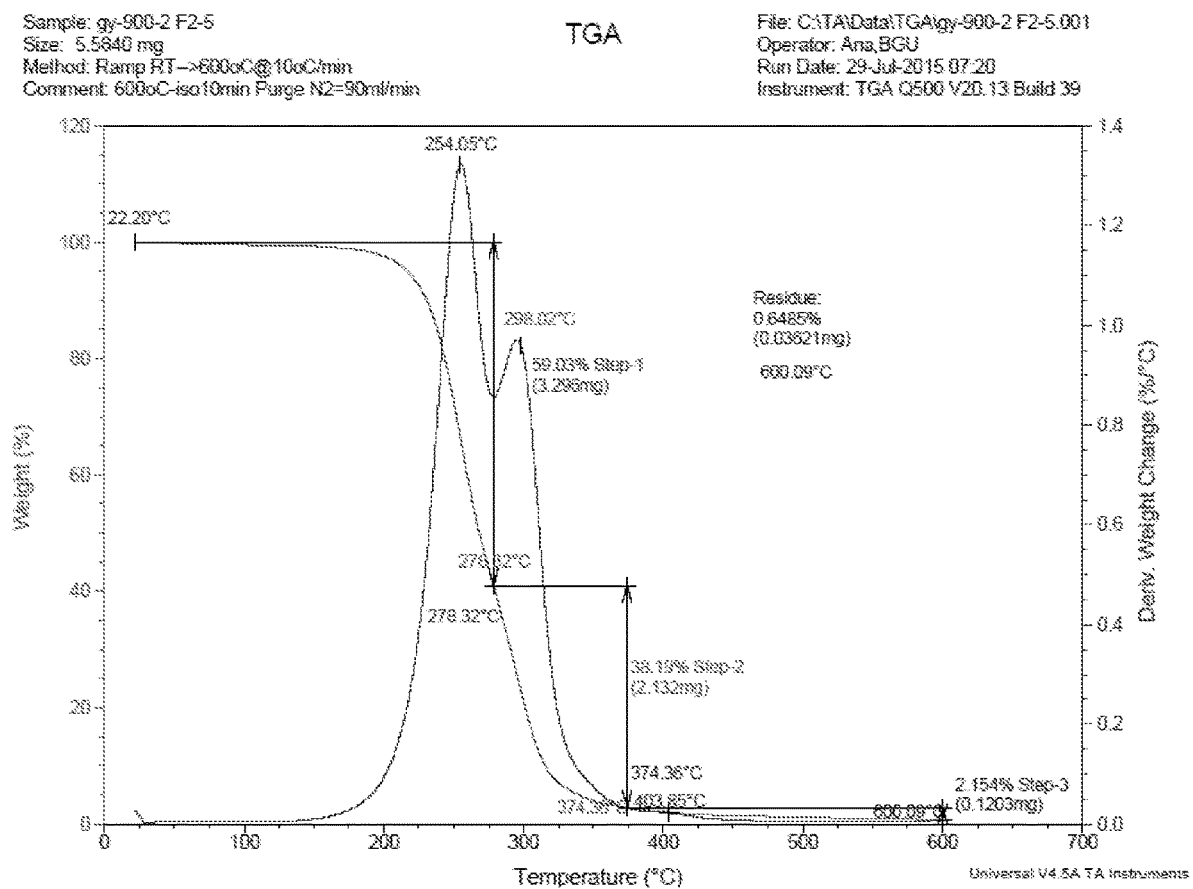
FIG. 4E provides a TGA curve of compound of Formula 4.

TGA curve of compound of Formula 4 is provided in FIG. 4E.

Figure 4F:
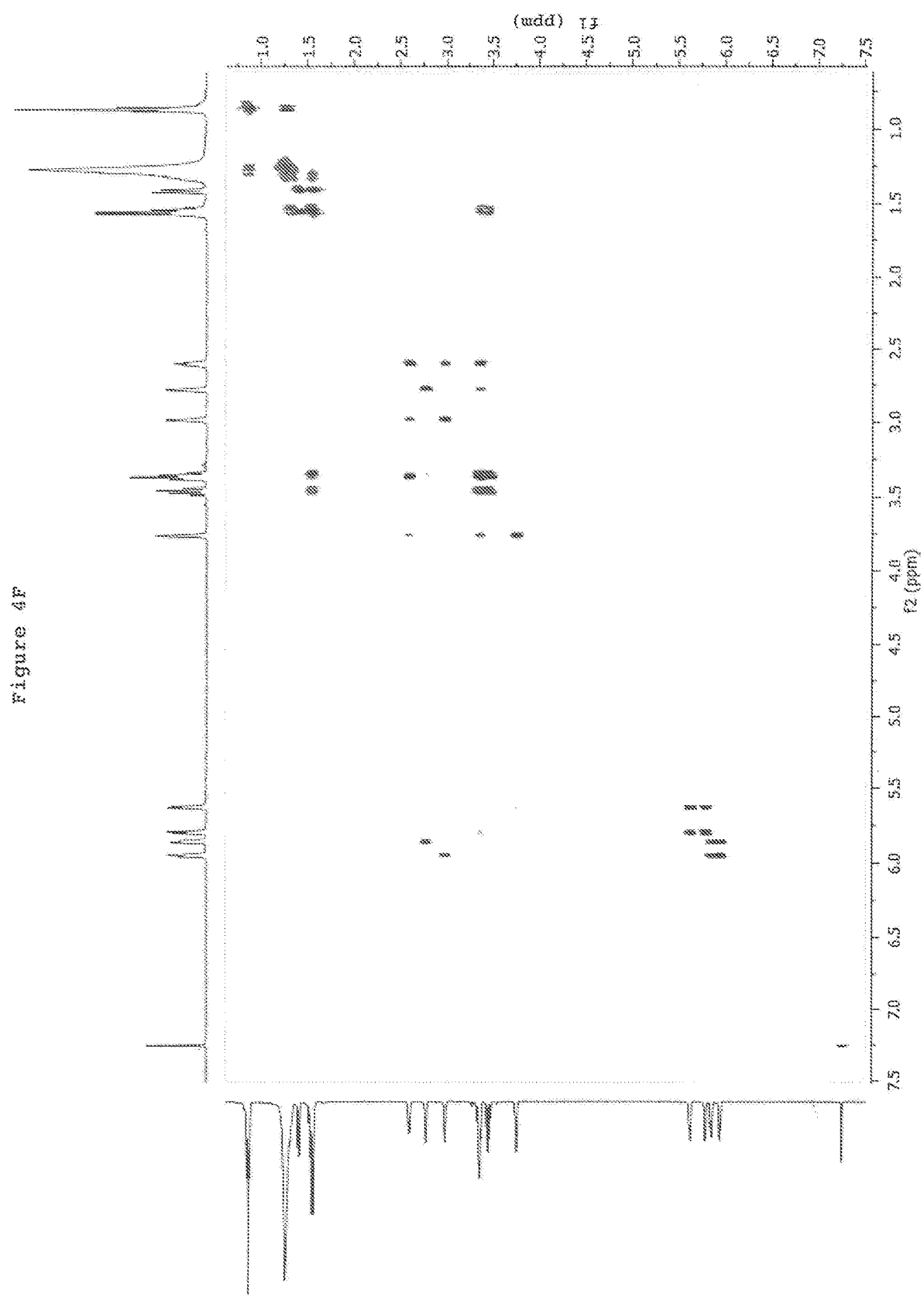
FIG. 4F provides a COSY NMR spectrum of compound of Formula 4 in CDCl$_3$.

COSY NMR spectrum of compound of Formula 4 in CDCl$_3$ is provided in FIG. 4F.

HMQC spectrum of compound of Formula 4 in CDCl$_3$ is provided in FIG. 4G.

Example 2

Preparation of Compound of Formula 5

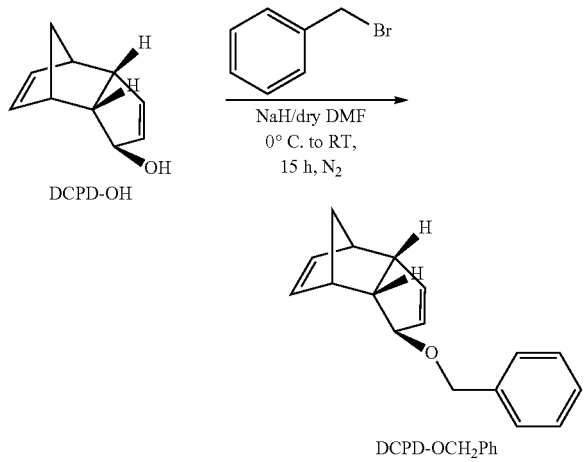

To a stirring suspension of NaH (421.5 mg, 17.57 mmol, hexane washed) in dry DMF (5 ml) under N$_2$, hydroxydicyclopentadiene (DCDP-OH, 2 gm, 13.5 mmol) was added in dropwise fashion after dissolving in dry DMF (5 ml). After 10 minutes vigorous stirring at room temperature (RT), temperature was lowered to 0° C. Then benzylbromide (2.06 ml, 17.56 mmol) was dropped into the stirring suspension. The purple suspension turned white with precipitation. It was left for 15 hours stirring by that time temperature raised to RT. The solution was then diluted with diethylether (100 ml) and washed with saturated NH$_4$Cl solution (50 ml×2). The organic layer was collected and dried over MgSO$_4$ and concentrated. Finally purification was done using diethylether/hexane (1:49, v/v) as mobile phase while silica gel was the stationary phase. The obtained product was colorless liquid. Yield: 2.63 gm (~81.3%).

Following are the $^1$H— and $^{13}$C-NMR spectral data for compound of Formula 5:

$^1$H NMR (CD$_2$Cl$_2$, δ ppm): 7.35 (4H, d), 7.28 (1H, m), 5.95 (1H, dd), 5.87 (1H, dd), 5.83 (1H, d), 5.66 (1H, d), 4.51 (2H, dd), 3.92-3.91 (1H, m), 3.42-3.37 (1H, m), 3.0 (1H, bs), 2.81 (1H, bs), 2.71-2.68 (1H, m), 1.58 (1H, d) and 1.45 (1H, d).

$^{13}$C NMR (CD$_2$Cl$_2$, δ ppm): 139.22, 138.12, 135.35, 132.39, 132.30, 128.21, 127.66, 27.28, 86.27, 70.22, 54.79, 51.25, 50.12, 45.25, 44.65.

Figure 5A:
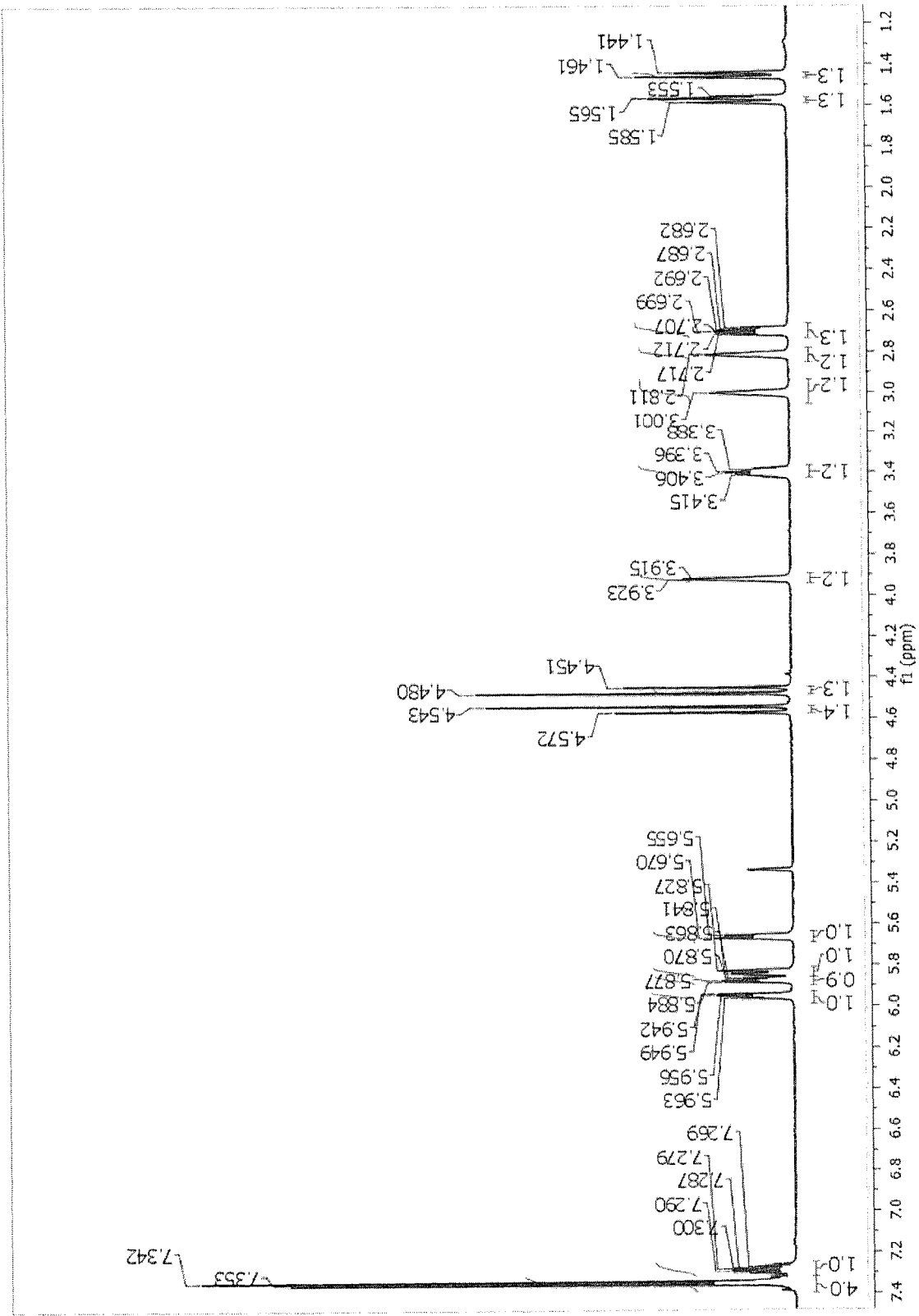
FIG. 5A shows a $^1$H-NMR spectrum of compound of Formula 5 in CD$_2$Cl$_2$.
Figure 5B:
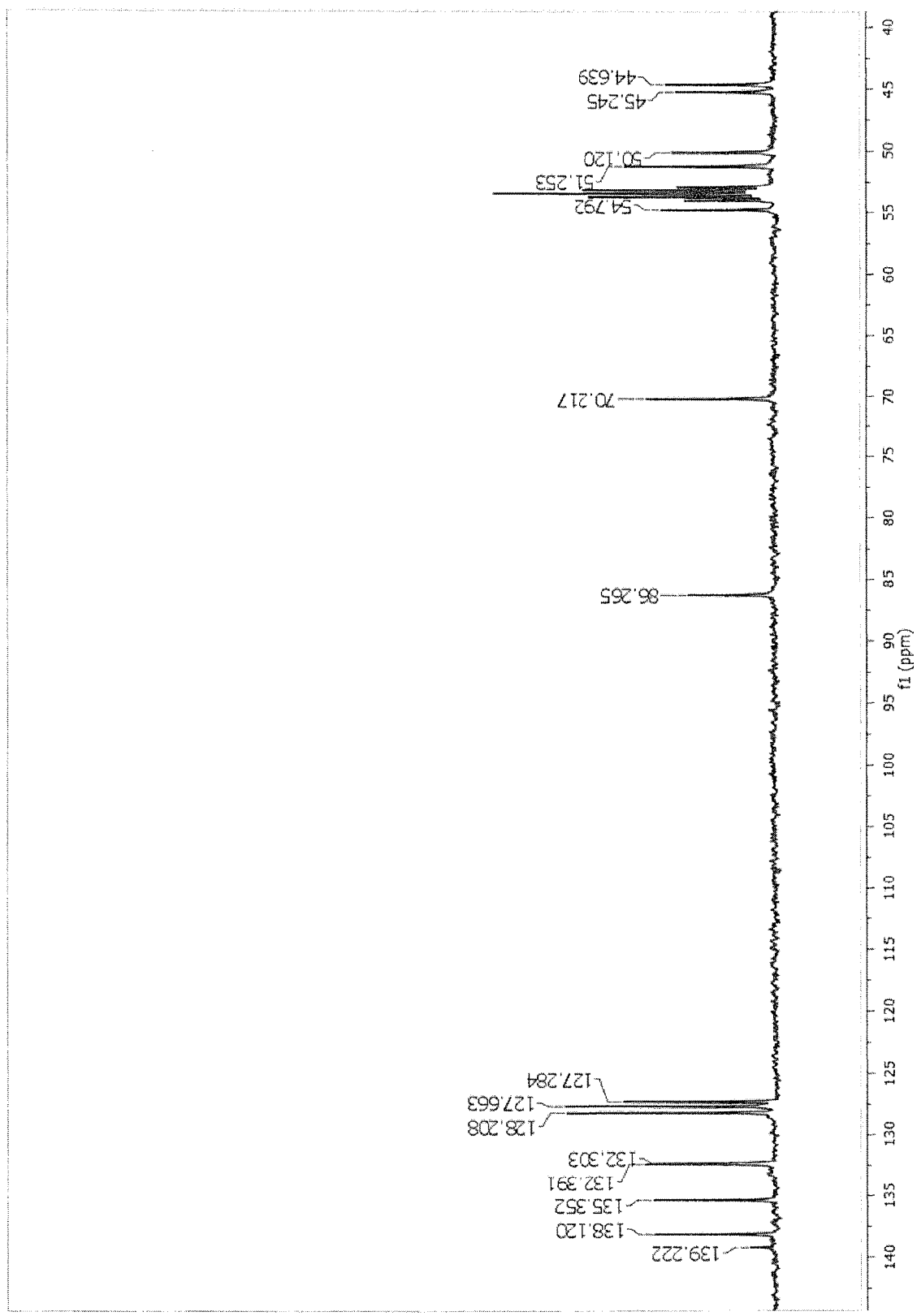
FIG. 5B shows a $^{13}$C-NMR spectrum of compound of Formula 5 in CD$_2$Cl$_2$.

$^1$H— and $^{13}$C-NMR spectra for compound of Formula 5 are provided in FIGS. 5A and 5B, respectively.

Example 3

Preparation of Compounds of Formulae 6, 7 and 8

Step 1

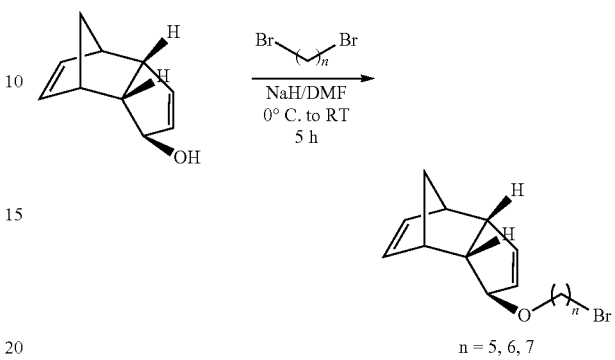

n = 5, 6, 7

To a stirring suspension of NaH (81 mg, 2.03 mmol, 60%) in dry DMF (1 ml) under inert atmosphere, hydroxy dicyclopentadiene (200 mg, 1.35 mmol) was added after dissolving in DMF (1 ml). The resultant reaction mixture was stirred for 10 minutes until it appeared as purple. It was then placed in an ice bath and then 1,n-dibromoalkane (n=5, 6, 7, 3.38 mmol) was added very slowly through syringe after dissolving in DMF (1 ml). The purple color disappeared. It was then left for 5 hours stirring at room temperature. Then it was diluted with diethyl ether (20 ml) and the organic layer was washed twice with NH$_4$Cl. The organic layer was then separated and dried over MgSO$_4$. Finally, it was concentrated and subjected to silica gel column chromatography for purification (2.5% diethyl ether in hexane) as colorless liquid.

Isolated yield: (n=5: 53%; n=6: 42%, n=7: 36%)

Step 2

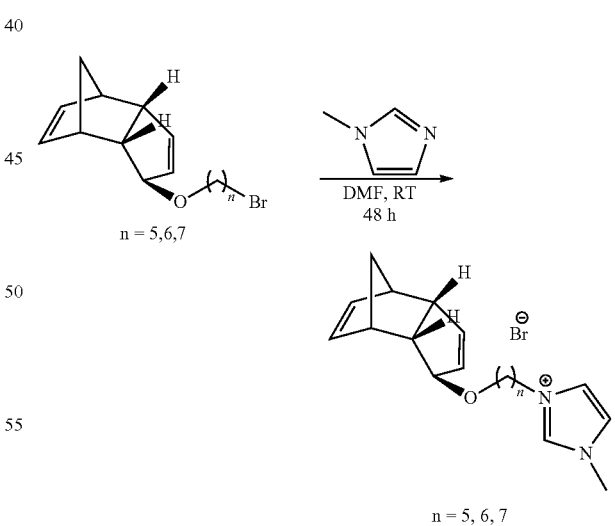

n = 5, 6, 7

To a stirring solution of the bromoalkoxy dicyclopentadiene (200 mg, 0.67 mmol) in DMF (1.5 ml, not dry), N-methyl imidazole (61 mg, 0.76 mmol) was added. The resultant solution was stirred at room temperature for 48 hours. Then solvent was removed under vacuum and it was washed with diethyl ether (5 times) to get a white gel in its pure form (yield: 98%).

Following are the $^1$H— and $^{13}$C-NMR spectral data for compound of Formula 6:

$^1$H NMR (CDCl$_3$, δ ppm, 400 MHz): 10.509 (1H, s), 7.356 (1H, s) 7.295 (1H, s), 5.949-5.929 (1H, q), 5.855-5.834 (1H, q), 5.797 (1H, d), 5.588 (1H, d), 4.331 (2H, t), 4.110 (3h, s), 3.740 (1H, s), 3.508-3.454 (1H, m), 3.386-3.333 (2H, m), 2.972 (1H, s), 2.780 (1H,$), 2.568-2.534 (1H, m), 1.942 (2H, quin), 1.639-1.551 (3H, m).

$^{13}$C NMR (CDCl$_3$, δ ppm, 100 MHz): 138.52, 138.22, 135.58, 132.50, 132.25, 123.31, 121.86, 86.78, 67.81, 54.85, 51.46, 50.19, 50.09, 45.34, 44.65, 36.91, 30.20, 29.41, 23.32.

Figure 6A:
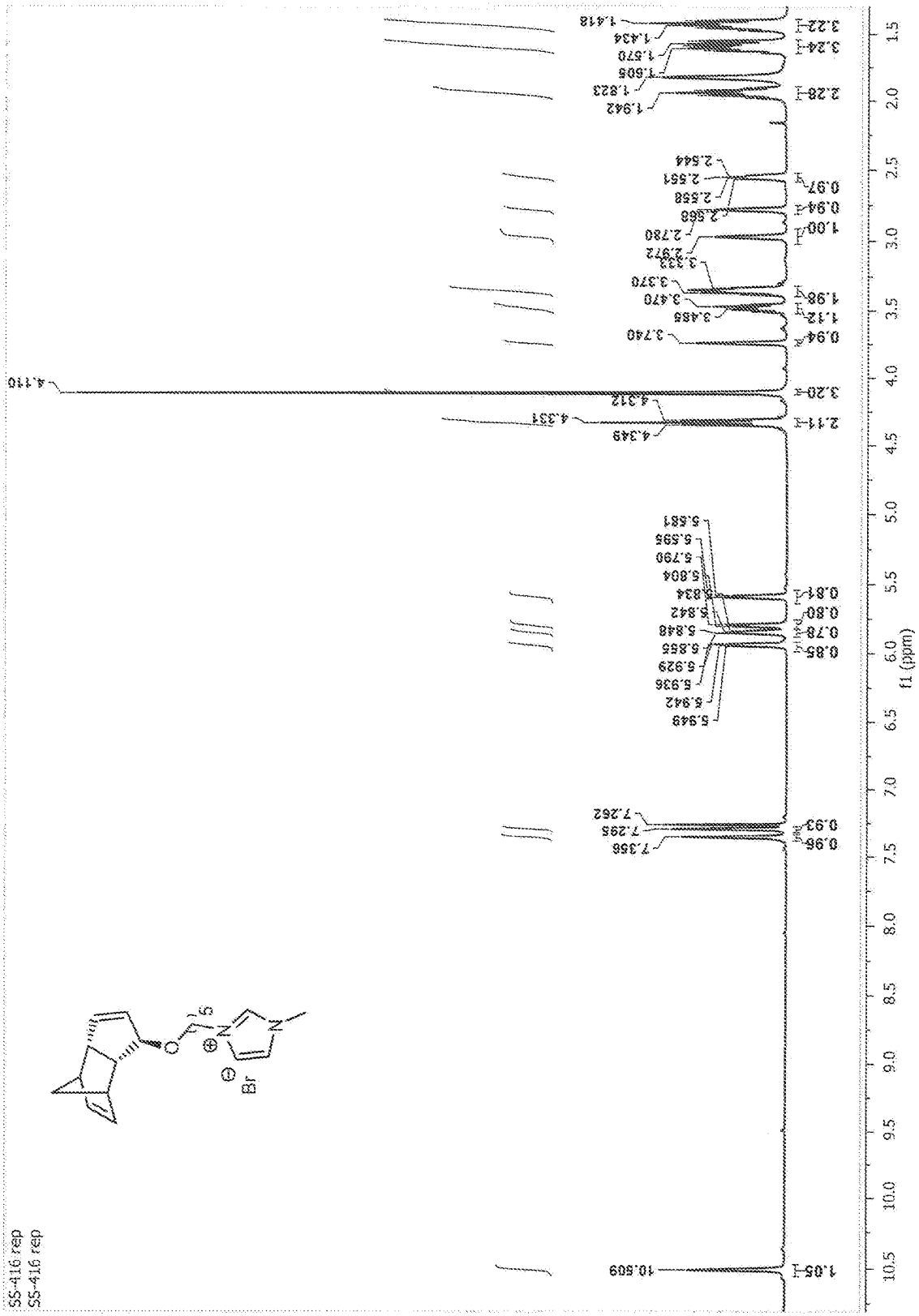
FIG. 6A shows a $^1$H-NMR spectrum of compound of Formula 6.
Figure 6B:
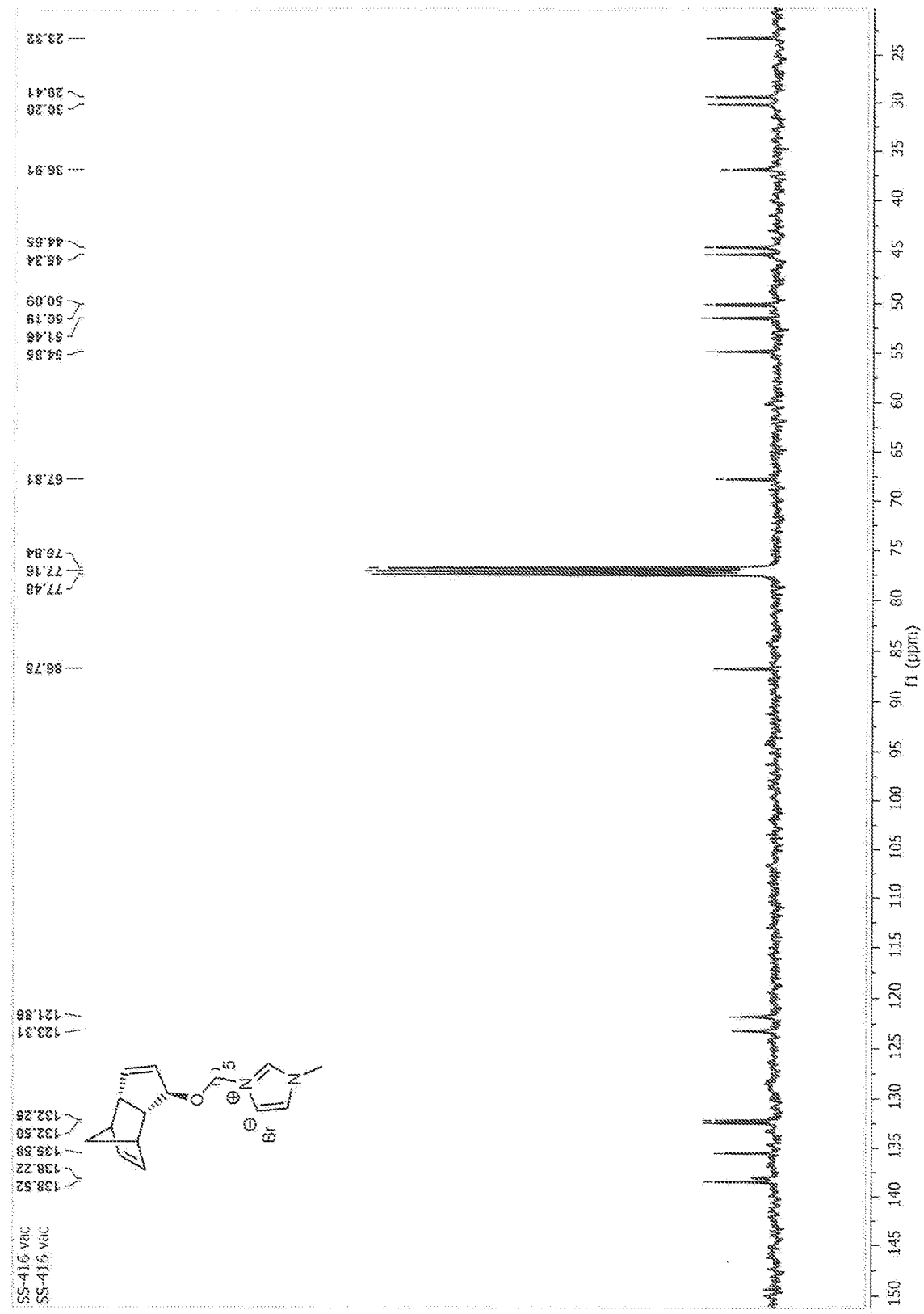
FIG. 6B shows a $^{13}$C-NMR spectrum of compound of Formula 6.

$^1$H— and $^{13}$C-NMR spectra for compound of Formula 6 are provided in FIGS. 6A and 6B, respectively.

Figure 6C:
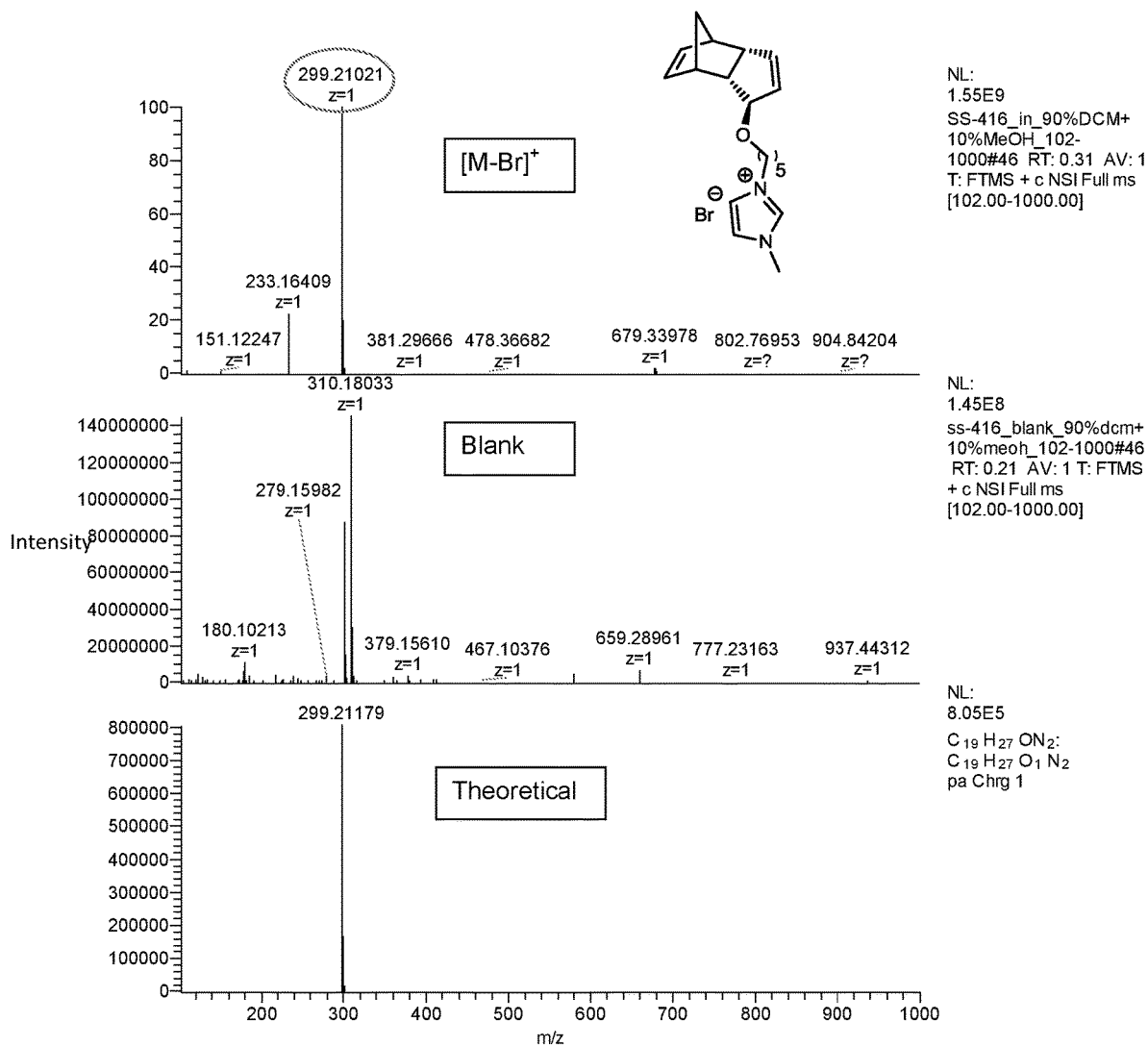
FIG. 6C shows a HRMS spectrum of compound of Formula 6.

HRMS spectra for compound of Formula 6 are provided in FIG. 6C.

Following are the $^1$H— and $^{13}$C-NMR spectral data for compound of Formula 7:

$^1$H NMR (CDCl$_3$, δ ppm, 400 MHz): 10.509 (1H, s), 7.399 (1H, s), 7.304 (1H, s), 5.946-5.926 (1H, q), 5.851-5.830 (1H, q), 5.787 (1H, d), 5.592 (1H, d), 4.309 (1H, t), 4.112 (3H, s), 3.736 (1H, s), 3.481-3.426 (1H, m), 3.365-3.312 (2H, m), 2.970 (1H, s), 2.771 (1H, s), 2.577-2.542 (1H. m), 1.933-1.879 (3H, m), 1.558-1.504 (2H, m), 1.412-1.370 (5H, m).

$^{13}$C NMR (CDCl$_3$, δ ppm, 100 MHz): 138.29, 137.96, 135.45, 132.40, 132.22, 123.25, 121.65, 86.59, 68.02, 54.72, 51.34, 50.11, 50.00, 45.23, 44.53, 35.80, 30.20, 29.82, 26.08, 25.75.

Figure 7A:
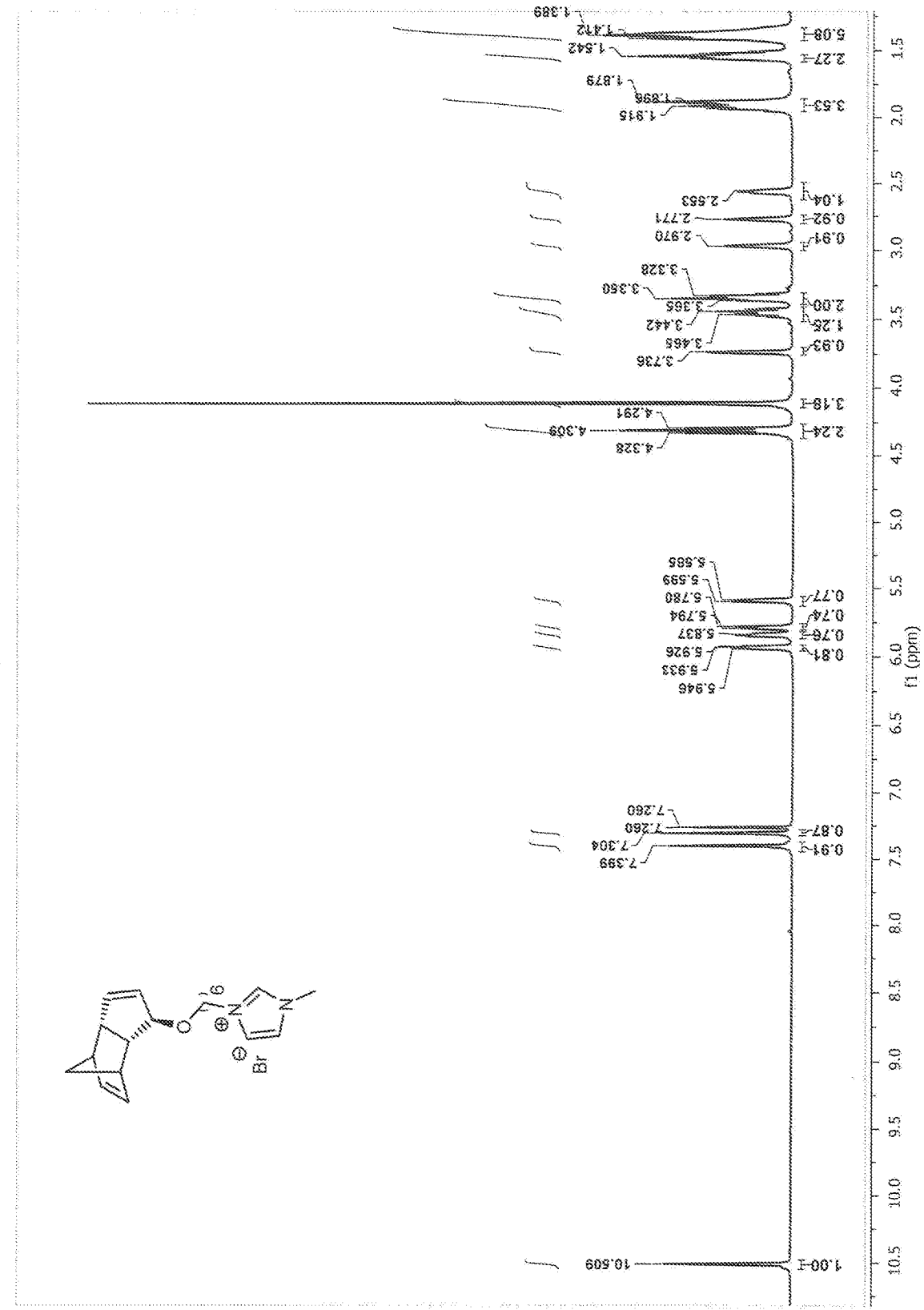
FIG. 7A provides a $^1$H-NMR spectrum of compound of Formula 7.
Figure 7B:
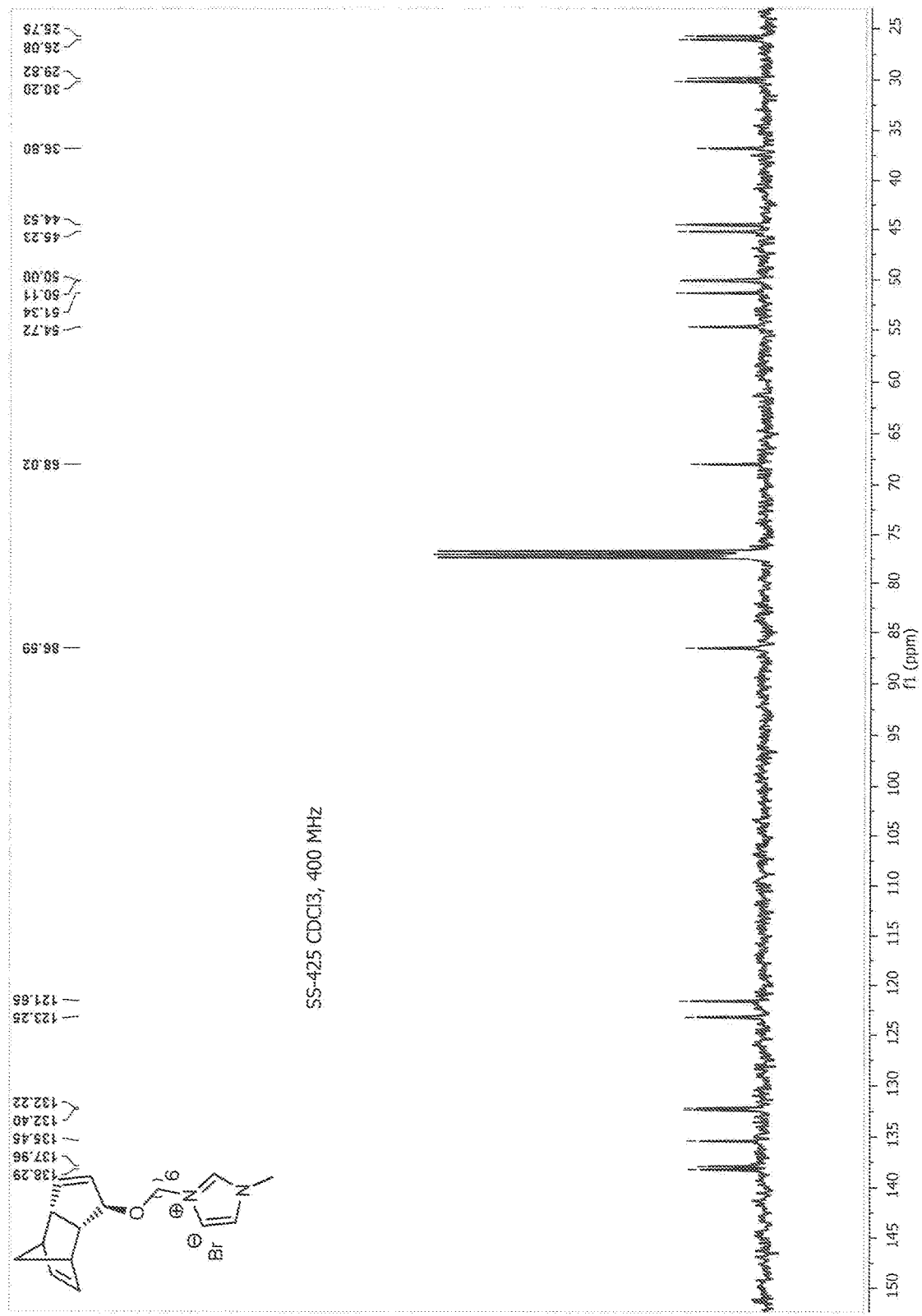
FIG. 7B provides a $^{13}$C-NMR spectrum of compound of Formula 7.

$^1$H— and $^{13}$C-NMR spectra for compound of Formula 7 are provided in FIGS. 7A and 7B, respectively.

Following are the $^1$H— and $^{13}$C-NMR spectral data for compound of Formula 8:

$^1$H NMR (CDCl$_3$, δ ppm, 400 MHz): 10.755 (1H, s), 7.224 (1H, s), 7.194 (1H, s), 5.961-5.941 (1H, q), 5.867-5.845 (1H, q), 5.801 (1H, d), 5.634 (1H, d), 4.316 (2H, t), 4.123 (3H, s), 3.753 (1H, s), 3.491-3.436 (1H, m), 3.377-3.322 (2H, m), 2.985 (1H, s), 2.784 (1H, s), 2.601-2.566 (1H, m), 1.922 (2H, broad s), 1.576-1.523 (3H, m), 1.415 (1H, d), 1.360 (6H, broad s).

$^{13}$C NMR (CDCl$_3$, δ ppm, 100 MHz): 138.24, 138.20, 135.46, 132.41, 132.27, 123.07, 121.53, 86.57, 68.28, 54.73, 51.51, 50.24, 50.02, 45.24, 44.54, 36.81, 30.20, 29.94, 28.81, 26.15, 26.08.

Figure 8A:
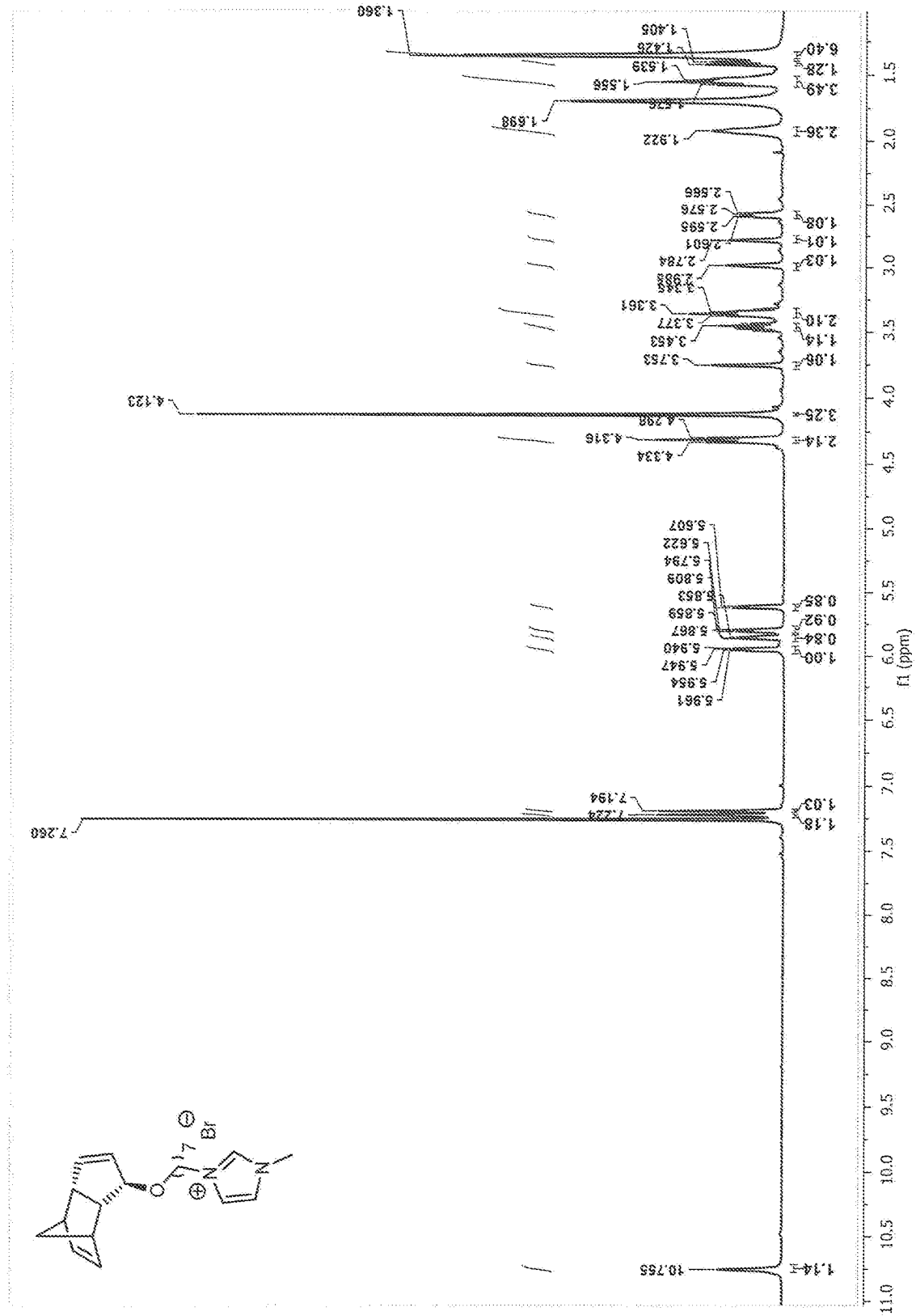
FIG. 8A shows a $^1$H-NMR spectrum of compound of Formula 8.
Figure 8B:
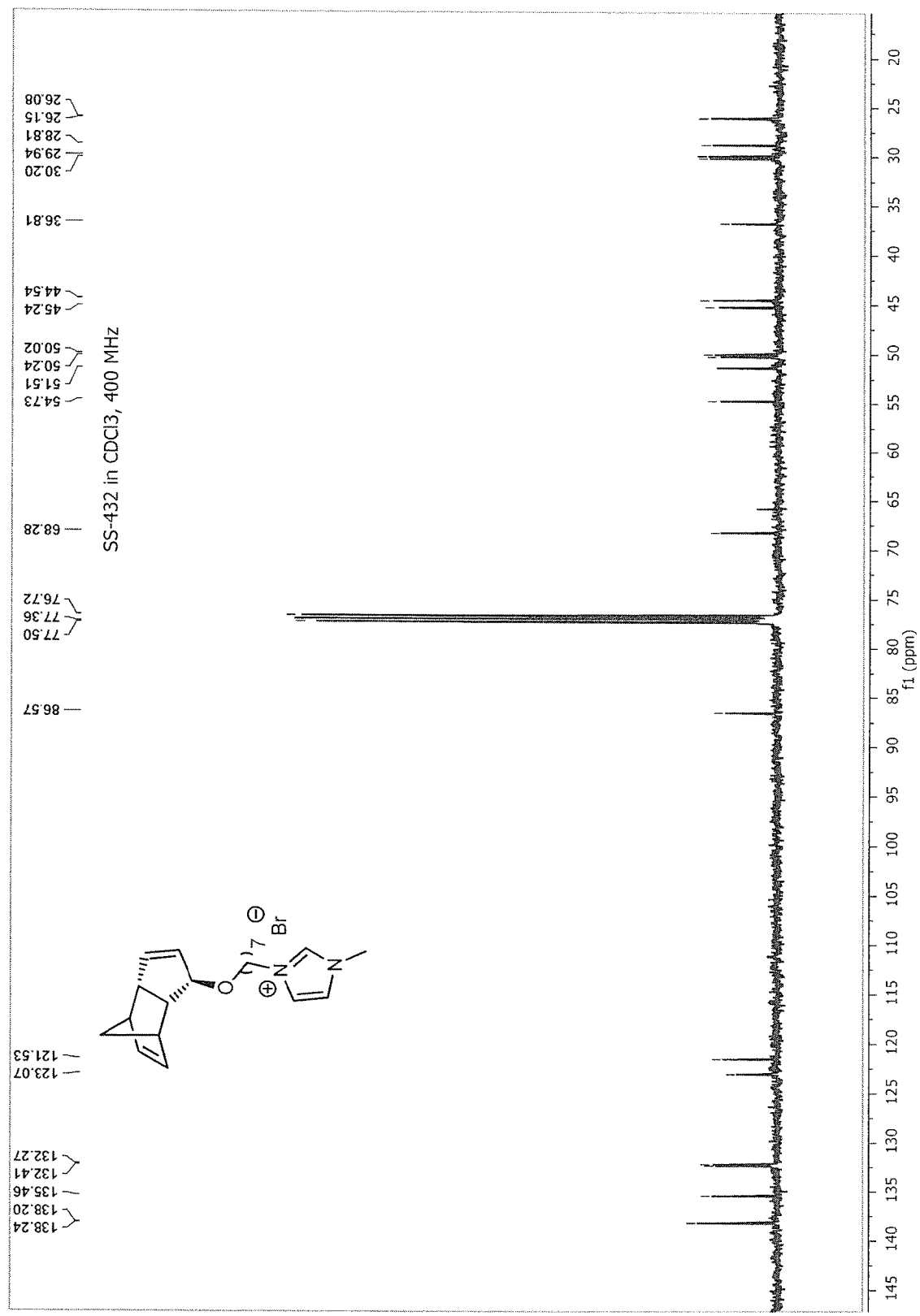
FIG. 8B shows a $^{13}$C-NMR spectrum of compound of Formula 8.

$^1$H— and $^{13}$C-NMR spectra for compound of Formula 8 are provided in FIGS. 8A and 8B, respectively.

Example 4

Preparation of Compound of Formula 9

Step 1

Step 1 was carried out as described in detail in Step 1 of Example 3 above.

Step 2

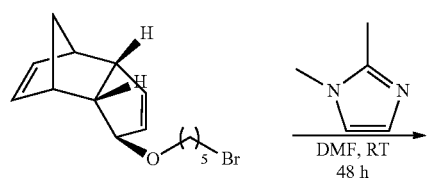

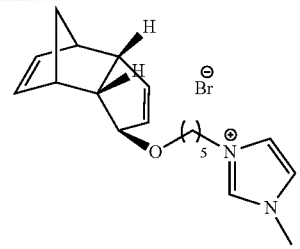

To a stirring solution of the bromoalkoxy dicyclopentadiene (360 mg, 1.22 mmol) in DMF (1.5 ml, not dry), 1,2-dimethylmethyl imidazole (175 mg, 1.82 mmol) was added. The resultant solution was stirred at room temperature for 48 hours. Then solvent was removed under vacuum and it was washed with diethyl ether (5 times) to get a white solid in its pure form (yield: 87%) [Melting point: 30°-35° C.].

Following are the $^1$H— and $^{13}$C-NMR spectral data for compound of Formula 9:

$^1$H NMR (CDCl$_3$, δ ppm, 400 MHz): 10.468 (1H, s), 7.304 (1H, s), 7.251 (1H, s), 5.941-5.920 (1H, dd), 5.847-5.782 (1H, dd), 5.789 (1H, d), 5.58 (1H, d), 4.322 (3H, t), 4.096 (3H,$), 3.732 (1H,$), 3.486-3.448 (1H, m), 3.379-3.326 (2H, m), 2.963 (1H, s), 2.772 (1H, s), 2.560-2.526 (1H, m), 1.990-1.895 (2H, m), 1.631-1.543 (3H, m), 1.465-1.389 (3H, m).

$^{13}$C NMR (CDCl$_3$, δ ppm, 100 MHz): 138.39, 137.85, 135.46, 132.38, 132.13, 123.26, 121.79, 86.65, 67.69, 54.72, 51.33, 49.97, 45.22, 44.52, 36.79, 30.20, 29.30, 23.19.

Figure 9A:
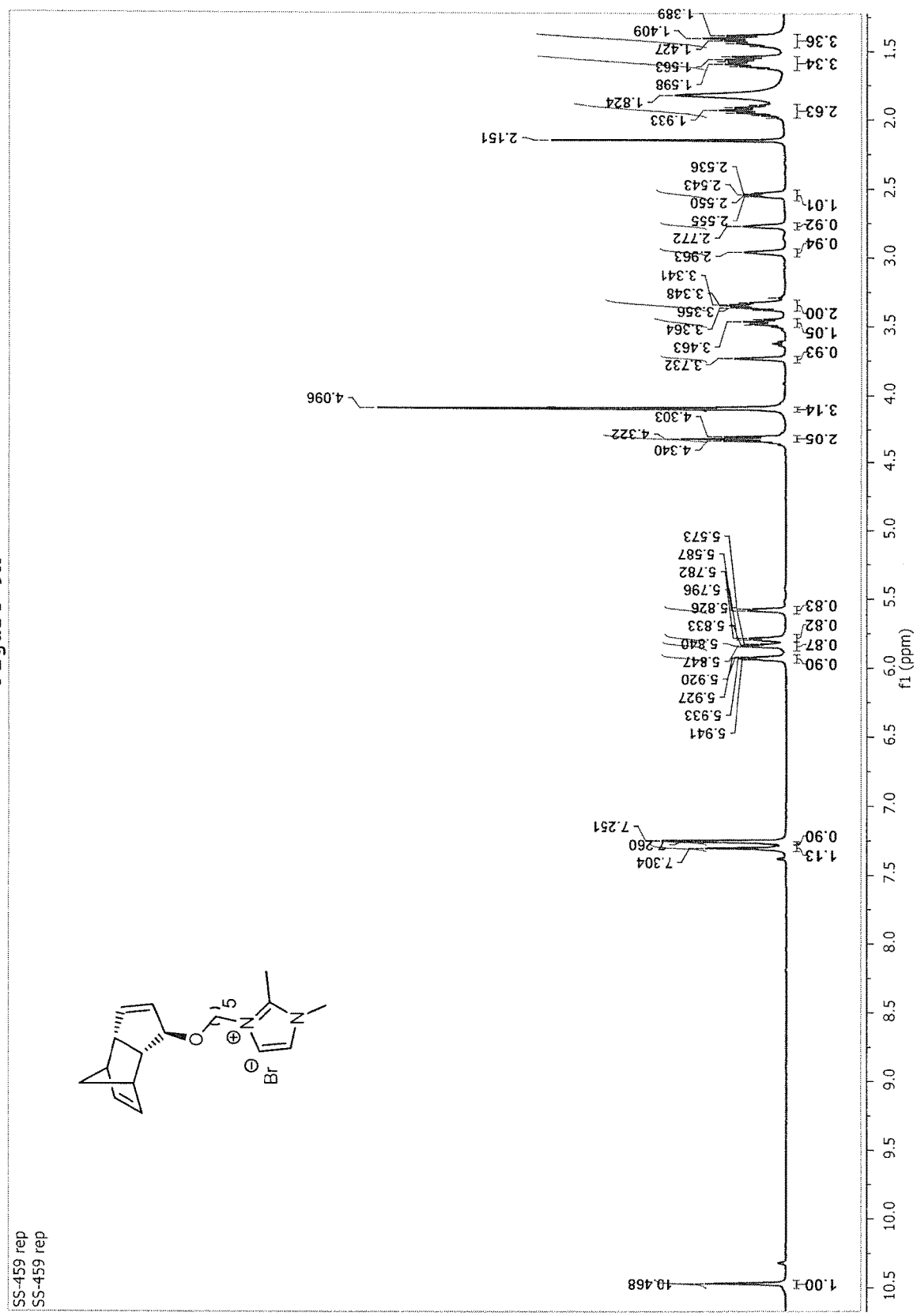
FIG. 9A provides a $^1$H-NMR spectrum of compound of Formula 9.
Figure 9B:
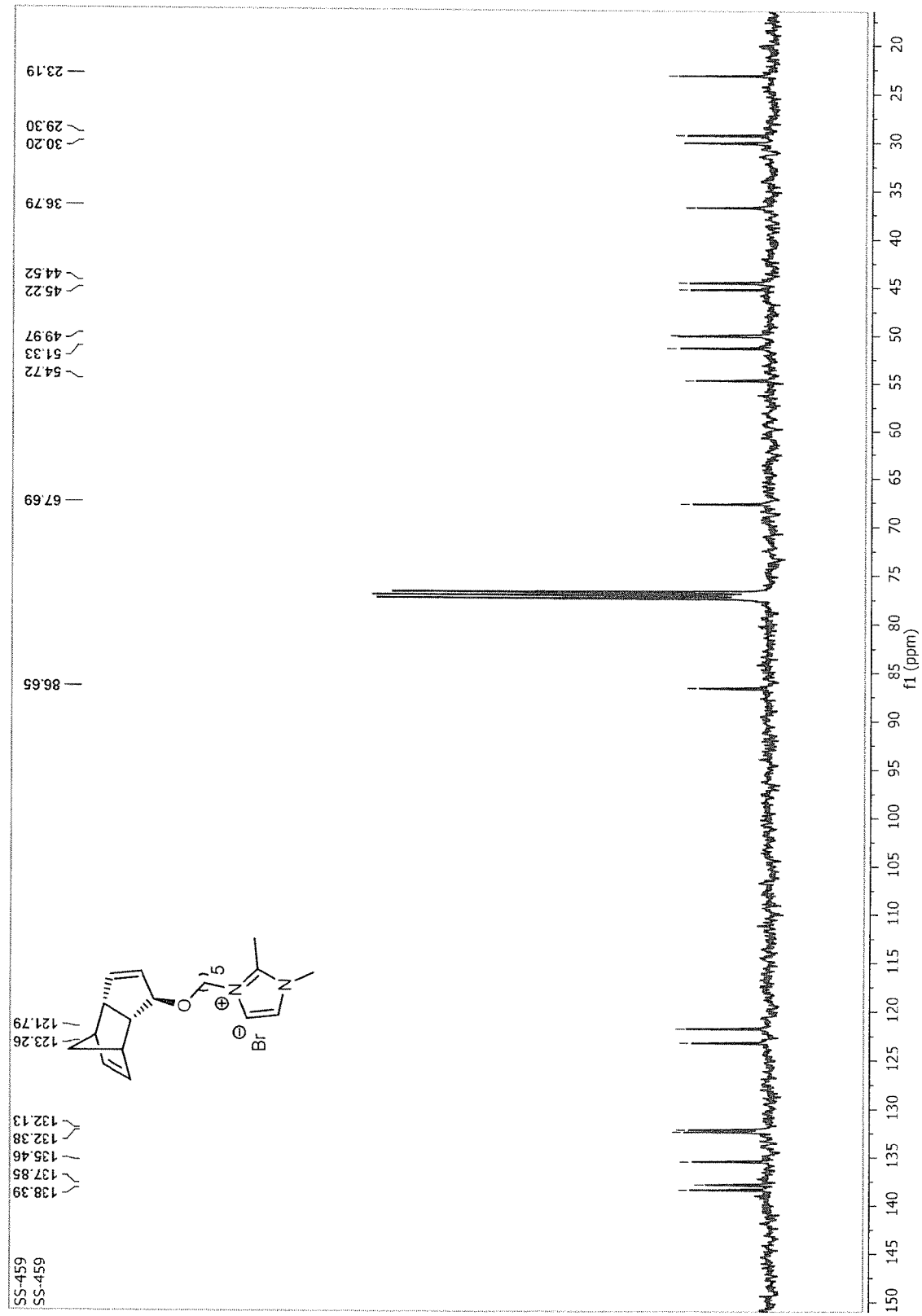
FIG. 9B provides a $^{13}$C-NMR spectrum of compound of Formula 9.

$^1$H— and $^{13}$C-NMR spectra for compound of Formula 9 are provided in FIGS. 9A and 9B, respectively.

Example 5

Preparation of Compound of Formula 10

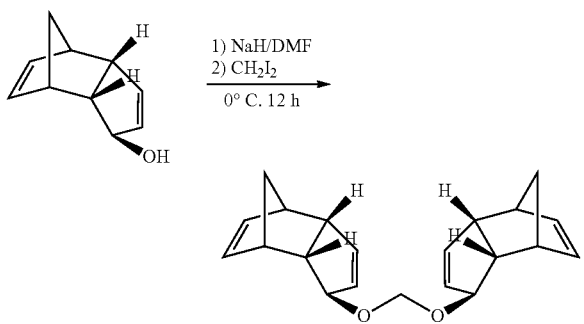

In a 3-necked RB-flask, hydroxydicyclopentadiene (400 mg, 1 eq) and NaH (162 mg, 1.5 eq) were dissolved in dry dimethylformamide (DMF) at 0° C. under nitrogen atmosphere. After stirring for 10 minutes diiodomethane (0.326 ml, 1.5 eq) was added in one portion and stirred overnight. Ethylacetate was added, washed with aqueous NH$_4$Cl solution, organic layer was collected, dried on MgSO$_4$, filtered and evaporated. Purified by silica gel chromatography with 5% ethyl acetate in petroleum ether.

Isolated Yield: 82 mg.

Following are the ¹H-NMR spectral data for compound of Formula 10:

¹H NMR (400 MHz, CDCl$_3$) δ 5.91 (d, J=41.6 Hz, 4H), 5.82 (t, J=6.3 Hz, 2H), 5.62 (dd, J=12.2, 5.4 Hz, 2H), 4.85-4.70 (m, 2H), 4.08 (s, 2H), 3.39 (s, 2H), 3.01 (s, 2H), 2.80 (s, 2H), 2.65 (s, 2H), 1.57 (s, 2H), 1.42 (t, J=6.6 Hz, 2H).

Figure 10:
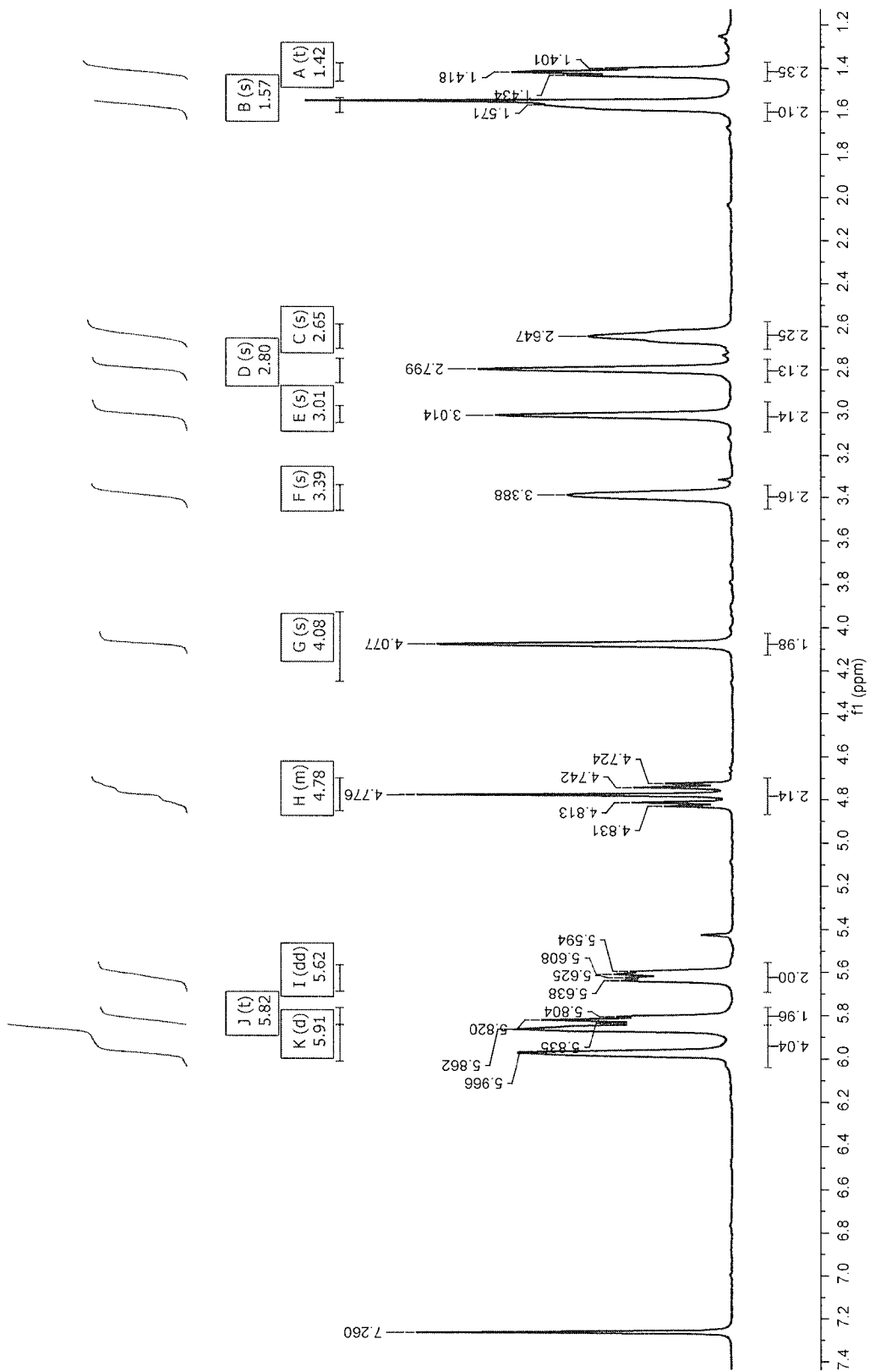
FIG. 10 provides a $^1$H-NMR spectrum of compound of Formula 10.

¹H-NMR spectrum for compound of Formula 10 is provided in FIG. 10.

Example 6

Preparation of Compound of Formula 11
(DCPD-OBz)

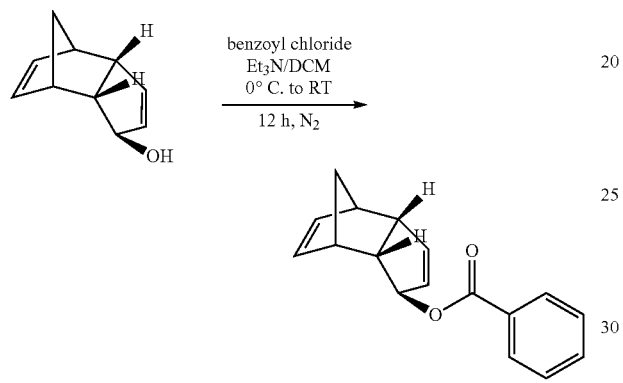

A three necked round bottom flask was charged with hydroxydicyclopentadiene (1 gm, 6.75 mmol), was subjected to vacuum and then nitrogen, consecutively three times. Then, dry DCM (50 ml) and Et3N (1.5 ml) were added and the reaction mixture was stirred at 0° C. for 10 minutes. After that, benzoyl chloride (727 μl, 10.13 mmol) was added through syringe in drop wise fashion. The reaction mixture was then kept for 12 hours stirring at room temperature. After that, it was washed with water. The organic layer was then separated and dried over MgSO$_4$. It was finally concentrated and subjected to flash column chromatography for purification. The expected product was eluted with Ethyl acetate/Petroleum ether (1:19) on silica gel stationary phase as a light yellowish liquid.

Isolated Yield: 1.04 gm (~81%)

Compound of formula 11 is solid with M.P. at 70° C.

Following are the ¹H— and ¹³C-NMR spectral data for compound of Formula 11:

¹H NMR (500 MHz, CDCl$_3$) δ 8.03 (dd, J=8.1, 0.9 Hz, 2H), 7.54 (t, J=7.4 Hz, 1H), 7.42 (t, J=7.7 Hz, 2H), 6.11 (dd, J=5.6, 3.0 Hz, 1H), 5.95 (d, J=5.7 Hz, 1H), 5.91 (dd, J=5.6, 3.0 Hz, 1H), 5.70 (d, J=5.7 Hz, 1H), 5.27-5.17 (m, 1H), 3.48-3.40 (m, 1H), 3.19 (s, 1H), 2.86 (s, 1H), 2.80-2.73 (m, 1H), 1.63 (d, J=8.2 Hz, 1H), 1.44 (d, J=8.2 Hz, 1H).

¹³C NMR (126 MHz, CDCl$_3$) δ 166.83, 140.28, 135.57, 132.89, 132.83, 131.00, 130.82, 129.69, 128.41, 82.90, 77.41, 77.16, 76.91, 54.84, 51.57, 50.55, 45.00, 44.93.

Figure 11A:
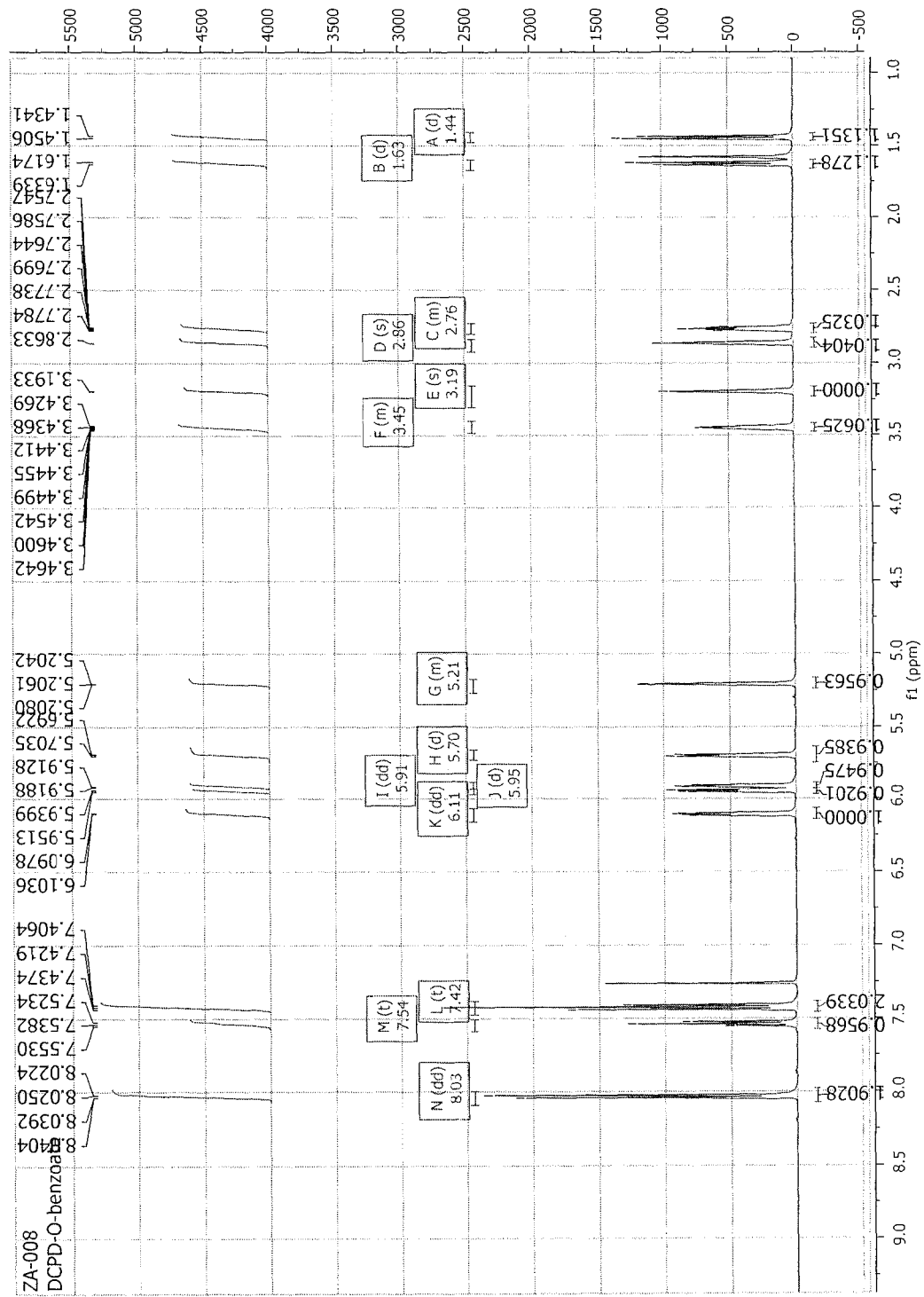
FIG. 11A shows a $^1$H-NMR spectrum of compound of Formula 11.
Figure 11B:
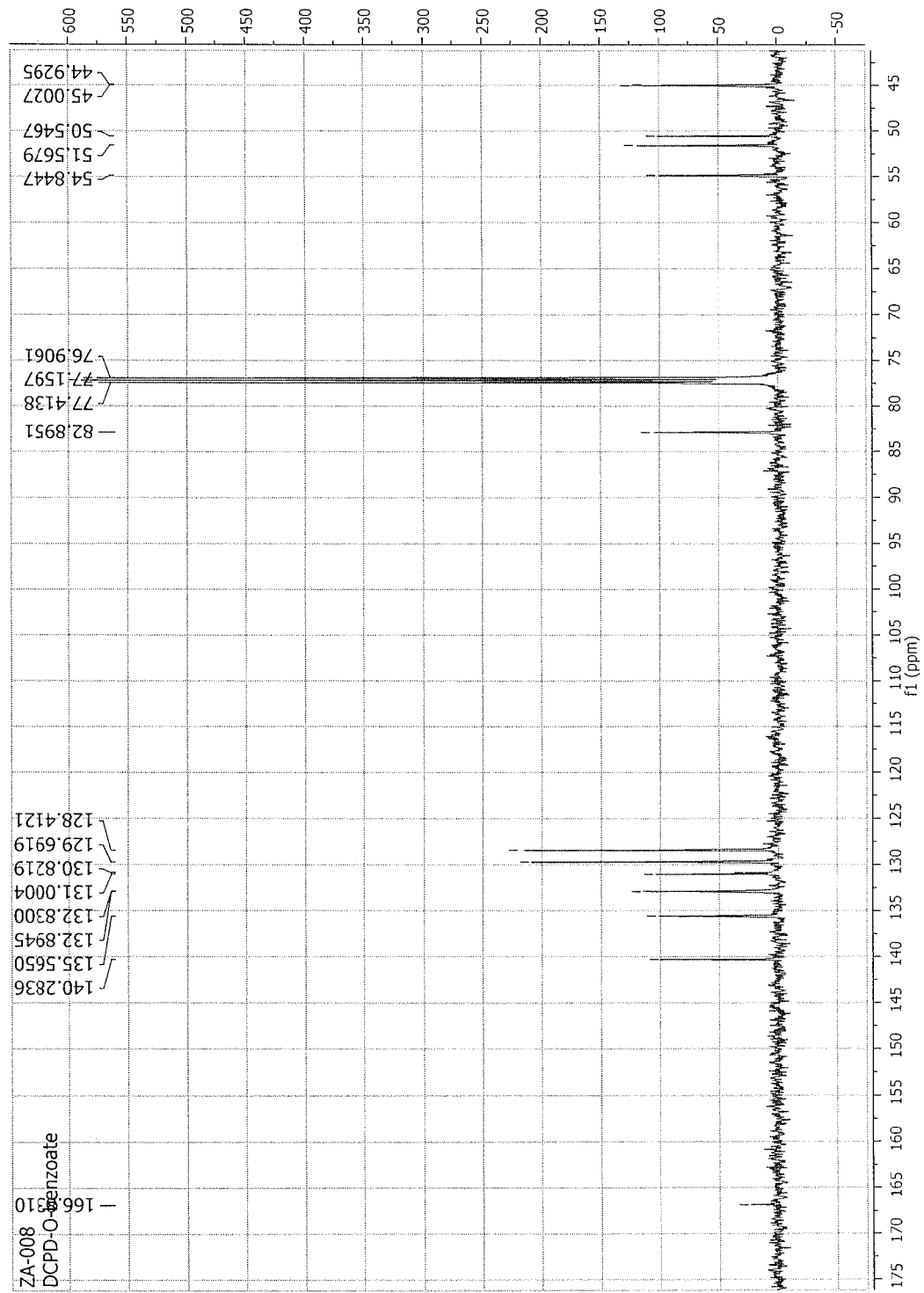
FIG. 11B shows a $^{13}$C-NMR spectrum of compound of Formula 11.

¹H— and ¹³C-NMR spectra for compound of Formula 11 are provided in FIGS. 11A and 11B, respectively.

Figure 11C:
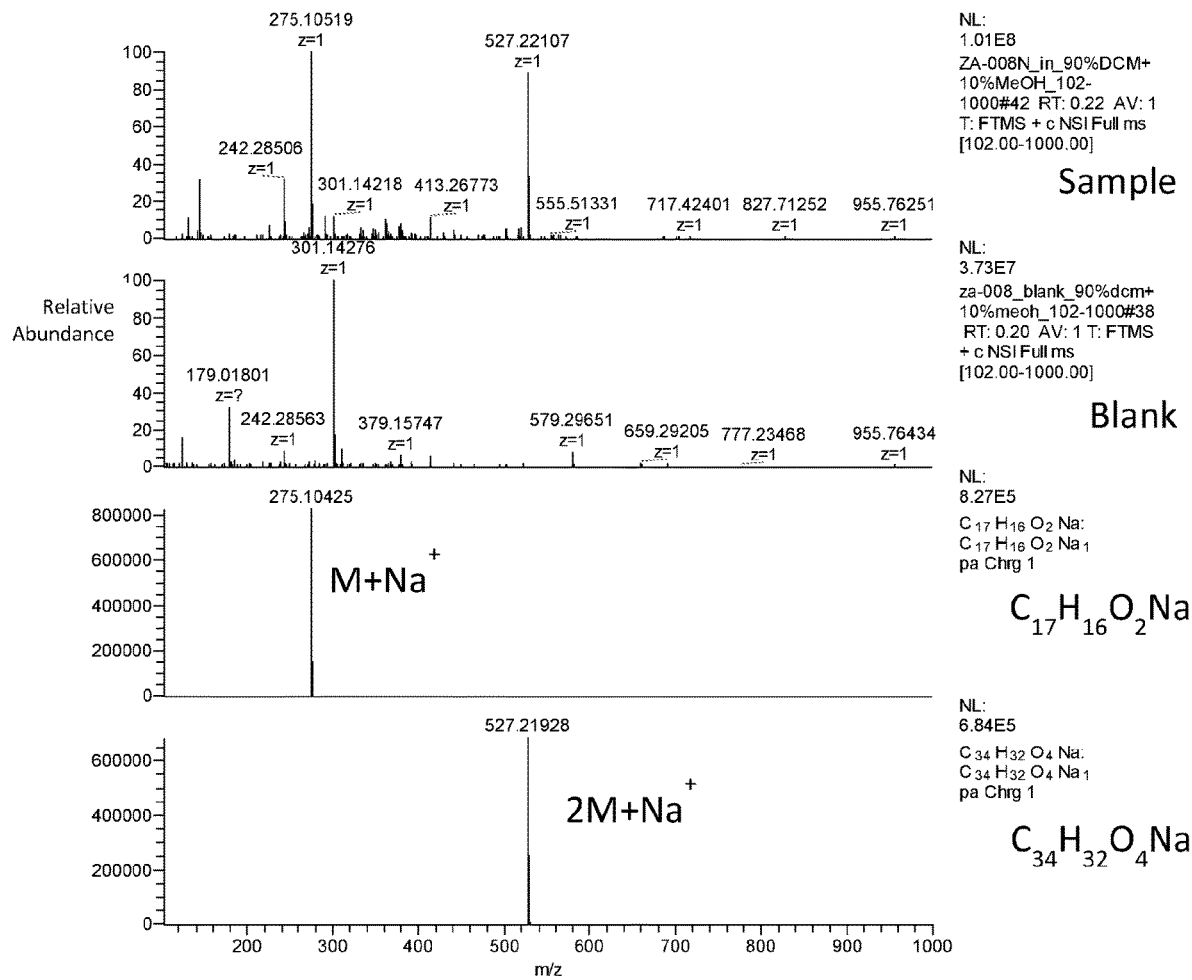
FIGS. 11C and 11D show HRMS spectra of the sodium salt of compound of Formula 11.
Figure 11D:
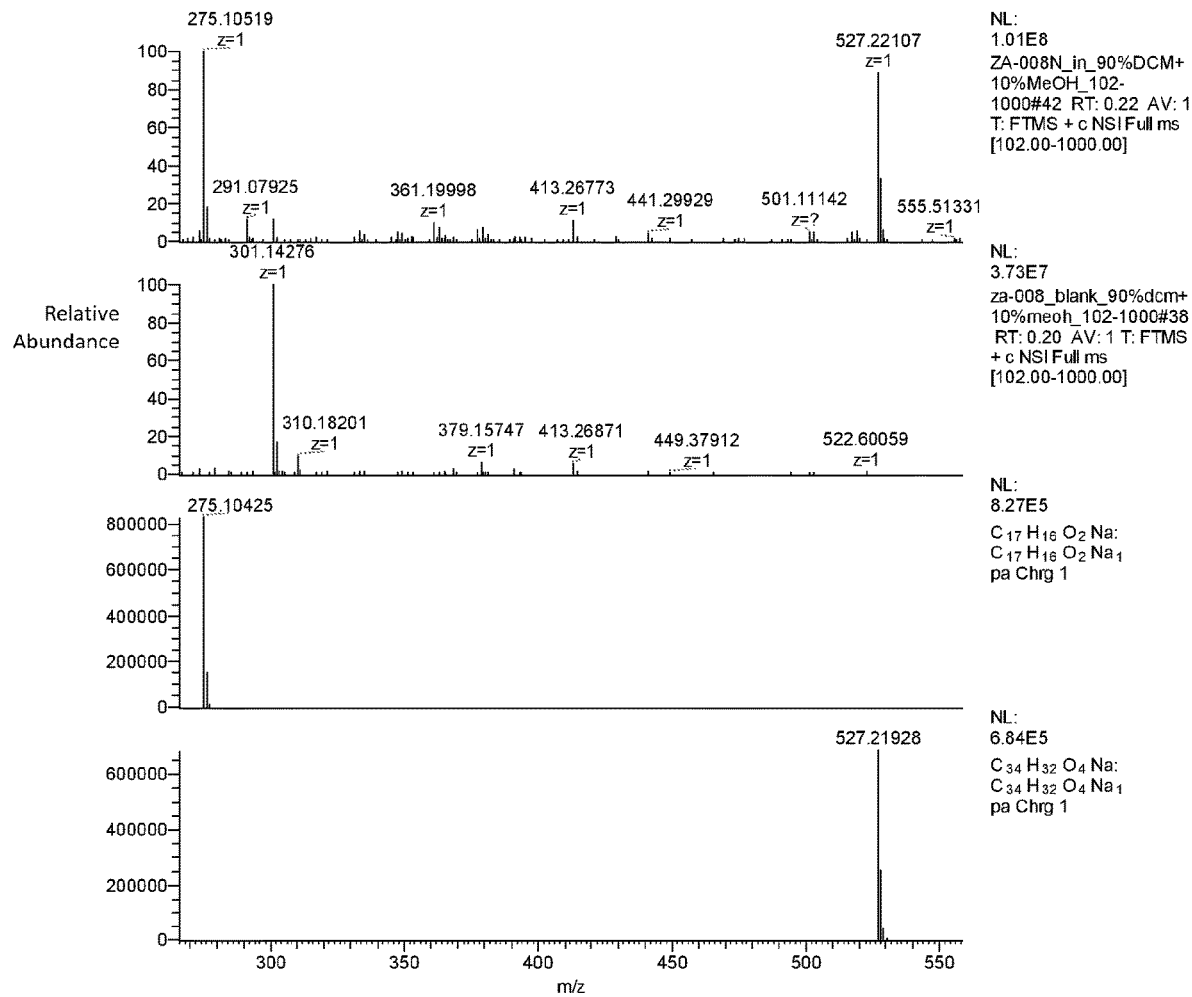

HRMS spectra for the sodium salt of compound of Formula 11 are provided in FIGS. 11C and 11D.

Figure 11E:
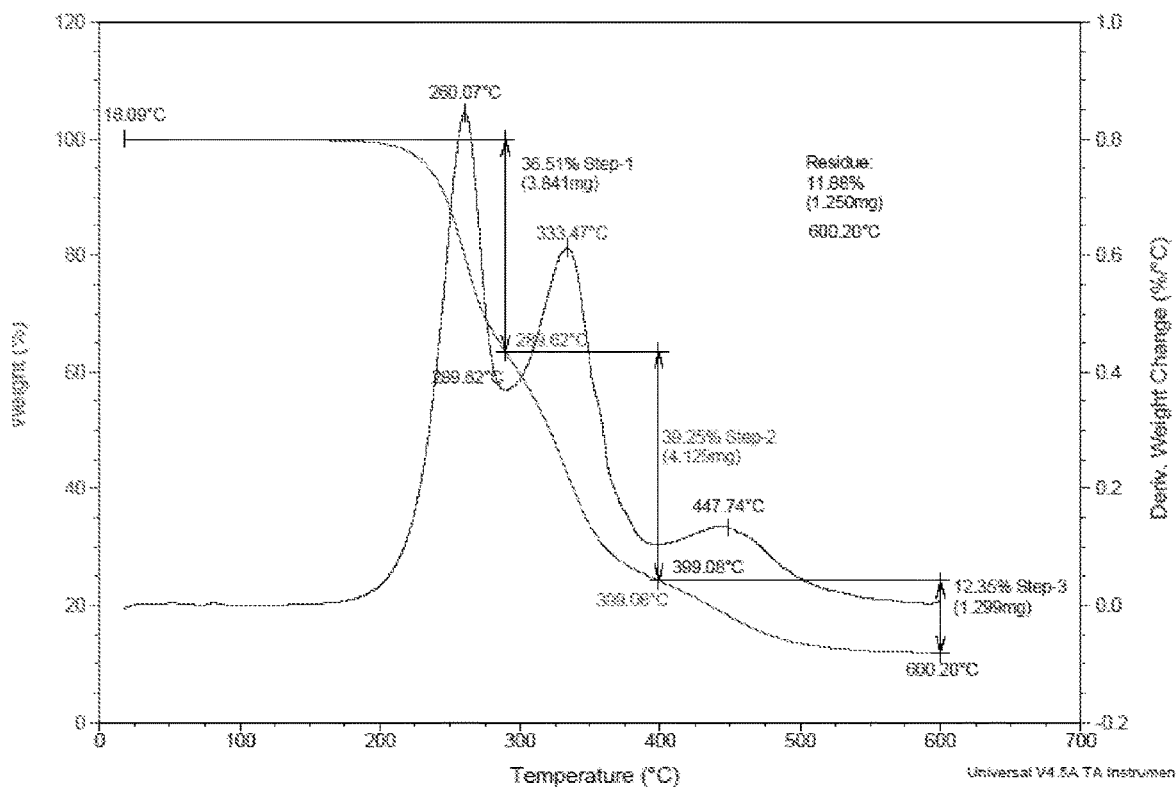
FIG. 11E provides a TGA curve of compound of Formula 11.

TGA curve of compound of Formula 11 is provided in FIG. 11E.

Example 7

Preparation of Compound of Formula 12

Step 1

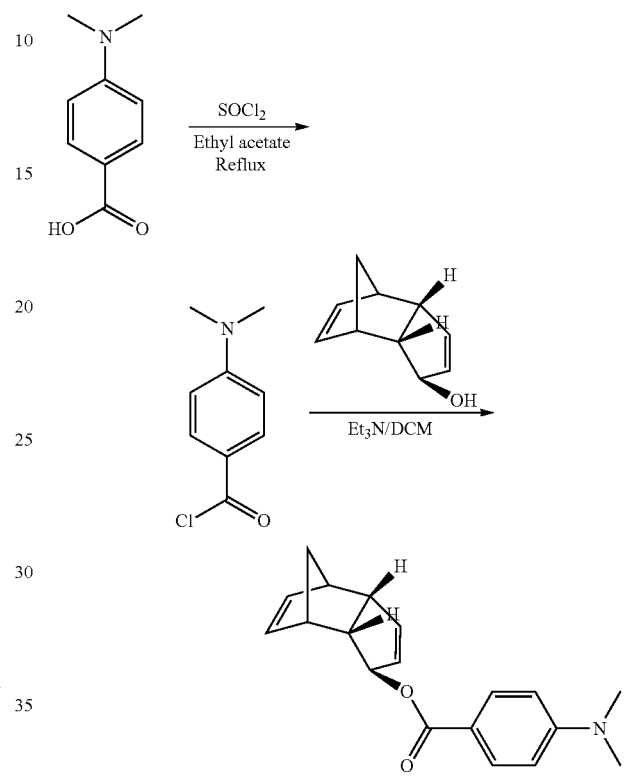

To the suspension of N,N-dimethylamino benzoic acid (500 mg, 3.02 mmol) in EtOAc, thionyl chloride (540 mg, 4.52 mmol) was added and it was kept under reflux under inert conditions for 10 hours until a clear yellow solution was observed. The solvent was removed after cooling to room temperature and the obtained yellow solid was immediately dissolved in dry dichloromethane (20 ml). Then hydroxydicyclopentadiene (400 mg, 2.7 mmol) was dissolved in dry dichloromethane (10 ml) containing Et3N (1 ml) and was added into the acid chloride solution at room temperature and was left for overnight stirring. Then the solvent was removed and the ester product was purified by silica gel column chromatography using 5% EtOAc in hexane (Isolated yield: 50%).

Step 2

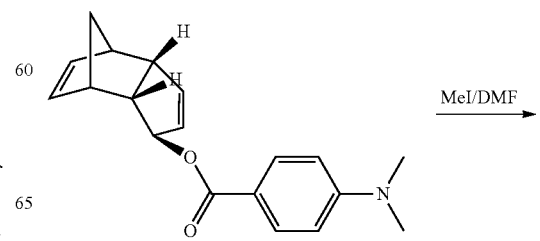

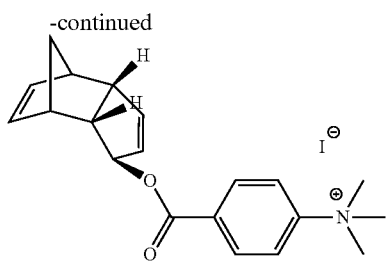

To the solution of the ester product of Step 1 in DMF (2 ml), MeI (5 ml, excess) was added. The solution was stirred for 48 hours at room temperature. Then solvent was removed and diethyl ether was added to yield a white precipitate. The precipitate (compound of formula 12) was separated and washed with ether for thrice and isolated as its pure form after drying (yield: 100%).

Following are the $^1$H— and $^{13}$C-NMR spectral data for compound of Formula 12:

$^1$H NMR (DMSO-$d_6$, δ ppm, 400 MHz): 8.142 (4H, s), 6.126 (1H, q), 6.046 (1H, d, 5.6 Hz), 5.937 (1H, q), 5.708 (1H, d), 5.159 (1H, s), 3.656 (9H, s), 3.412 (1H, s), 3.127 (1H, s), 2.903 (1H, d), 2.777-2.765 (1H, m), 1.546 (1H, d), 1.563 (1H, d).

$^{13}$C NMR (DMSO-$d_6$, δ ppm, 100 MHz): 164.75, 150.93, 141.41, 136.18, 132.98, 132.89, 132.83, 131.83, 131.12, 130.74, 121.76, 83.60, 56.95, 54.77, 51.44, 50.16, 44.74, 34.95.

Figure 12A:
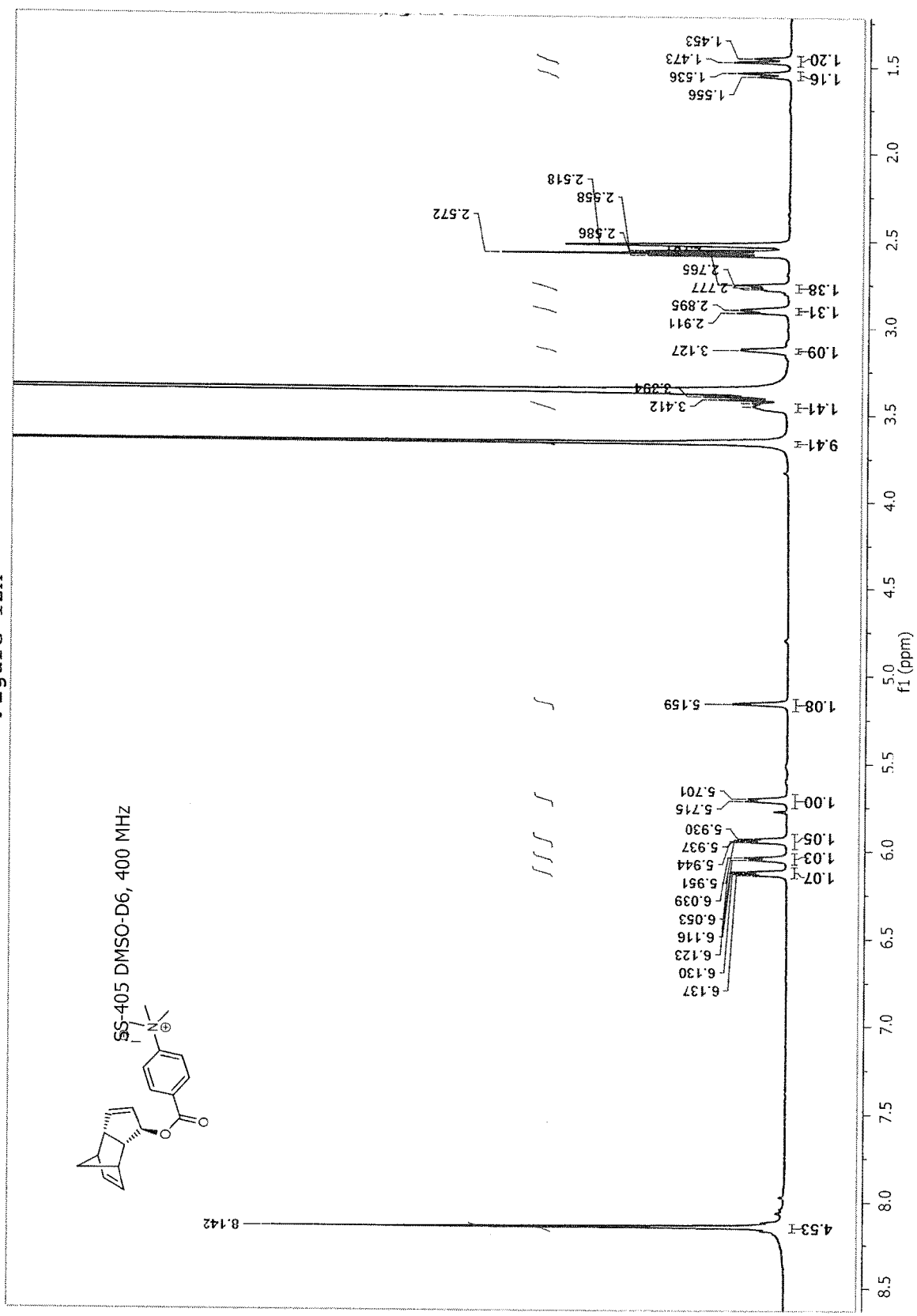
FIG. 12A provides a $^1$H-NMR spectrum of compound of Formula 12.
Figure 12B:
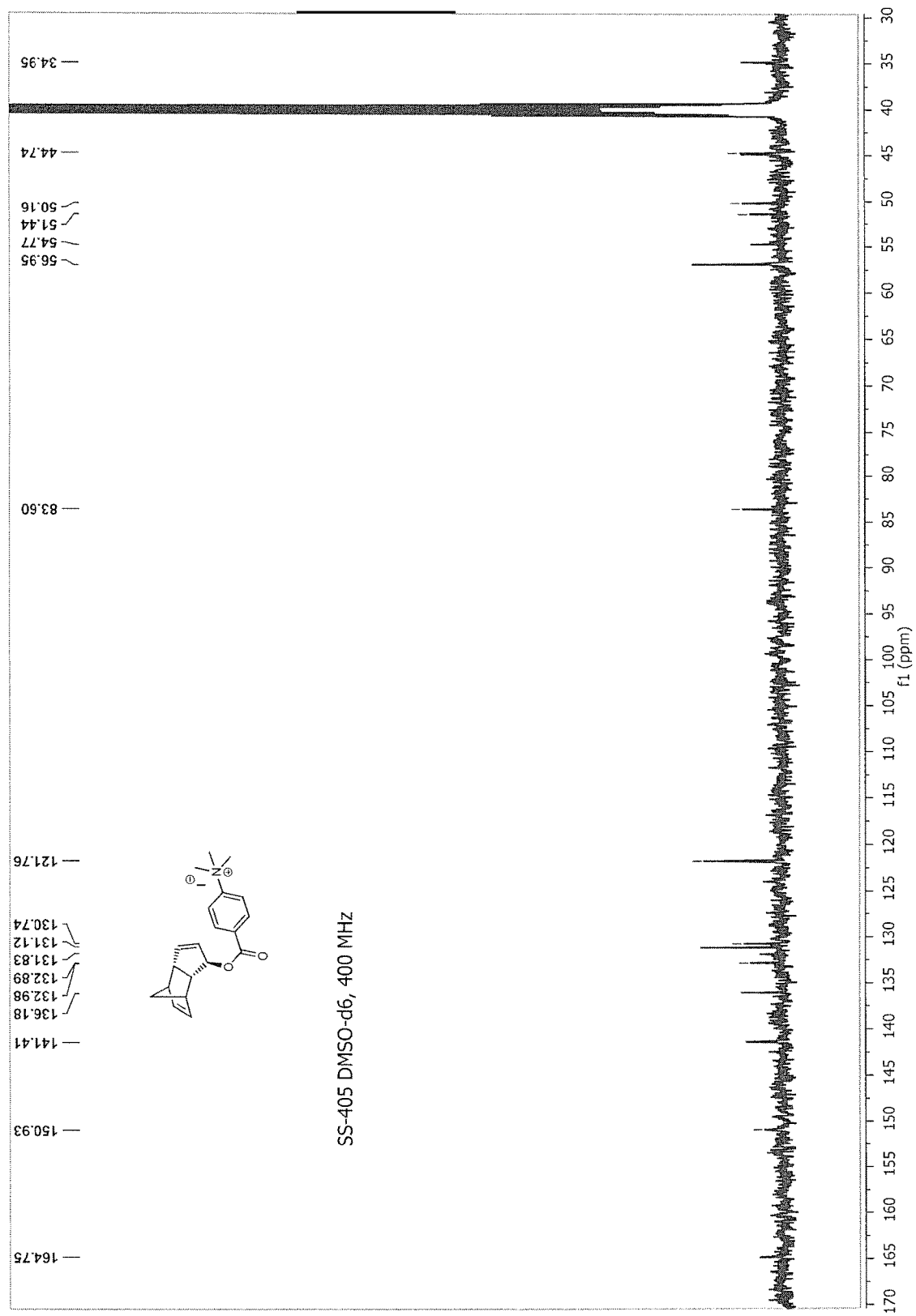
FIG. 12B provides a $^{13}$C-NMR spectrum of compound of Formula 12.

$^1$H— and $^{13}$C-NMR spectra for compound of Formula 12 are provided in FIGS. 12A and 12B, respectively.

Figure 12C:
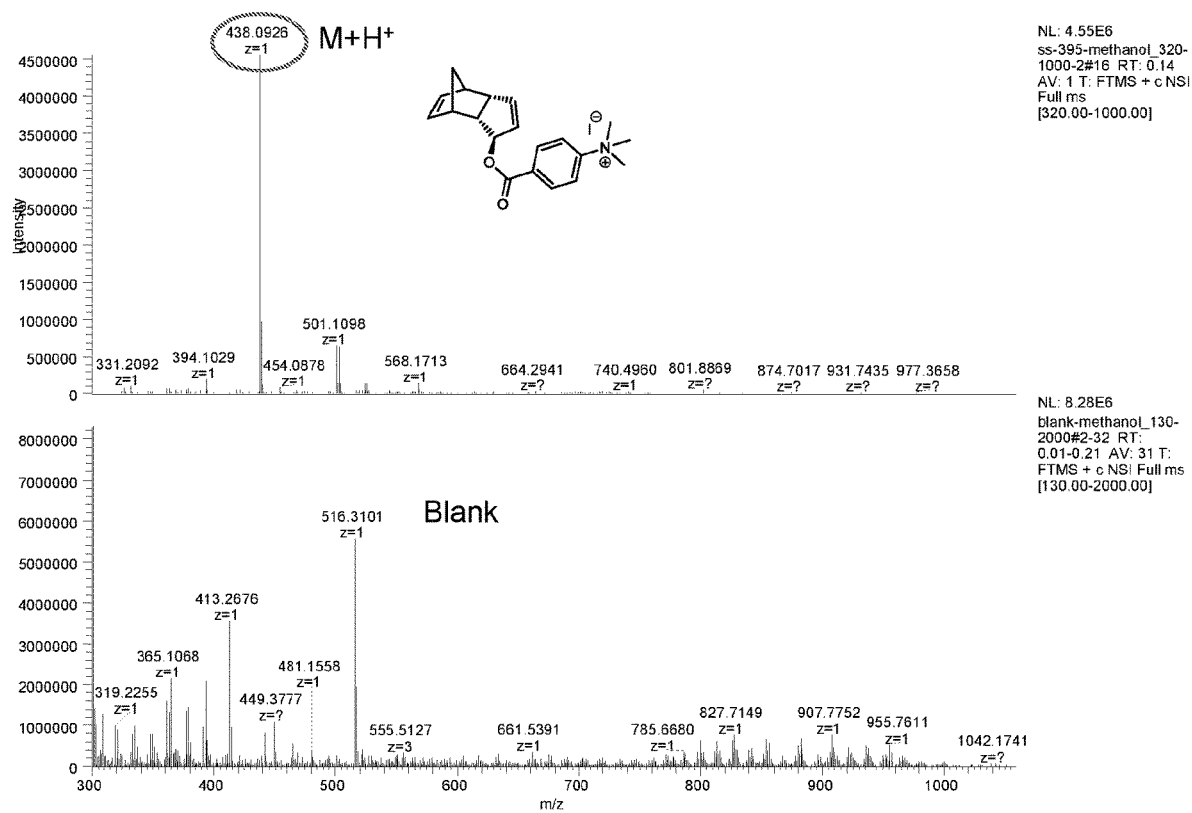
FIG. 12C provides HRMS spectrum for compound of Formula 12.

HRMS spectra for compound of Formula 12 are provided in FIG. 12C.

Example 8

Preparation of Compound of Formula 13

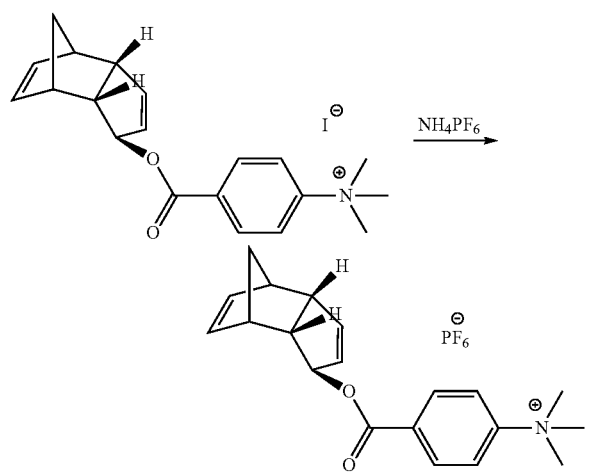

Compound of Formula 12 (860 mg) was dissolved in water (100 ml) and the insoluble part was filtered off. The filtrate was collected and to it was added NH$_4$PF$_6$ (~1.5 gm) to get white precipitate. It was left for overnight stirring. Then an extraction was done with CHCl$_3$. The organic layer was collected, dried over MgSO$_4$ and collected as white gum after concentration. A white and pure precipitate (compound of Formula 13) was obtained after adding hexane into that gum (yield: 77%, Melting point: 150° C.).

Following is the $^1$H-NMR spectral data for compound of Formula 13:

$^1$H NMR (CDCl$_3$, δ ppm, 400 MHz): 8.241 (2H, d), 7.799 (2H, d), 6.085 (1H, q), 5.972 (1H, d), 5.913 (1H, q), 5.663 (1H, d), 5.210 (1H, s), 3.677 (9H, s), 3.464 (1H, s), 3.164 (1H, s), 2.881 (1H, s), 2.747 (1H, m), 1.638 (1H, d), 1.457 (1H, d).

Figure 13A:
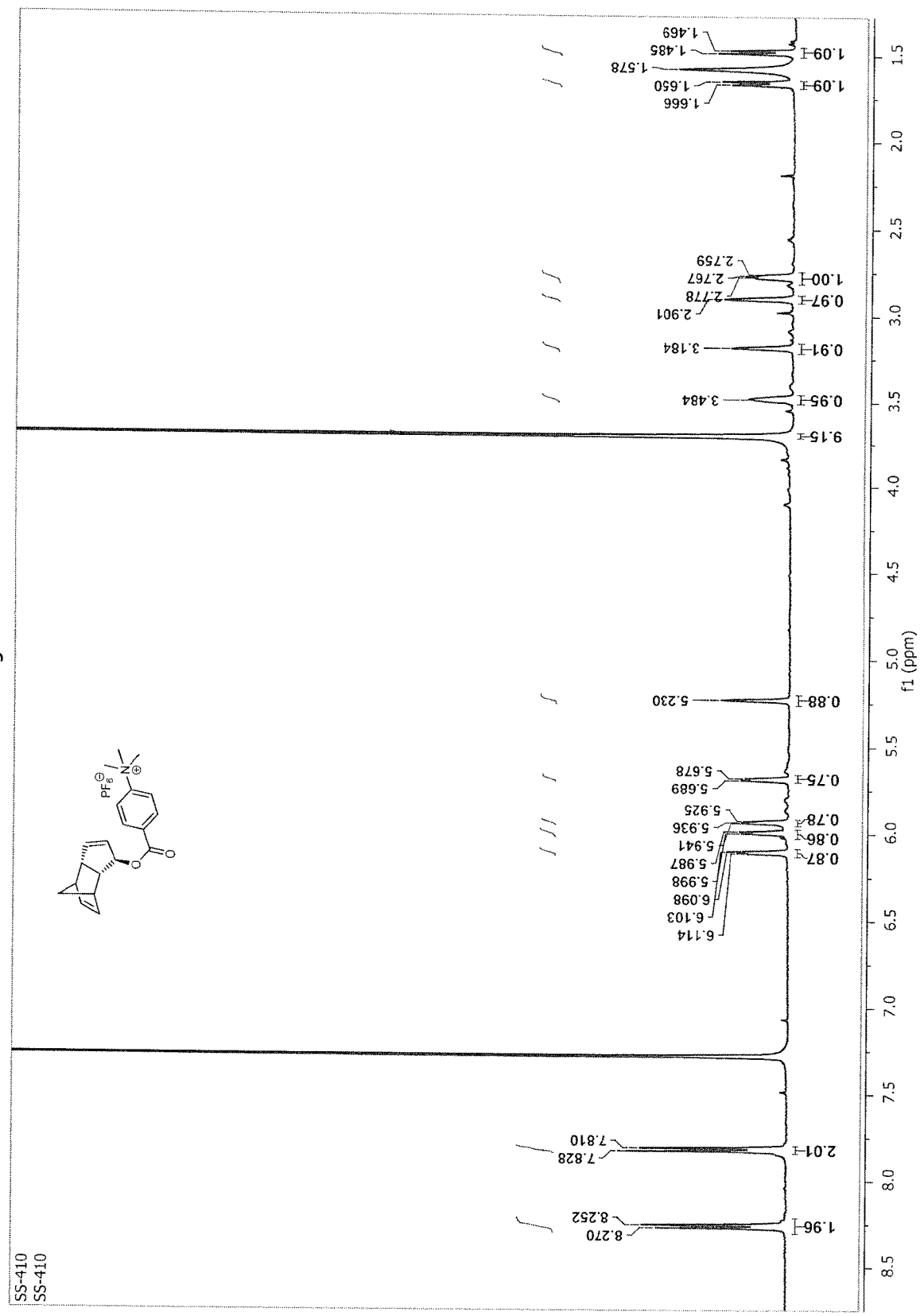
FIG. 13A shows a $^1$H-NMR spectrum of compound of Formula 13.

$^1$H-NMR spectrum for compound of Formula 13 is provided in FIG. 13A.

Figure 13B:
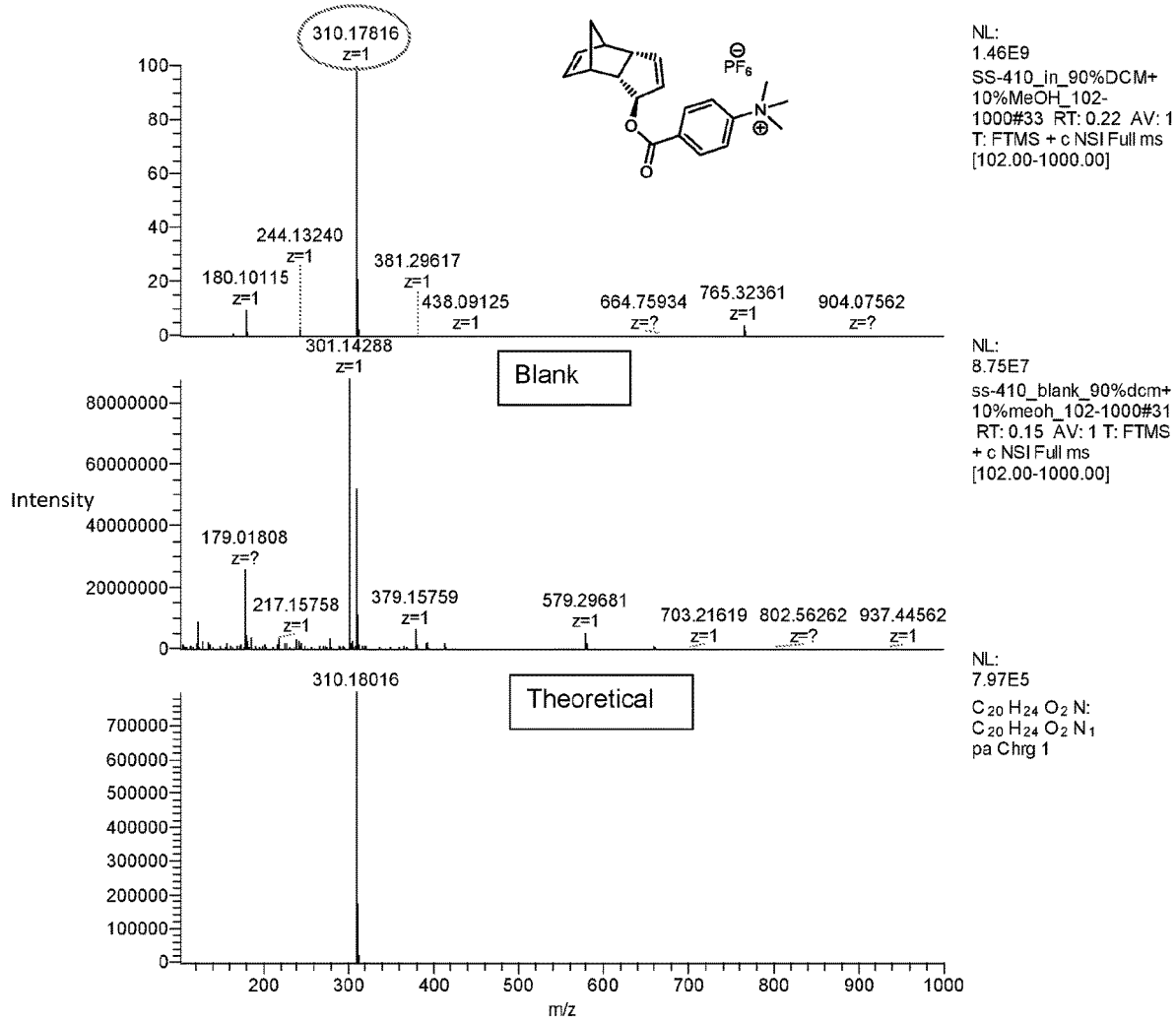
FIG. 13B shows HRMS spectrum for compound of Formula 13.

HRMS spectra for compound of Formula 13 are provided in FIG. 13B.

Example 9

Preparation of acetoxydicyclopentadiene (DCPD-OAc)

Acetoxydicyclopentadiene (DCPD-OAc) (compound of Formula 14), was prepared by following the general procedure for esterification of DCPD-OH described in Example 6 hereinabove. Briefly, a three necked round bottom flask was charged with DCPD-OH (1 gm, 6.75 mmol) and was subjected to vacuum and then nitrogen consecutively three times. Then, dry DCM (50 ml) and Et$_3$N (1.5 ml) were added to it and the solution was stirred at 0° C. for 10 min. After that, acetyl chloride (10.13 mmol) was added through syringe in dropwise fashion. It was then kept for 12 hours stirring at room temperature. After that, it was washed with water. The organic layer was separated and dried over MgSO$_4$. It was finally concentrated and subjected to flash column chromatography for purification. The product (compound of Formula 14) was eluted with ethyl acetate/petroleum ether (1:19) on neutral alumina stationary phase.

Formula 14

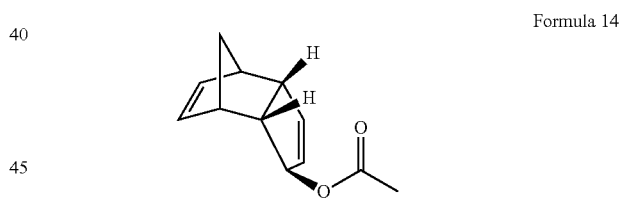

Compound of Formula 14 is a colorless liquid, isolated yield: 85%, boiling point: 224-226° C.

Following are the $^1$H— and $^{13}$C-NMR spectral data for compound of Formula 14:

$^1$H NMR (500 MHz, CDCl$_3$, δ ppm) (3a): 6.03 (dd, J=5.5, 3.0 Hz, 1H), 5.88 (bd, J=5.5 Hz, 1H), 5.86 (dd, J=5.5, 3.0 Hz, 1H), 5.57 (bd, J=5.5 Hz, 1H), 4.96 (bs, 1H), 3.38-3.37 (m, 1H), 3.10 (bs, 1H), 2.82 (bs, 1H), 2.61-2.59 (m, 1H), 2.02 (s, 3H), 1.58 (bd, J=8.2 Hz, 1H), 1.40 (bd, J=8.2 Hz, 1H).

$^{13}$C NMR (125 MHz, CDCl$_3$, δ ppm) (3a): 171.22, 140.15, 135.48, 132.68, 130.86, 82.23, 54.67, 51.47, 50.37, 44.94, 44.84 and 21.51.

Figure 14A:
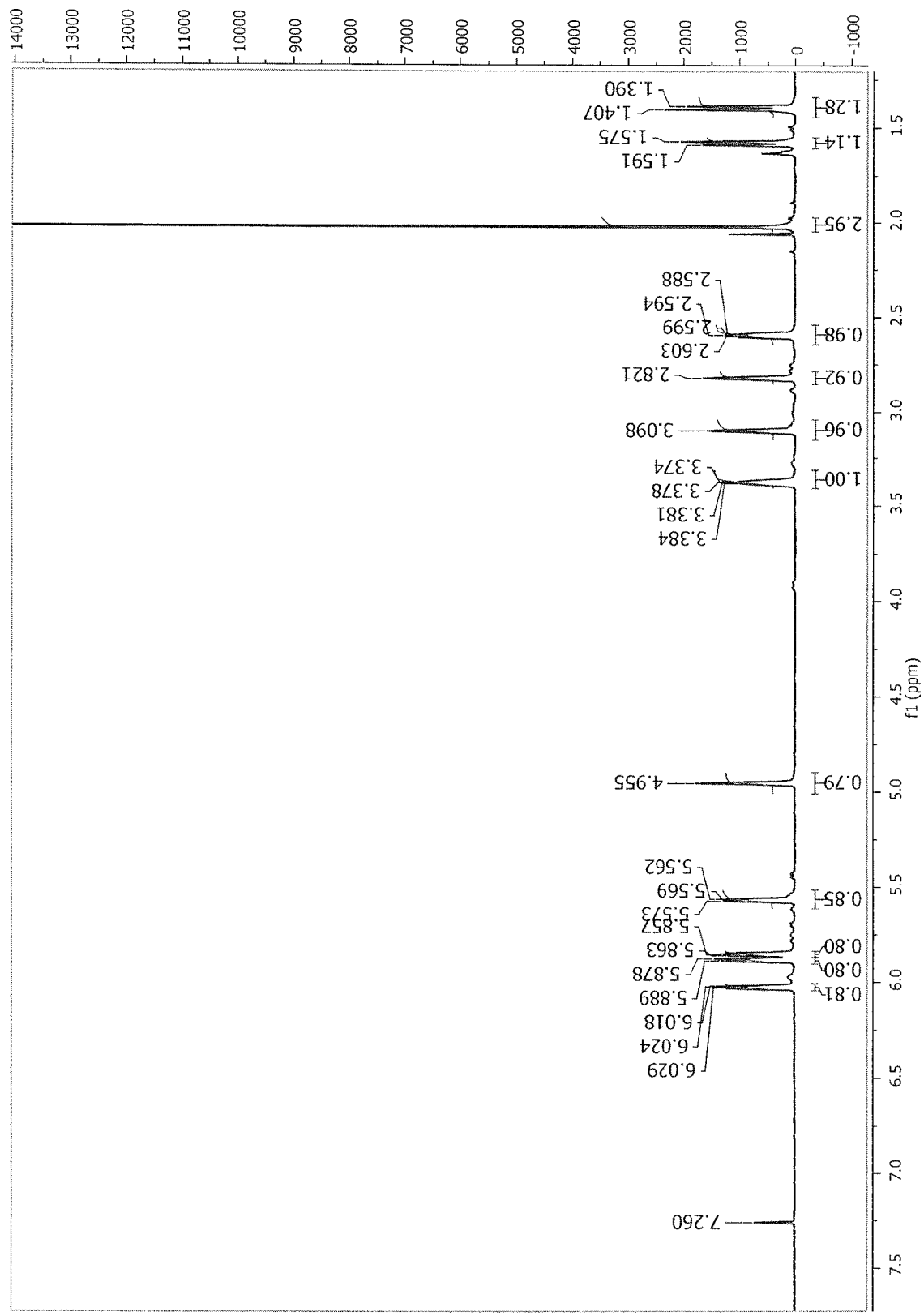
FIG. 14A provides a $^1$H-NMR spectrum of compound of Formula 14.
Figure 14B:
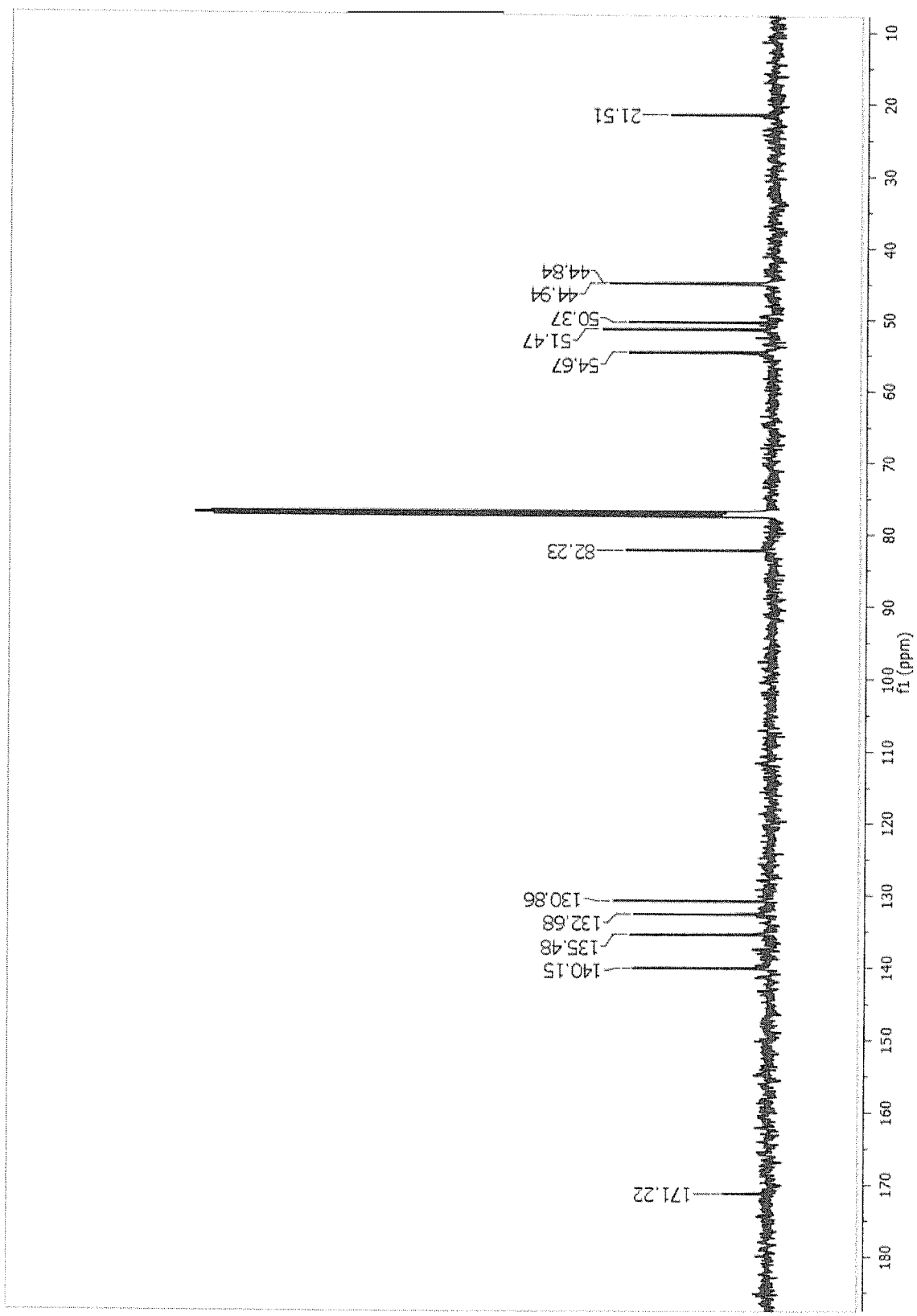
FIG. 14B provides a $^{13}$C-NMR spectrum of compound of Formula 14.

$^1$H— and $^{13}$C-NMR spectra for compound of Formula 14 are provided in FIGS. 14A and 14B, respectively.

Figure 14C:
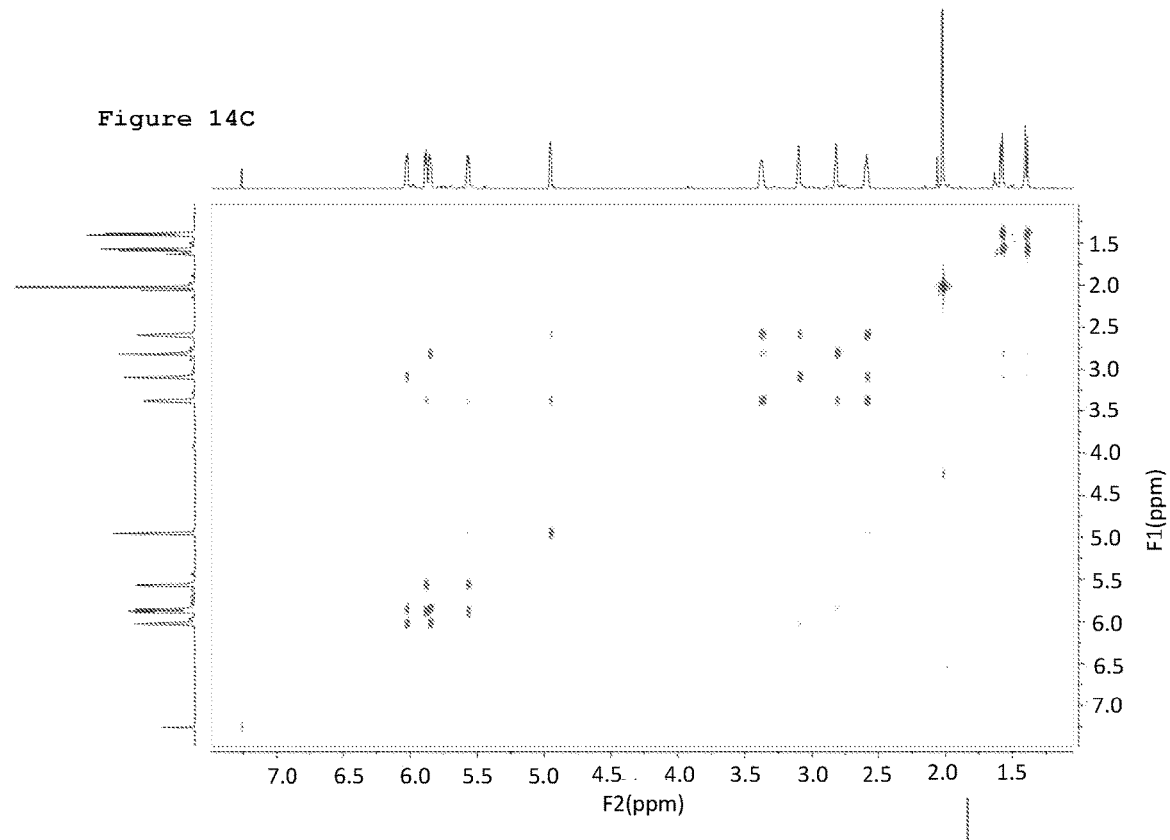
FIG. 14C provides a COSY NMR spectrum of compound of Formula 14 in CDCl$_3$.

COSY NMR spectrum of compound of Formula 14 in CDCl$_3$ is provided in FIG. 14C.

Figure 14D:
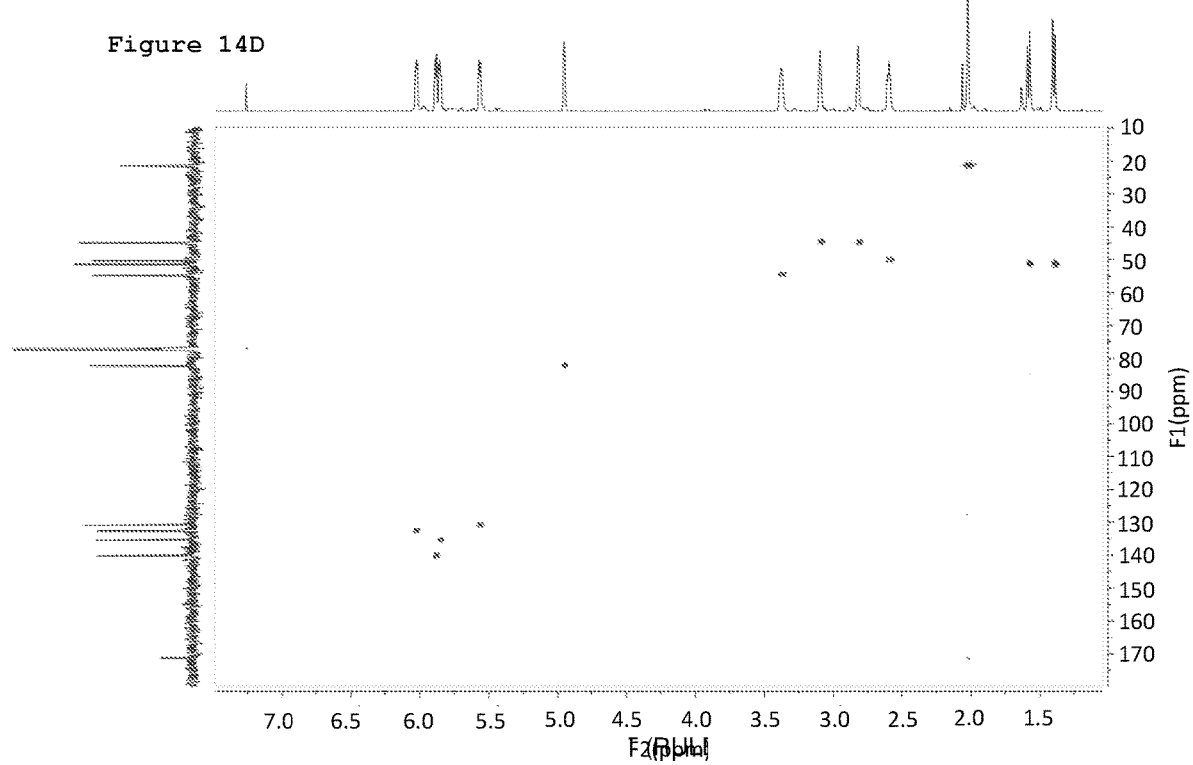
FIG. 14D provides a HMQC spectrum of compound of Formula 14.
Figure 14E:
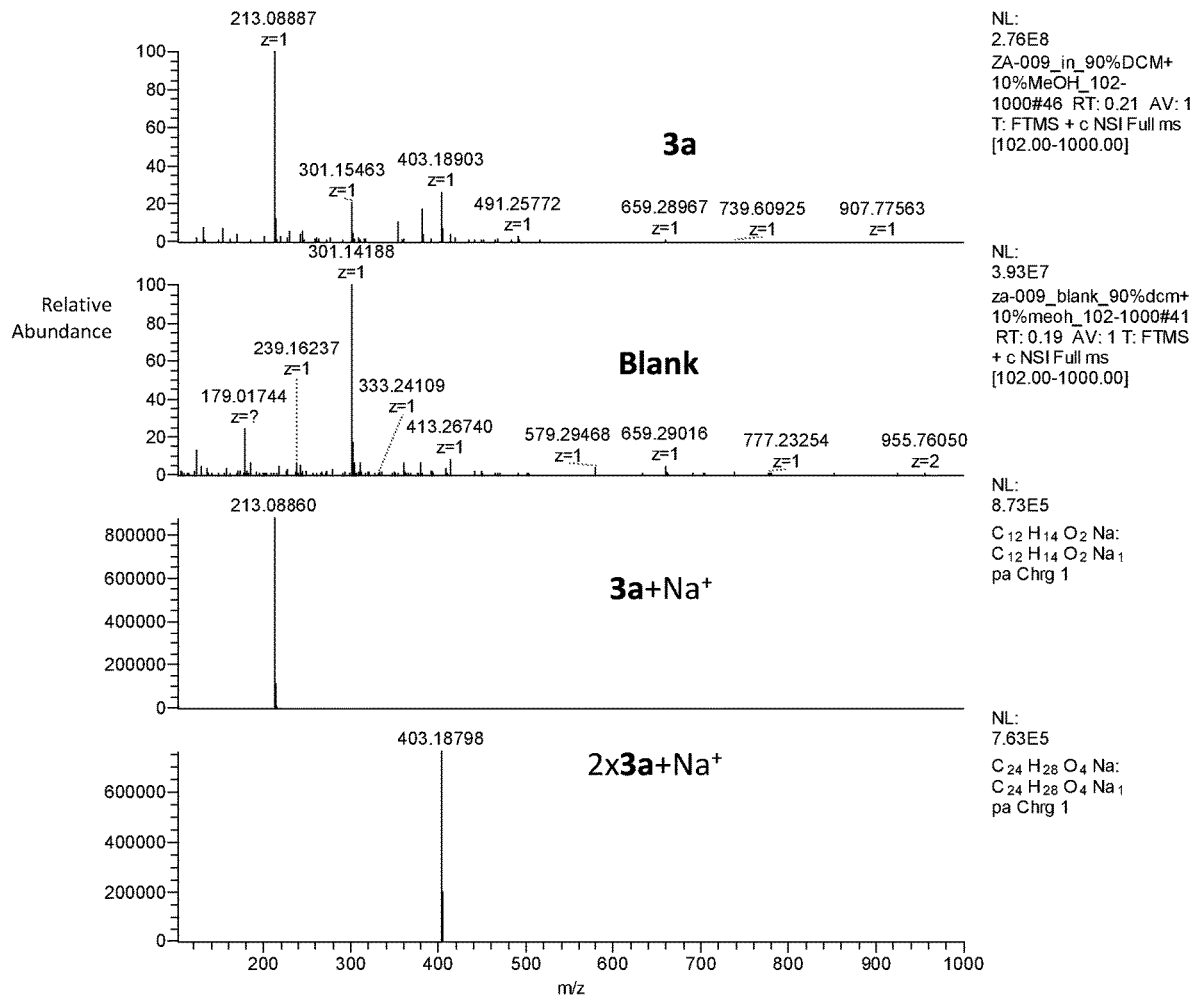
FIG. 14E provides a HRMS spectrum of compound of Formula 14.

HMQC and HRMS spectra for compound of Formula 14 are provided in FIGS. 14D and 14E, respectively.

Figure 14F:
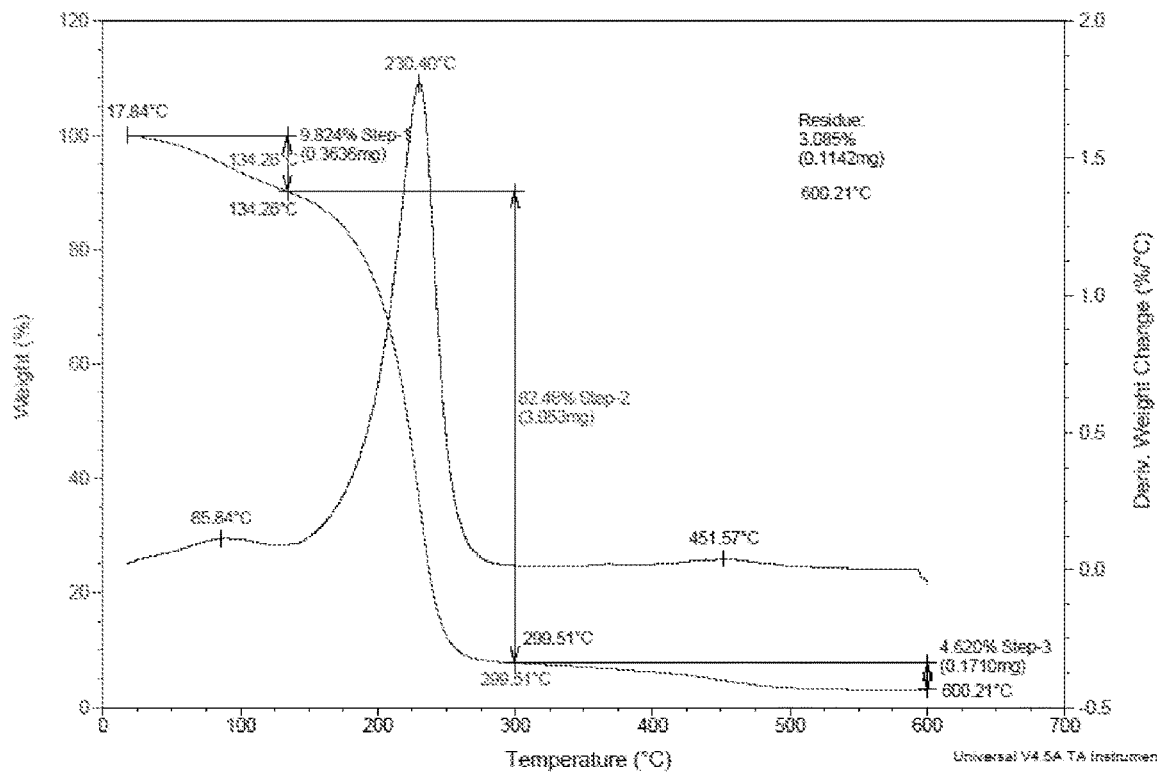
FIG. 14F provide a TGA curve of compound of Formula 14.

TGA curve for compound of Formula 14 is provided in FIG. 14F.

Example 10

TGA Analysis of Some of the Neutral DCPD Derivatives of General Formulae (I) and (II)

Some neutral DCPD derivatives of general Formulae (I) and (II) were analyzed by TGA to evaluate their weight loss at high temperatures. As shown in Table 1, all derivatives displayed maximum rate of weight loss at higher temperatures compared to endo-dicyclopentadiene (endo-DCPD), with a certain correlation to the boiling points of the derivatives.

TABLE 1

| Compound | Maximum rate of weight loss T (° C.) |
|---|---|
| endo-DCPD | 165.7 |
| DCPD-OH | 218.2 |
| Compound of Formula 14 | 230.4 |
| Compound of Formula 11 | 260.1 |
| Compound of Formula 1 | 212.5 |
| Compound of Formula 3 | 226.9 |
| Compound of Formula 4 | 254.1 |

Figure 15:
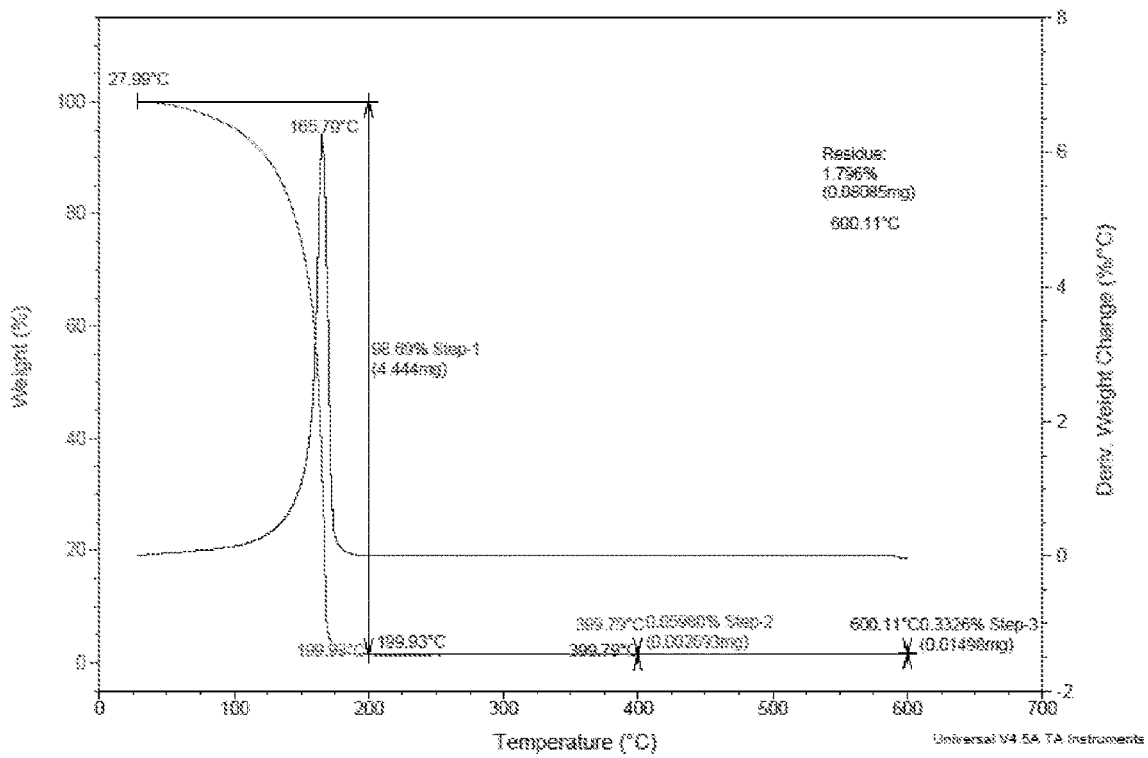
FIG. 15 provides a TGA curve of endo-DCPD.

A TGA curve of endo-DCPD is provided in FIG. 15.

The corresponding TGA curves of DCPD-OH and compounds of Formulae 1, 3, 4, 11 and 14 are provided in FIGS. 2E, 3E, 4E, 11E and 14E respectively.

Example 11

Smell and Volatility Properties of Some of the Neutral DCPD Derivatives of General Formulae (I) and (II)

All of the compounds of Formulae (I) and (II) that were prepared as detailed in Examples 1-9 above, had a significantly reduced smell compared to endo-DCPD.

The boiling points of some of the neutral compounds of Formulae (I) and (II) were measured and are provided in Table 2.

TABLE 2

| Compound | Boiling Point T (° C.) |
|---|---|
| endo-DCPD | 170 |
| DCPD-OH | 216-217 |
| Compound of Formula 14 (DCPD-OAc) | 224-226 |
| Compound of Formula 1 (DCPD-OMe) | 214-217 |
| Compound of Formula 3 (DCPD-OPr) | 216-218 |
| Compound of Formula 4 (DCPD-OOc) | 220-222 |

Without being bound by theory, it is believed that the significantly reduced smell is due to increase of intermolecular polar interactions and lowering of the compounds' volatility, as can be seen from the boiling points of some of the compounds provided in Table 2.

Example 12

Formation and Characterization of Cross-Linked Polymers of Neutral Monomers of Formula (I) and (II)

A.

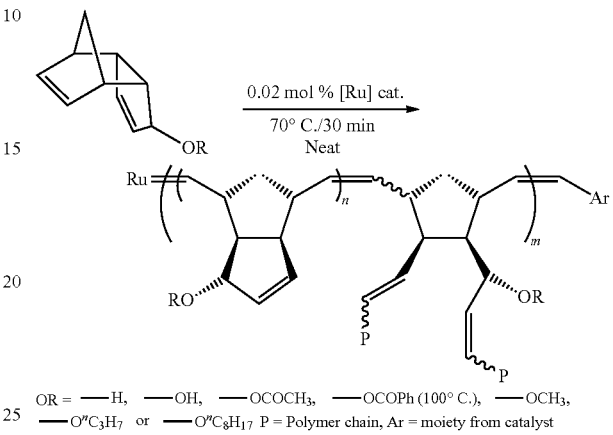

OR = —H, —OH, —OCOCH$_3$, —OCOPh (100° C.), —OCH$_3$, —O″C$_3$H$_7$ or —O″C$_8$H$_{17}$   P = Polymer chain, Ar = moiety from catalyst Polymerization of some neutral monomers of general Formulae (I) and (II) (was carried out according to the following general procedure: 1 mmol of monomer (R=—H, —OH, —OCOCH$_3$, —OCH$_3$, —O″C$_3$H$_7$ or —O″C$_8$H$_{17}$) was introduced to a 4 ml glass vial and then $2^{nd}$ generation Grubbs' catalyst (2.0×10$^{-4}$ mmol) dissolved in a small amount of dry CH$_2$Cl$_2$ (~50 µl) was added. After mixing the solution very quickly, the solvent was removed by gentle blowing of argon and the remaining mixture was transferred into a rectangular shaped (2 cm×1 cm×1 mm) aluminum mold and placed in an oven of pre-set temperature at 70° C. for 60 minutes to produce the highly cross-linked solid polymer.

The following monomers were polymerized by following the above detailed procedure: endo-dicyclopentadiene (endo-DCPD), hydroxydicyclopentadiene (interchangeably identified herein as hydroxyl-DCPD or as DCPD-OH), compound of Formula 1, compound of Formula 3, compound of Formula 4 and acetoxydicyclopentadiene (compound of Formula 14). All reactions were performed with Grubbs' $2^{nd}$ generation catalyst 1,3-Bis-(2,4,6-trimethylphenyl)-2-imidazolidinylidene]dichloro-(phenylmethylene) (tricyclohexylphosphine)ruthenium), commercially available from Sigma Aldrich.

Polymerization reactions of hydroxydicyclopentadiene (DCPD-OH), of compound of Formula 1, of compound of Formula 3 and of compound of Formula 14, resulted in a solid, hard polymer. Polymerization of the octyl derivative of Formula 4, resulted in a rubbery, flexible polymer.

All of the obtained polymers were odourless.

Characteristic properties of the resultant polymers were measured using Differential Scanning calorimetry (DSC) technique and by TGA, in order to evaluate the effect of the substituents on the polymers' thermal properties.

Figure 16A:
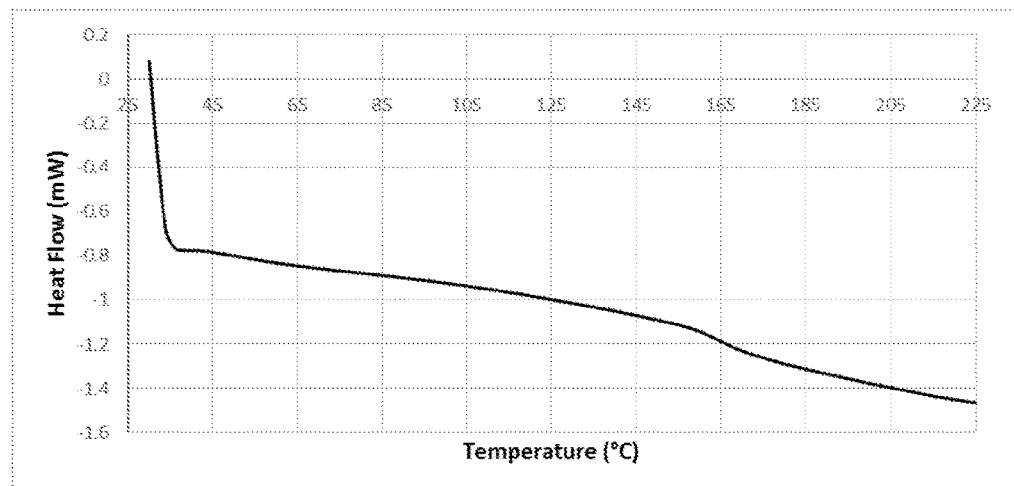
FIG. 16A provide a DSC curve of pDCPD (the polymer of endo-DCPD).

DSC curve of a polymer of endo-DCPD (pDCPD) is provided in FIG. 16A.

Figure 16B:
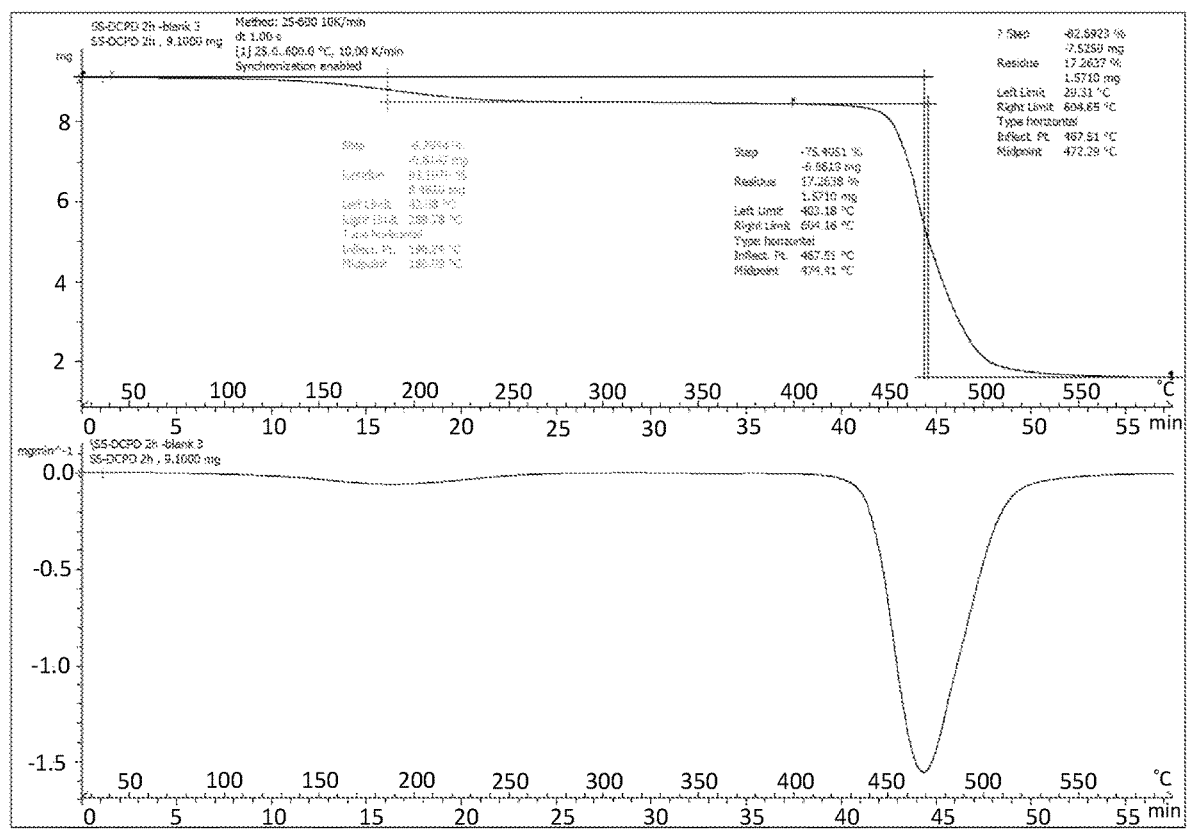
FIG. 16B provides a TGA curve of pDCPD (the polymer of endo-DCPD), after 2 hours of curing.

TGA curve of a polymer of endo-DCPD (pDCPD), after 2 hours of curing, is provided in FIG. 16B.

Figure 17A:
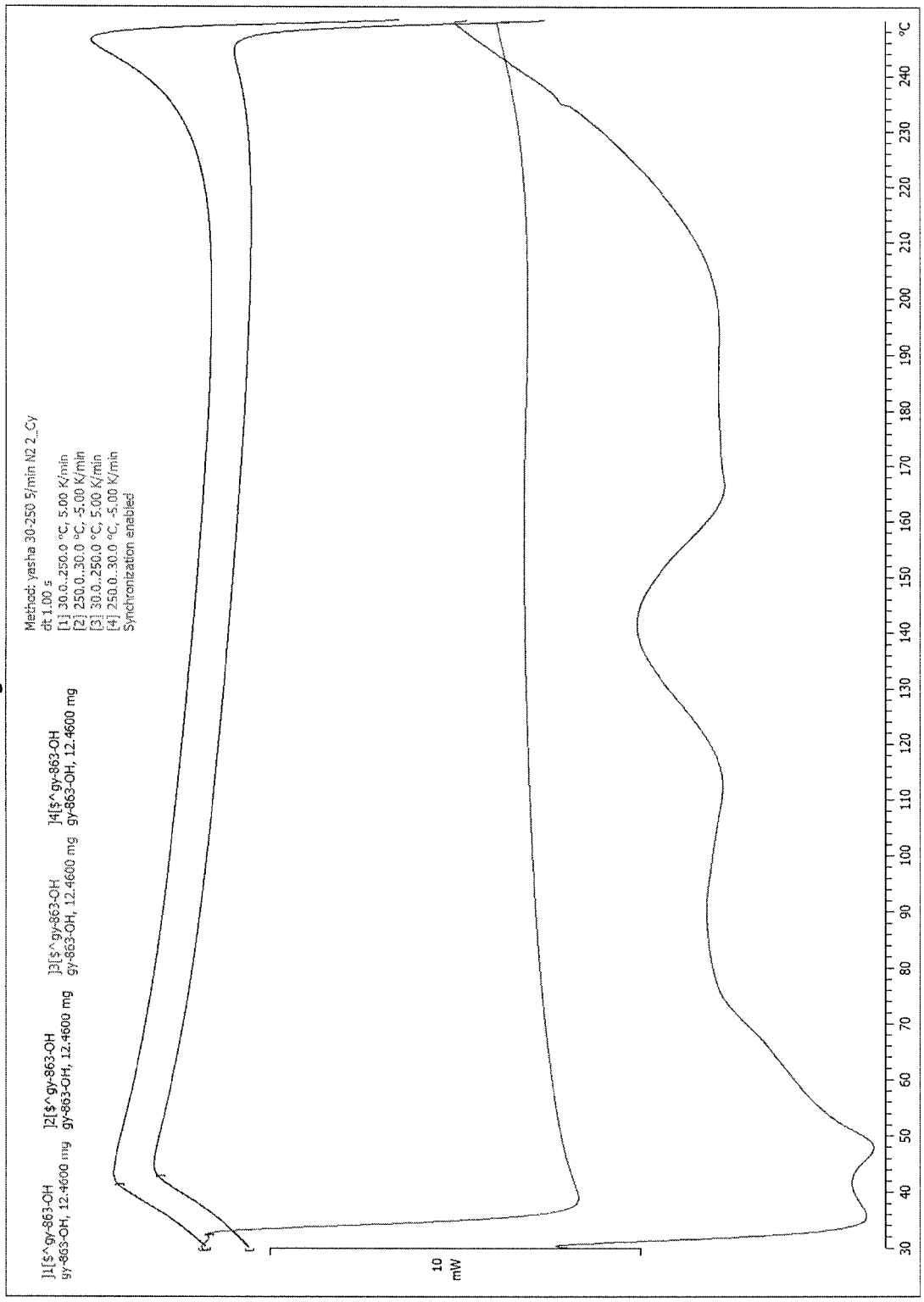
FIG. 17A provides a DSC curve of pDCPD-OH (the polymer of hydroxy-DCPD (DCPD-OH)).

DSC curve of a polymer of hydroxyl-DCPD (pDCPD-OH) is provided in FIG. 17A.

Figure 17B:
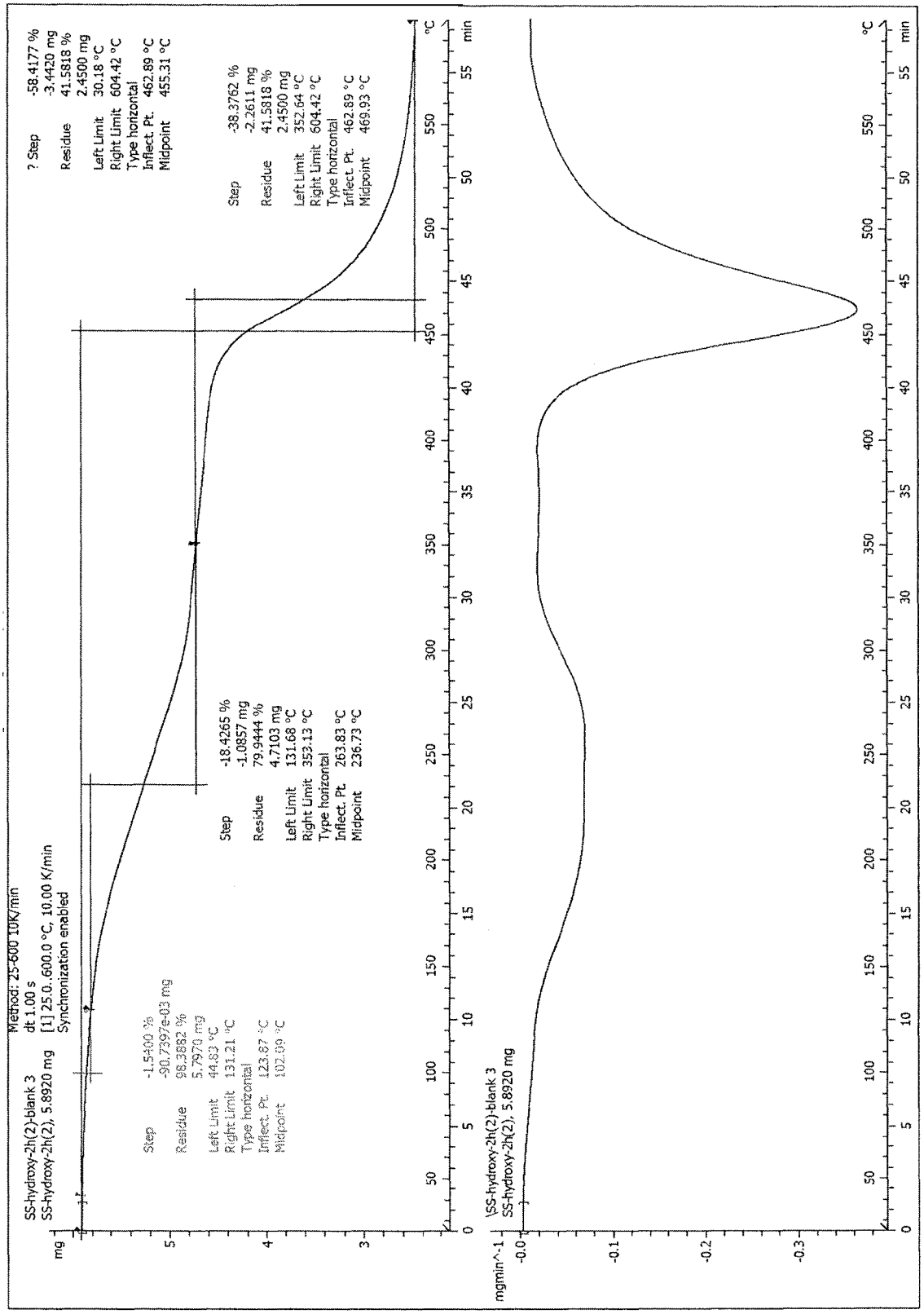
FIG. 17B provides a TGA curve of pDCPD-OH (the polymer of hydroxy-DCPD (DCPD-OH)), after 2 hours of curing.

TGA curve of a polymer of hydroxyl-DCPD (pDCPD-OH), after 2 hours of curing, is provided in FIG. 17B.

Figure 18A:
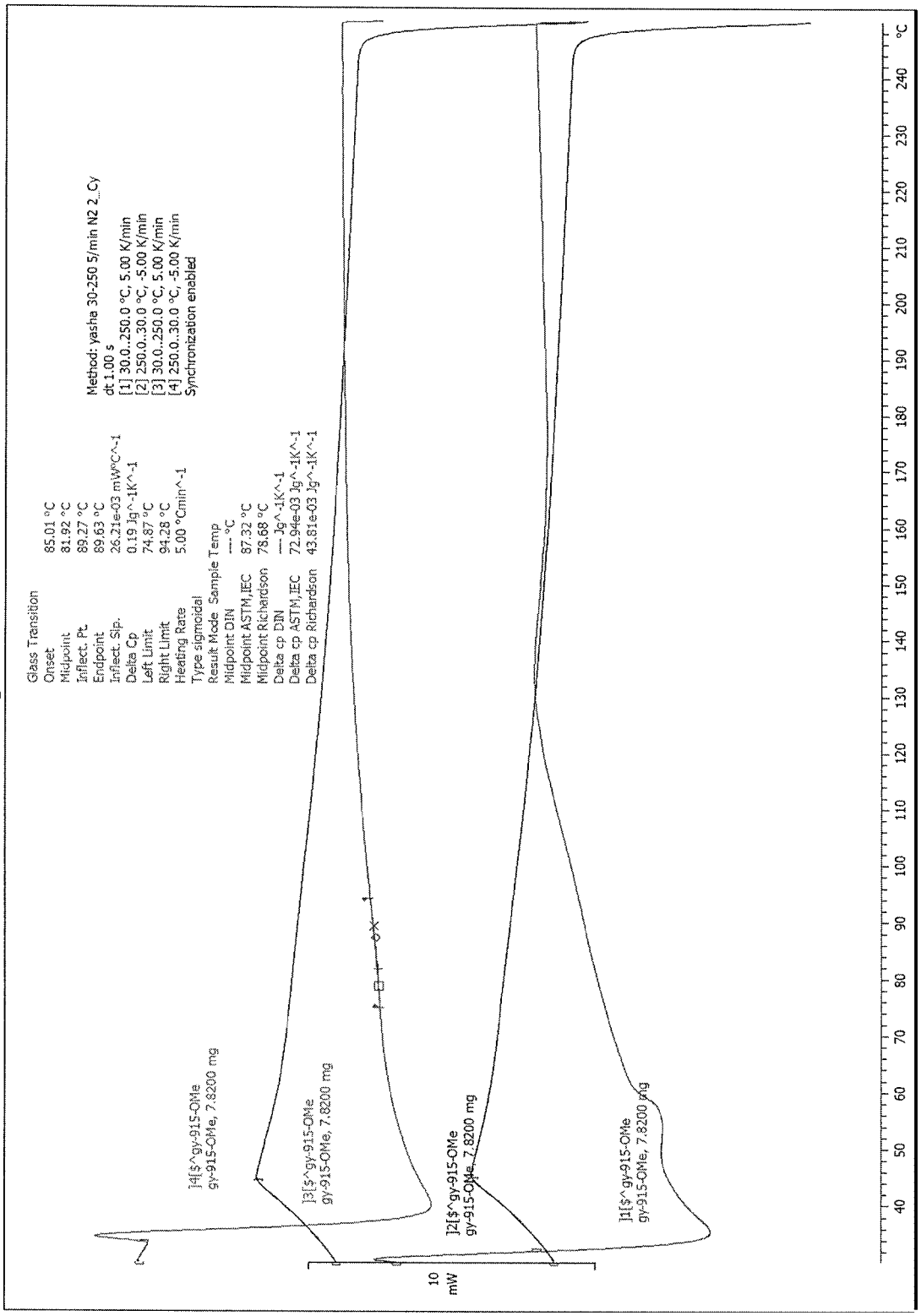
FIG. 18A provides a DSC curve of pDCPD-OMe (the polymer of a compound of Formula 1).

DSC curve of a polymer of compound of Formula 1 is provided in FIG. 18A.

Figure 18B:
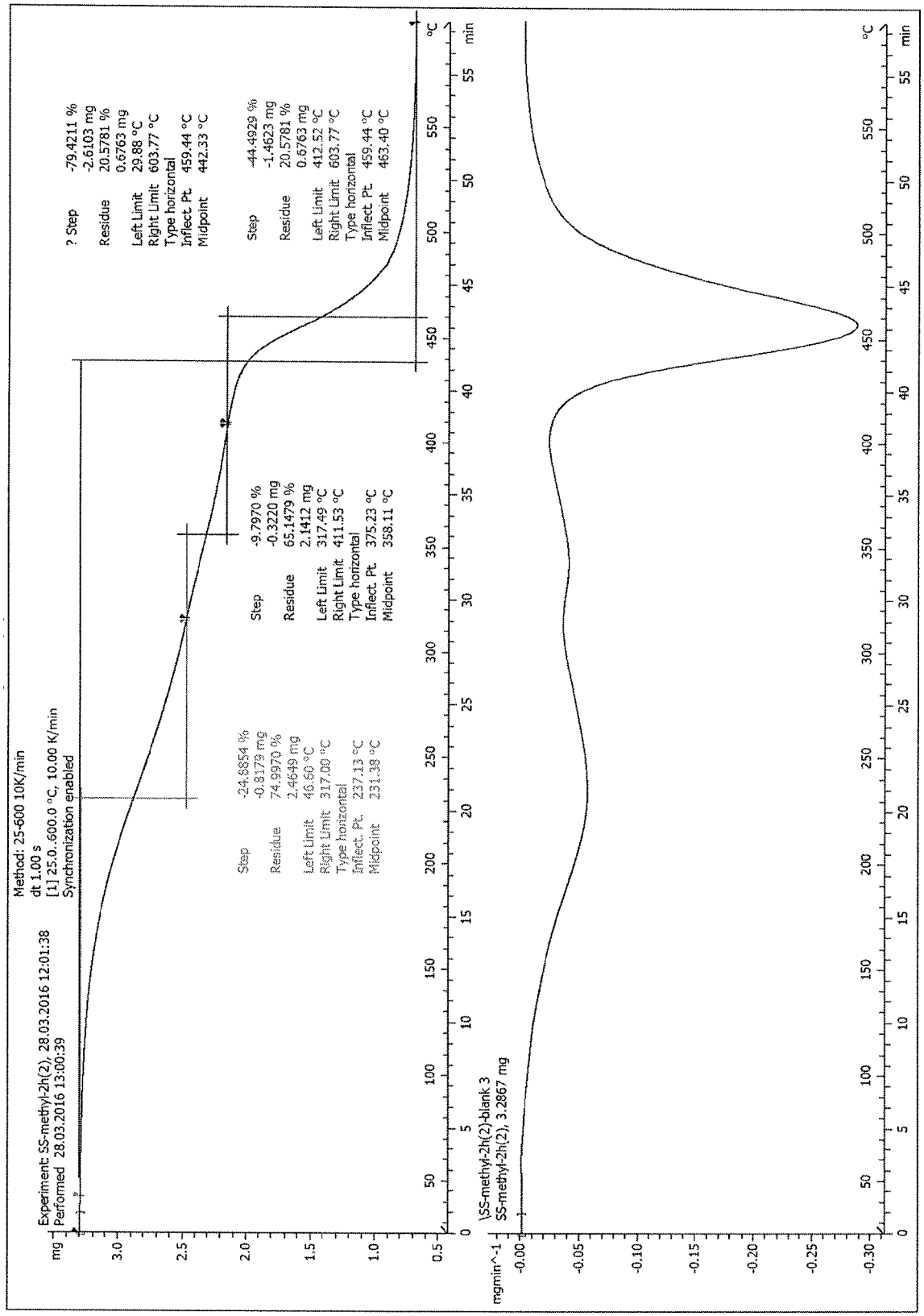
FIG. 18B provides a TGA curve of pDCPD-OMe (the polymer of a compound of Formula 1), after 2 hours of curing.

TGA curve of a polymer of compound of Formula 1, after 2 hours of curing, is provided in FIG. 18B.

Figure 19A:
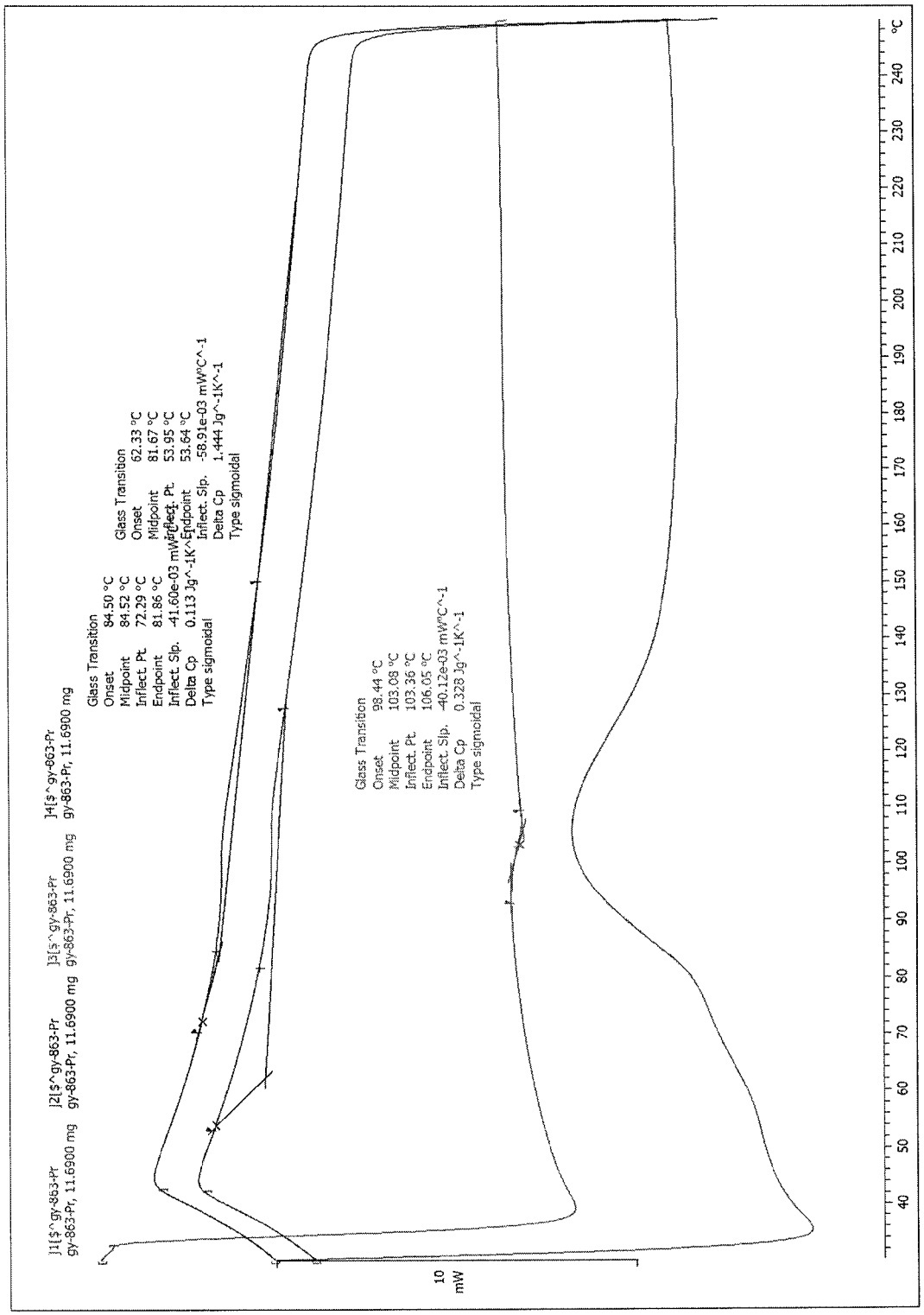
FIG. 19A provides a DSC curve of pDCPD-OPr (the polymer of a compound of Formula 3).

DSC curve of a polymer of compound of Formula 3 is provided in FIG. 19A.

Figure 19B:
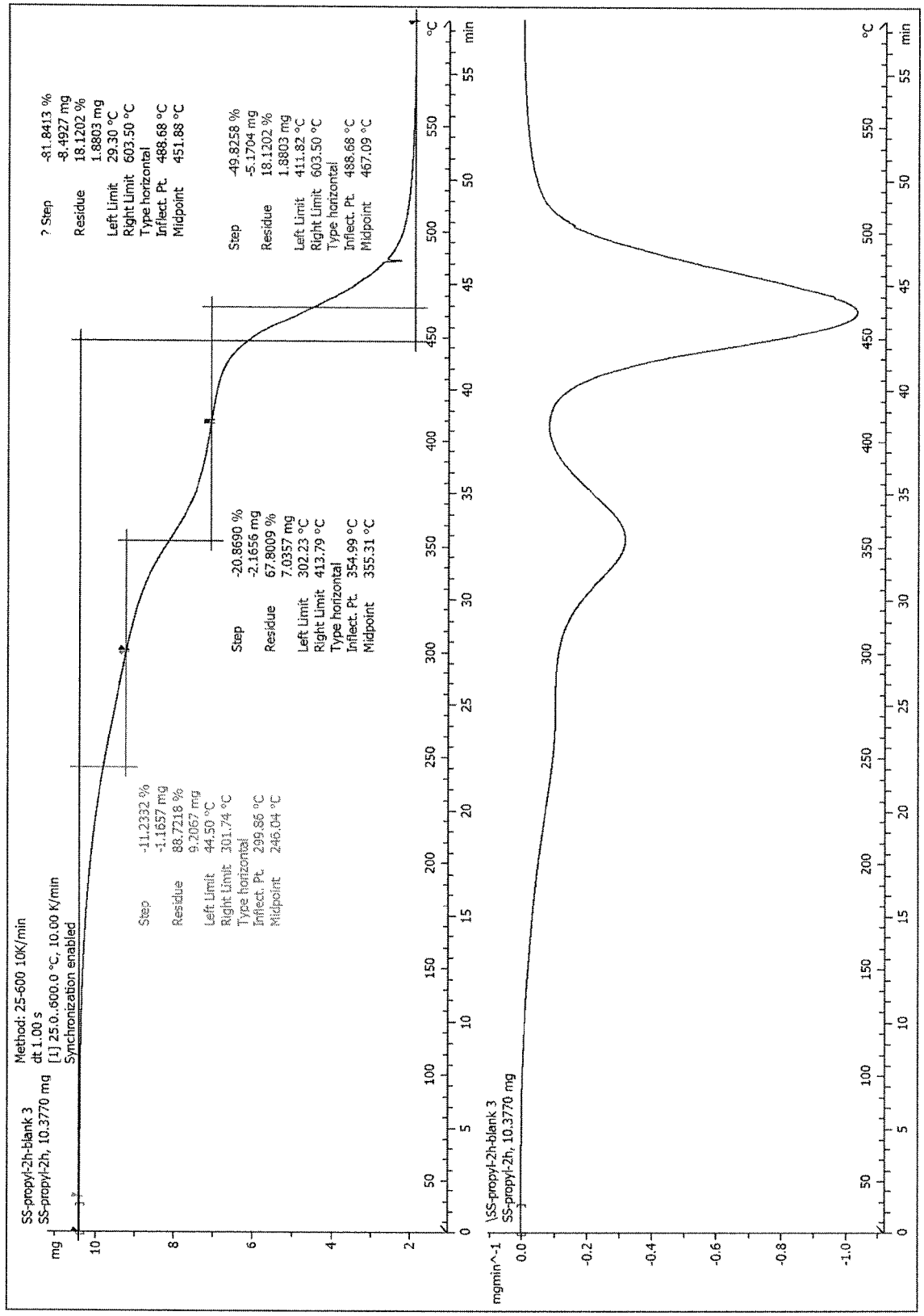
FIG. 19B provides a TGA curve of pDCPD-OPr (the polymer of a compound of Formula 3), after 2 hours of curing.

TGA curve of a polymer of compound of Formula 3, after 2 hours of curing, is provided in FIG. 19B.

Figure 20A:
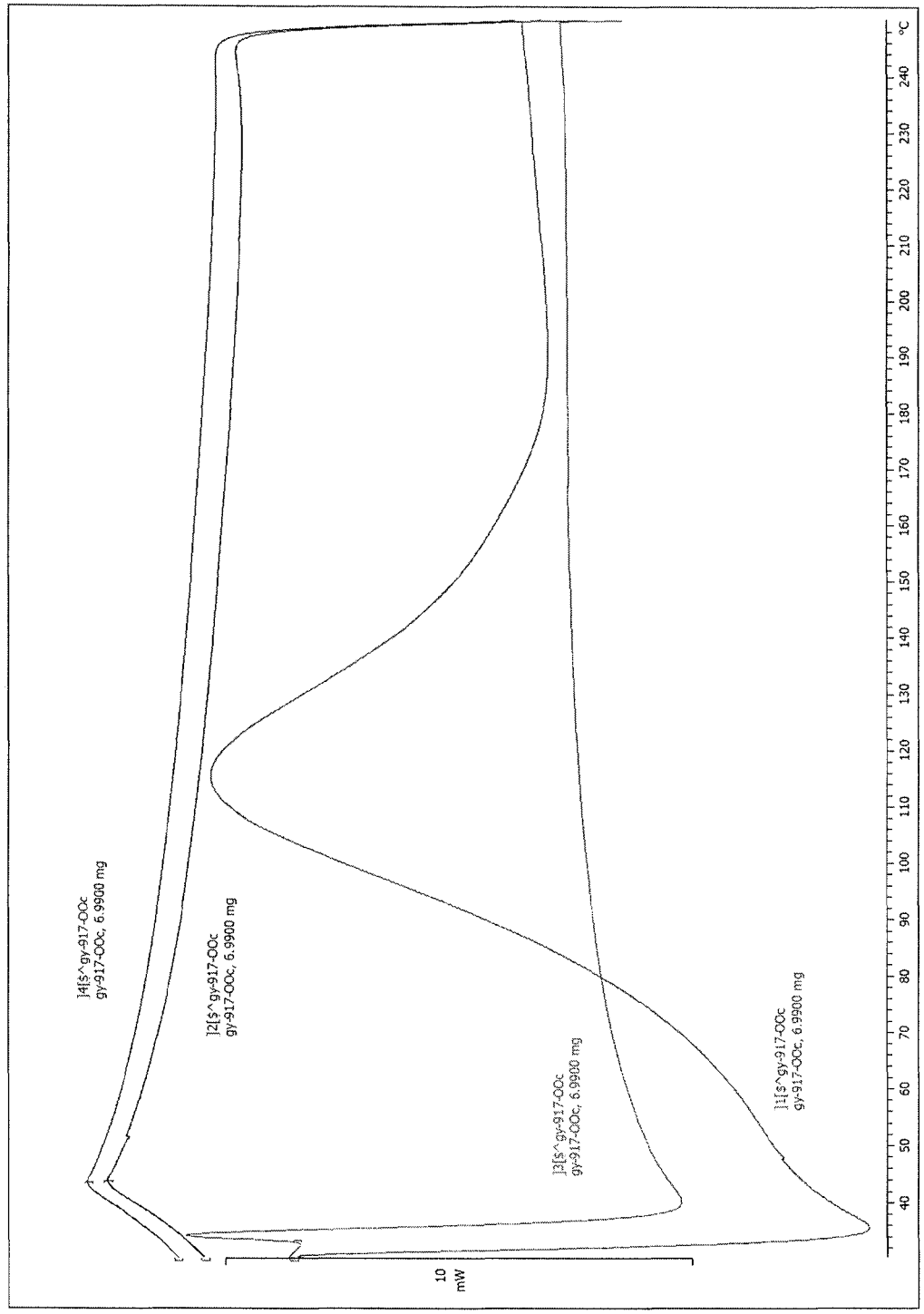
FIG. 20A provides a DSC curve of pDCPD-OOc (the polymer of a compound of Formula 4).

DSC curve of a polymer of compound of Formula 4 is provided in FIG. 20A.

Figure 20B:
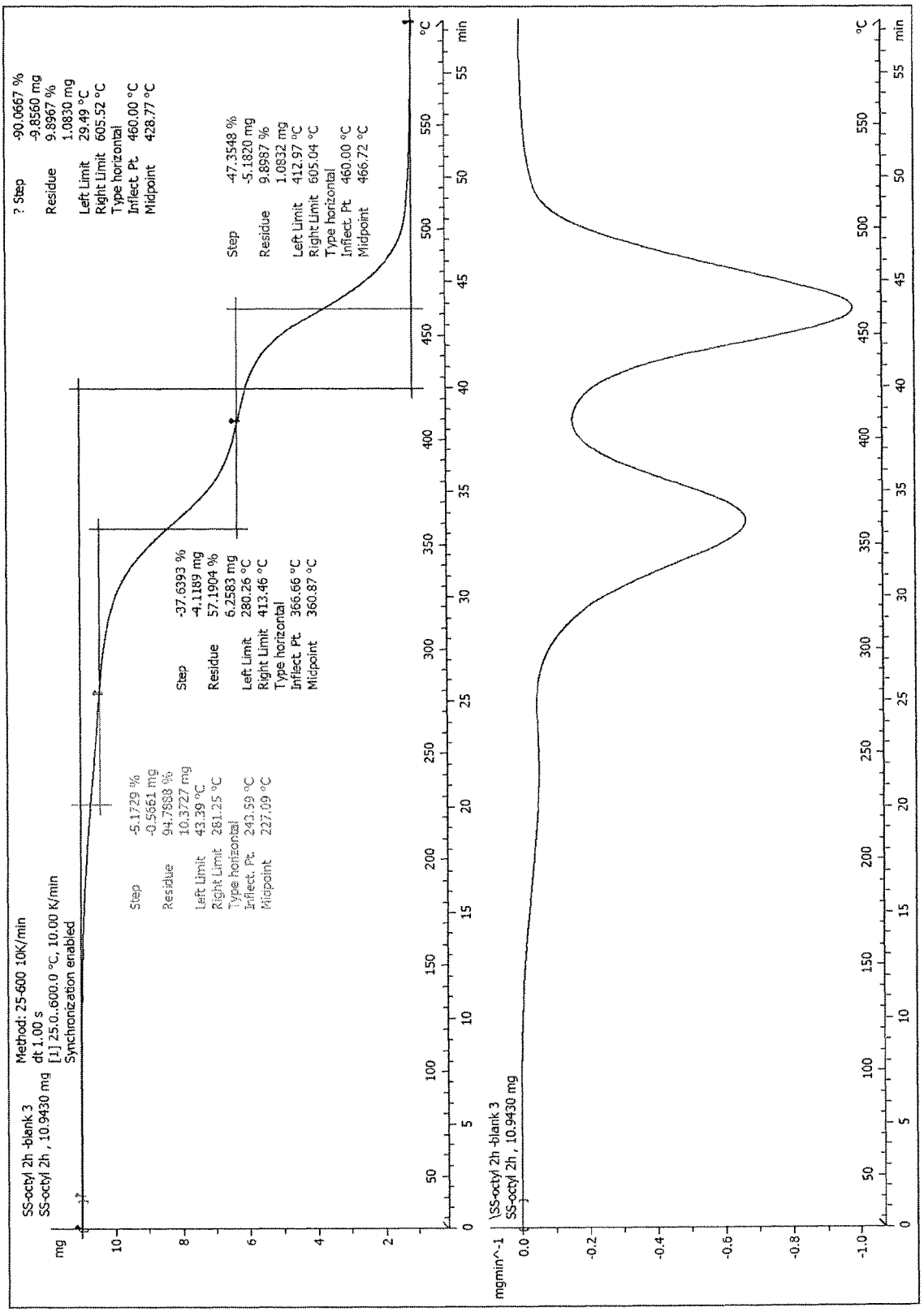
FIG. 20B provides a TGA curve of pDCPD-OOc (the polymer of a compound of Formula 4), after 2 hours of curing.

TGA curve of a polymer of compound of Formula 4, after 2 hours of curing, is provided in FIG. 20B.

Figure 21A:
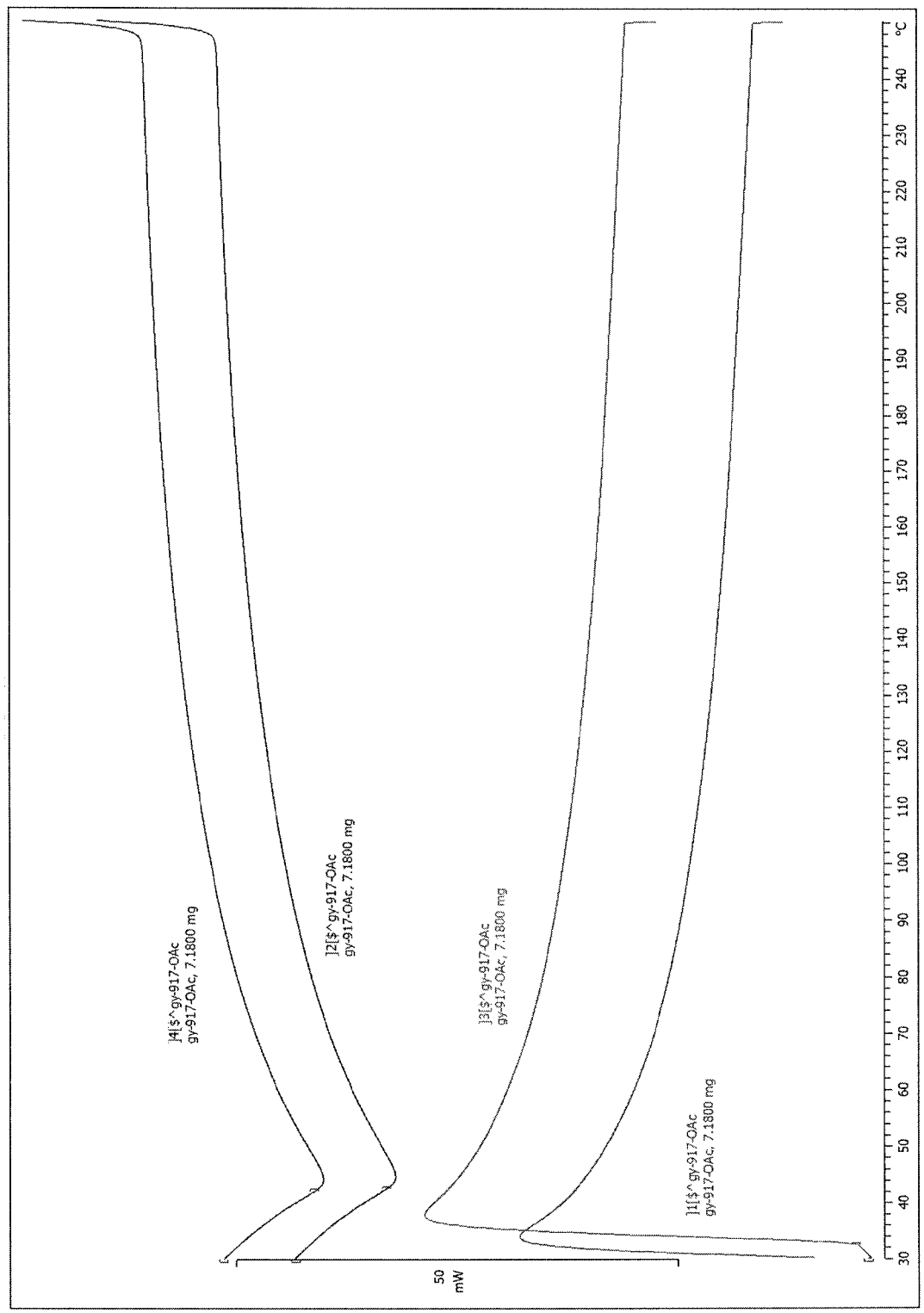
FIG. 21A provides a DSC curve of pDCPD-OAc (the polymer of a compound of Formula 14).

DSC curve of a polymer of compound of Formula 14 is provided in FIG. 21A.

Figure 21B:
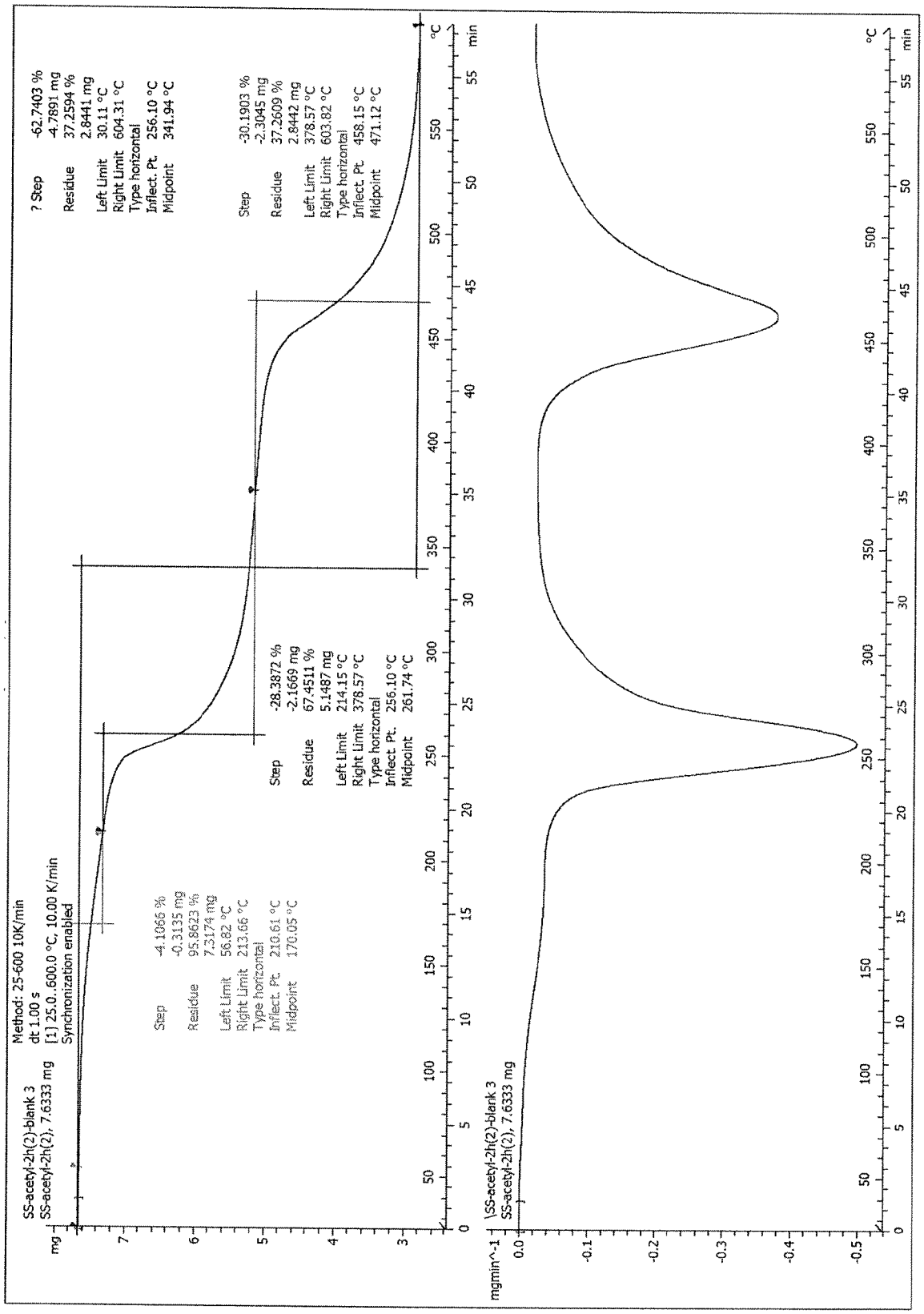
FIG. 21B provides a TGA curve of pDCPD-OAc (the polymer of a compound of Formula 14), after 2 hours of curing.

TGA curve of a polymer of compound of Formula 14, after 2 hours of curing, is provided in FIG. 21B.

B.
Polymerization of Compound of Formula 5 (DCPD-OCH$_2$pH)

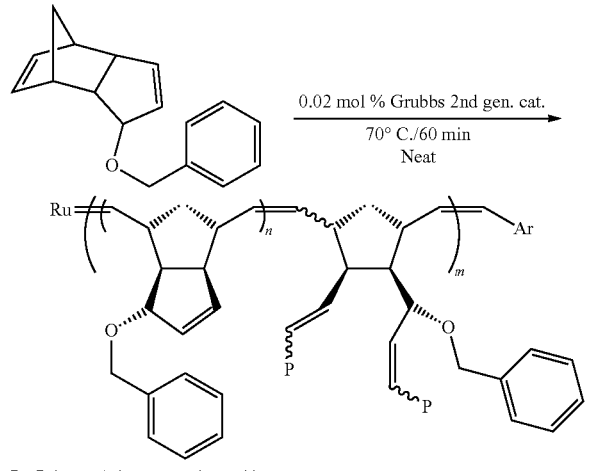

P = Polymer chain, Ar = catalyst residue

Polymerization of compound of Formula 5 (DCPD-OCH$_2$Ph) was carried out according to the following procedure:

The monomer (compound of Formula 5 (DCPD-OCH$_2$Ph)) (600 mg, 2.52 mmol) was introduced to a 4 ml glass vial and then $2^{nd}$ generation Grubbs' catalyst (0.43 mg, 5.04×10$^{-4}$ mmol) dissolved in a small amount of dry CH$_2$Cl$_2$ (~100 μl) was added. After mixing the solution very quickly, the solvent was removed by gentle blowing of argon and the remaining mixture was distributed into three rectangular shaped (2 cm×1 cm×mm) aluminum molds and placed in an oven of pre-set temperature at 70° C. for 60 minutes to produce the odorless cross-linked solid polymer pDCPD-OCH$_2$Ph.

Figure 22:
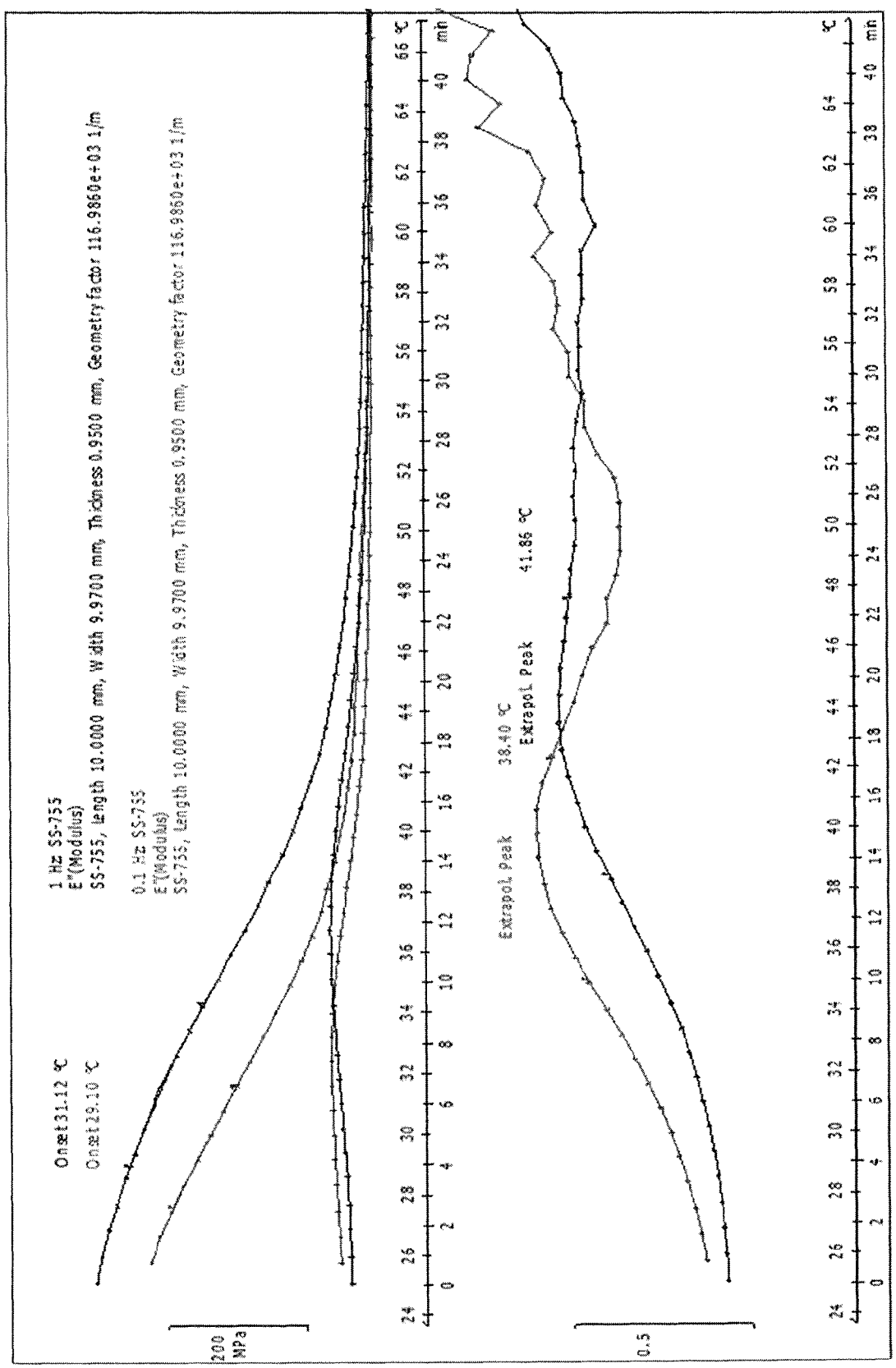
FIG. 22 provides a DMA plot for pDCPD-OCH$_2$Ph (the polymer of compound of Formula 5).

The viscoelastic properties of the pDCPD-OCH$_2$Ph were evaluated from 25° C. to lowest storage modulus (E') temperature with the heating rate of 1° C./min using dynamic mechanical analysis (DMA) (METTLER TOLEDO DMA 1 STARe system) at different frequencies e.g. 0.1 Hz and 1 Hz while experimental results were evaluated using the STAR$^e$ software version 14.00. DMA plot for pDCPD-OCH$_2$Ph is provided in FIG. 22. The values of the storage modulus (E'), loss modulus (E") and loss tangent (tan δ=E"/E') for multiple frequencies were mea-sured as a function of temperature. The glass transition temperatures (T$_g$) attendant with the a peaks are commonly defined either from the onset of the decrease of the modulus or from the tan δ peak. The T$_g$ on the onset curve elucidates the mechanical softening useful for load-bearing applications while tan δ indicates the maximum mobility. T$_g$ values obtained at different frequencies are summarized in Table 3.

TABLE 3

| 0.1 Hz | | 1 Hz | |
|---|---|---|---|
| Onset (Tg) (° C.) | tan δ (° C.) | Onset (Tg) (° C.) | tan δ (° C.) |
| 29.10 | 38.40 | 31.12 | 41.86 |

C.
Polymerization of compound of Formula 11 (DCPD-OBz) was carried out according to the following procedure:

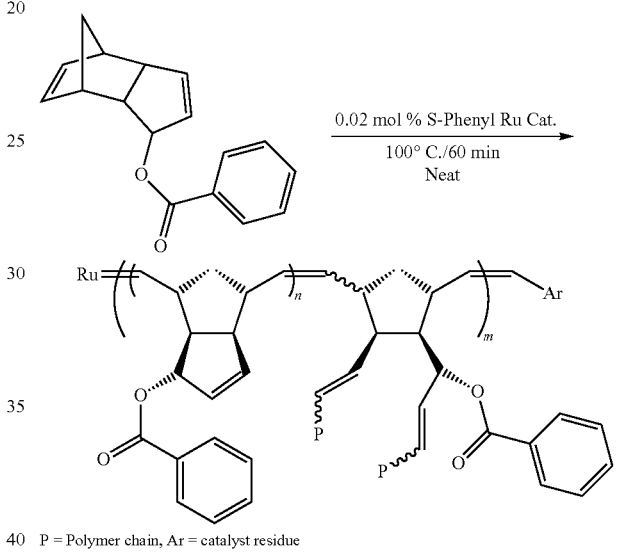

P = Polymer chain, Ar = catalyst residue

Polymerization of compound of Formula 11 was more challenging as it has a melting point of 70° C. Thus, the compound of Formula 11 was melted at 100° C. in an oven and then it was polymerized at this same temperature. Also in this case a latent sulphur chelated ruthenium catalyst (such as cis-Ru—SPh) had to be used, as compound of Formula 11 instantly polymerized with the Grubbs' $2^{nd}$ generation catalyst at 100° C.

Briefly, 0.252 gr of compound of Formula 11 was melted at 100° C. in an oven and then it was polymerized at this same temperature, using a 0.02 mol % latent sulphur chelated ruthenium catalyst cis-Ru—SPh or cis-Ru—S$^i$Pr (cis-Ru—SPh was predominantly used), described in (a) A. Ben-Asuly, A. Aharoni, C. E. Diesendruck, Y. Vidaysky, I. Goldberg, B. F. Straub and N. G. Lemcoff, Organometallics, 2009, 28, 4652-4655; (b) E. Tzur, E. Ivry, C. E. Diesendruck, Y. Vidaysky, I. Goldberg and N. G. Lemcoff, J. Organomet. Chem., 2014, 769, 24-28, dissolved in a small amount of dry CH$_2$Cl$_2$ (~50 μl). The solvent was removed by evaporation and the mixture was heated to 100° C. for 1 hour.

The obtained polymer was odourless.

Characteristic properties of the resultant polymers were measured using Differential Scanning calorimetry (DSC) technique and by TGA, in order to evaluate the effect of the substituents on the polymers' thermal properties.

Figure 23:
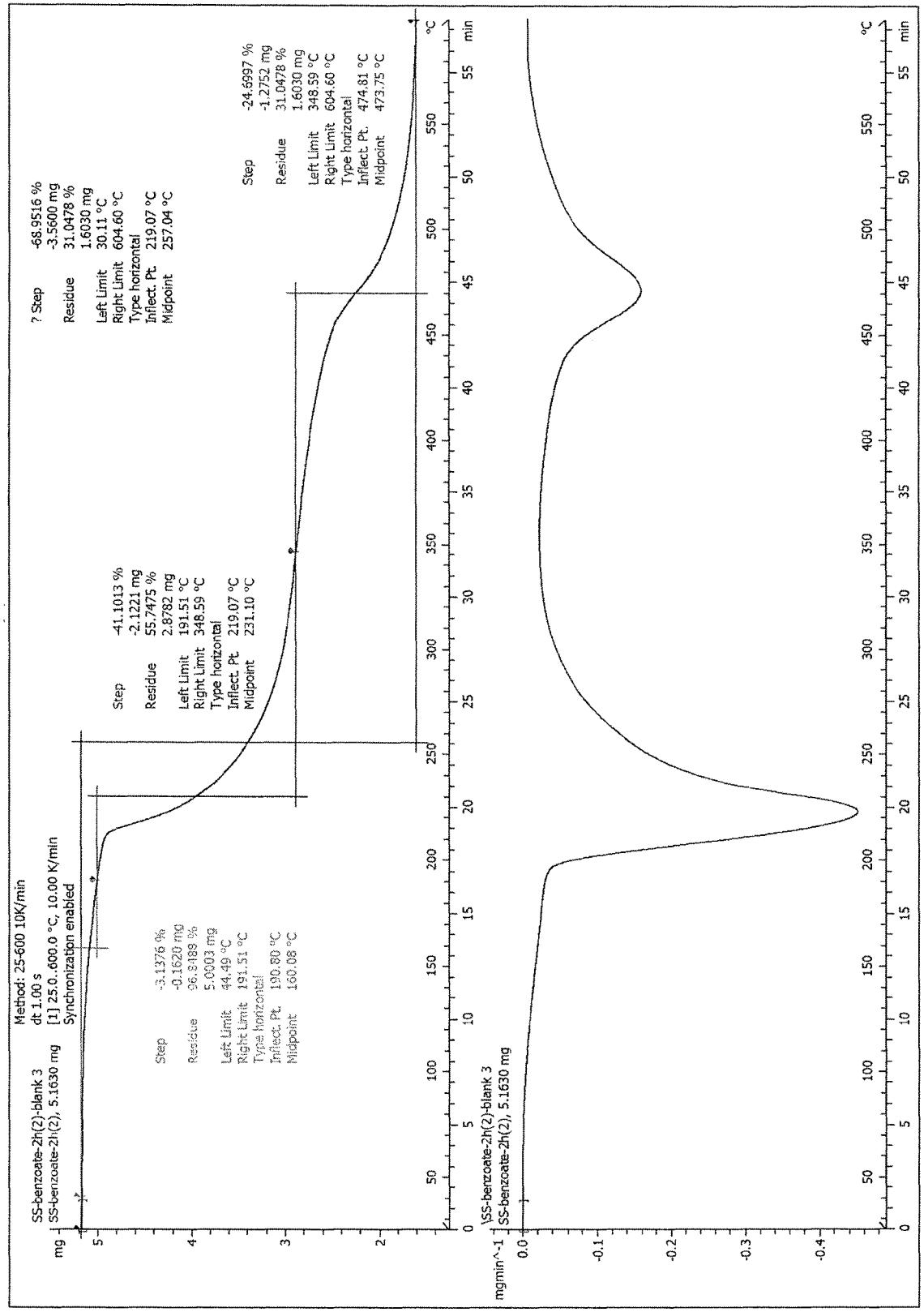
FIG. 23 provides a TGA curve of pDCPD-OBz (the polymer of compound of Formula 11), after 2 hours of curing.

TGA curve of a polymer of compound of Formula 11 is provided in FIG. 23.

Figure 24:
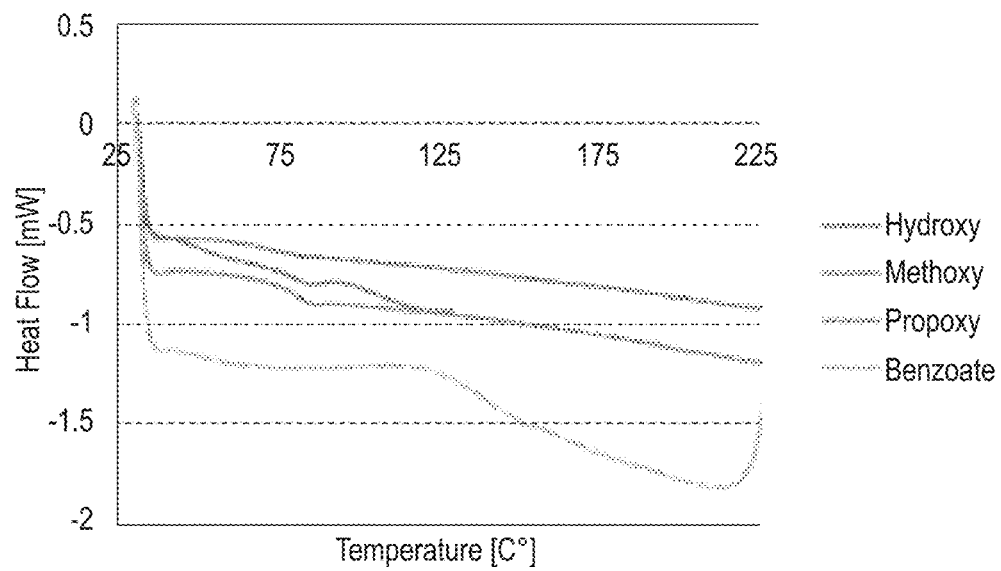
FIG. 24 provides a DSC curve for four pDCPD-OR polymers (OR=—OH, —OMe, —OPr and —OBz), the polymers of DCPD-OH and of compounds of Formulae 1, 3 and 11, respectively.

DSC curve of a polymer of compound of Formula 11, as well as DSC curves of the polymers of DCPD-OH and of compounds of Formulae 1 and 3, are provided in FIG. 24.

D.

Figure 25:
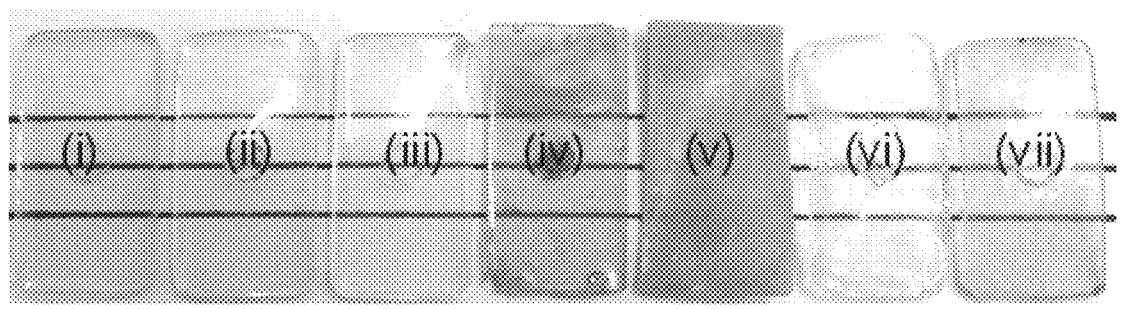
FIG. 25 shows a photograph of the following polymers: (i) pDCPD (the polymer of endo-DCPD), (ii) pDCPD-OH (the polymer of DCPD-OH), (iii) pDCPD-OAc (the polymer of compound of Formula 14), (iv) pDCPD-OBz (the polymer of compound of Formula 11), (v) pDCPD-OMe (the polymer of compound of Formula 1), (vi) pDCPD-OPr (the polymer of compound of Formula 3) and (vii) DCPD-OOc (the polymer of compound of Formula 4). The transparency of the polymers is shown by the lines drawn under the polymers.

Transparency of polymers is important in some applications, such as, for example thin film applications, as well as for containers and formed objects. Therefore, transparency of the polymers of some neutral monomers of general Formulae (I) and (II) was examined. FIG. 25 shows a photograph of the following polymers: (i) pDCPD (the polymer of endo-DCPD), (ii) pDCPD-OH (the polymer of DCPD-OH), (iii) pDCPD-OAc (the polymer of compound of Formula 14), (iv) pDCPD-OBz (the polymer of compound of Formula 11), (v) pDCPD-OMe (the polymer of compound of Formula 1), (vi) pDCPD-OPr (the polymer of compound of Formula 3) and (vii) DCPD-OOc (the polymer of compound of Formula 4). The polymers were obtained as described in sections A and B hereinabove. The transparency of the polymers is shown by the lines drawn under the polymers. As evident from FIG. 25, all of the above polymers are quite transparent except for the polymer of compound of Formula 1 (pDCPD-OMe).

E.

In the TGA, a distinct behavior was observed for the ether derivatives (polymers of some neutral monomers of general Formulae (I)) and the ester derivatives (polymers of some neutral monomers of general Formulae (II)). The hydroxyl and ether derivatives displayed only one distinctive decomposition temperature, while the esters showed two decomposition steps, probably due to breakdown of the side group followed by the main chain decay pathway. Table 4 summarizes the decomposition temperatures of the new polymers. As can be seen from the data in Table 4, the new hydroxyl and ether polymers showed maximum rate decomposition temperatures very similar to that of the parent pDCPD polymer, while the esters showed greater decomposition at lower temperatures. However, pDCPD has greater stability at extreme temperatures, indicating that probably the side chains are being decomposed first.

TABLE 4

Decomposition temperatures obtained from the TGA data for cross-linked polymers

| Polymer | 5% weight loss T (° C.) | 10% weight loss T (° C.) | Main chain max decomposition rate T (° C.) | Ester maximum decomposition rate T (° C.) |
|---|---|---|---|---|
| pDCPD | 212.2 | 451.0 | 474.4 | |
| pDCPD-OH | 187.7 | 230.1 | 469.9 | |
| pDCPD-OAc (the polymer of compound of Formula 14) | 228.7 | 253.0 | 471.1 | 261.7 |
| pDCPD-OBz (the polymer of compound of Formula 11) | 212.8 | 219.0 | 473.8 | 231.1 |
| pDCPD-OMe (the polymer of compound of Formula 1) | 181.0 | 217.1 | 463.4 | |
| pDCPD-OPr (the polymer of compound of Formula 3) | 219.4 | 253.8 | 467.1 | |
| pDCPD-OOc (the polymer of compound of Formula 4) | 196.9 | 250.0 | 466.7 | |

F.

DSC analyses in Table 5 show that substitutions on DCPD significantly decreased the Tg of the resultant polymers compared to the parent pDCPD, ranging from ~80° C. for pDCPD-OMe (the polymer of compound of Formula 1), up to ~143° C. for pDCPD-OBz (the polymer of compound of Formula 11). For pDCPD-OOc (the polymer of compound of Formula 4) and pDCPD-OAc (the polymer of compound of Formula 14), no Tg values were found, neither at high temperatures nor by cooling to −100° C.

TABLE 5

Glass transition temperatures from DSC analysis

| Polymer | Tg (° C.) |
|---|---|
| pDCPD | 163.3 |
| pDCPD-OH | 83.5 |
| pDCPD-OAc (the polymer of compound of Formula 14) | N.A |
| pDCPD-OBz (the polymer of compound of Formula 11) | 142.9 |
| pDCPD-OMe (the polymer of compound of Formula 1) | 79.6 |
| pDCPD-OPr (the polymer of compound of Formula 3) | 80.9 |
| pDCPD-OOc (the polymer of compound of Formula 4) | N.A |

Unlike all other polymers which formed stiff solid materials, pDCPD-OOc appeared as a very flexible and elastic, stretchable polymer. pDCPD-OAc was also relatively soft, although not as flexible as the octyl-ether (the polymer of compound of Formula 4).

G.

The following wetting experiment was performed in order to understand the hydrophilic and hydrophobic nature of the polymers:

Polymers of pDCPD-OH, pDCPD-OPr (the polymer of compound of Formula 3) and a copolymer of both pDCPD-OH and pDCPD-OPr, were prepared in a 4 ml glass vial. The copolymer was prepared by mixing DCPD-OH and DCPD-OPr in a 50/50 ratio. All polymers were prepared following the general polymerization procedure detailed in section A hereinabove. After polymerization was completed the vial was broken and the polymer removed. 30 μl deionized water were added to the top of each of the polymers and a snapshot was taken after a few minutes.

Figure 26:
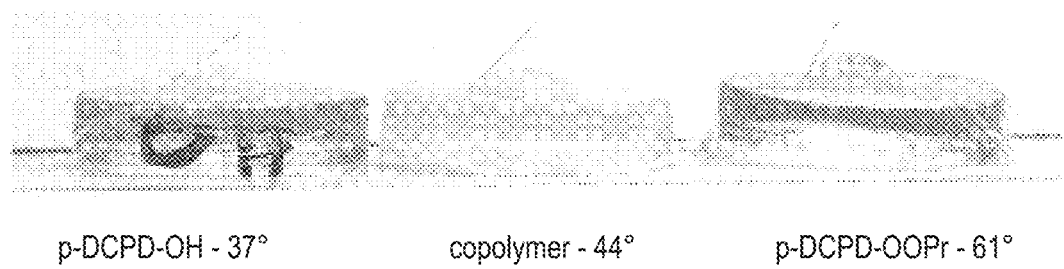
FIG. 26 provides an image for wetting of pDPCD-OH (the polymer of DCPD-OH), co-(pDCPD-OH-pDCPD-OPr) (co-polymer of pDPCD-OH and pDCPD-OPr), and pDCPD-OPr (the polymer of compound of Formula 3).
Figure 27:
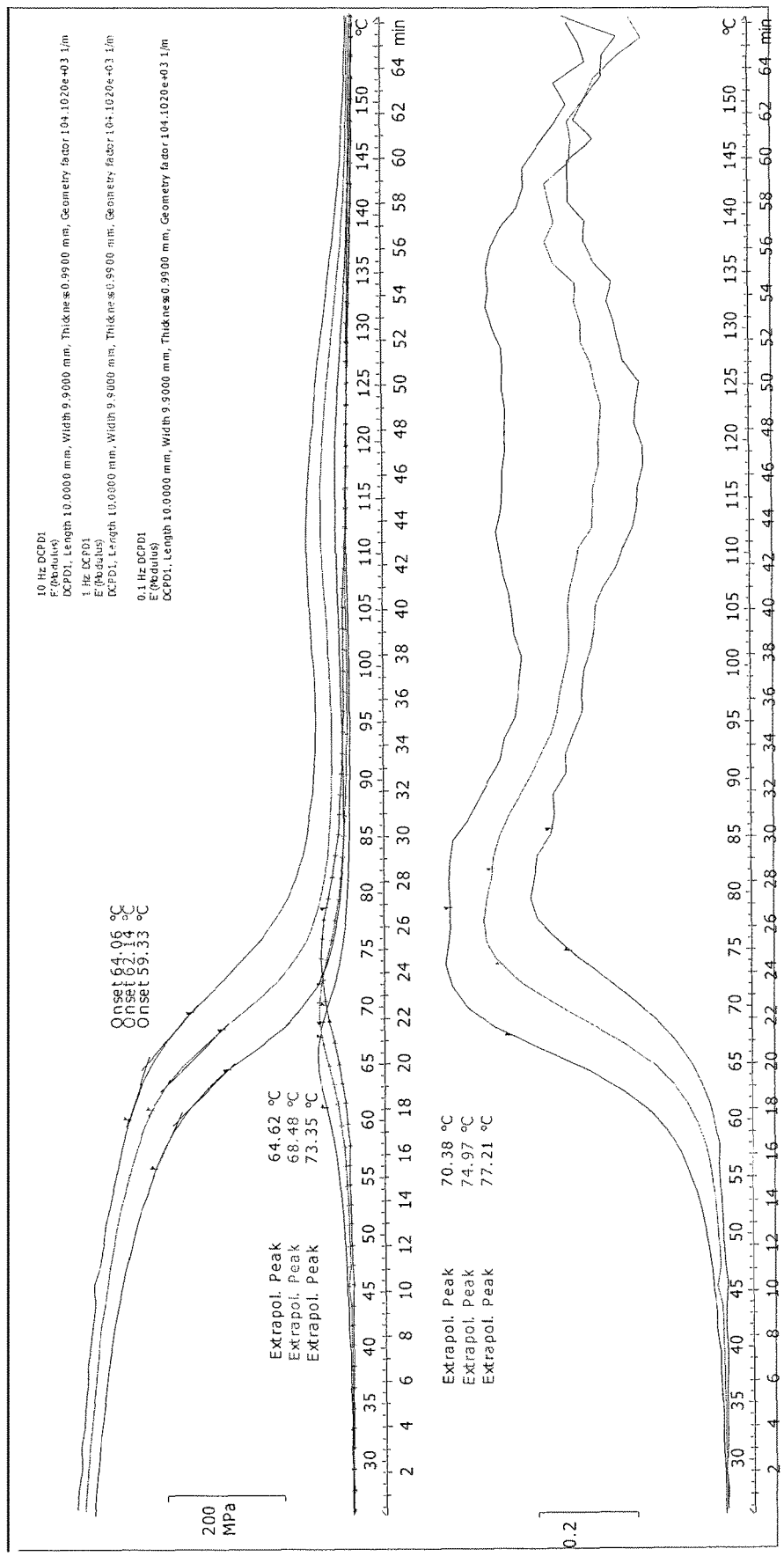
FIG. 27 provides a DMA plot for pDCPD (the polymer of endo-DCPD). DMA storage tensile modulus E' and mechanical loss factor tan δ as a function of temperature for pDCPD.
Figure 28:
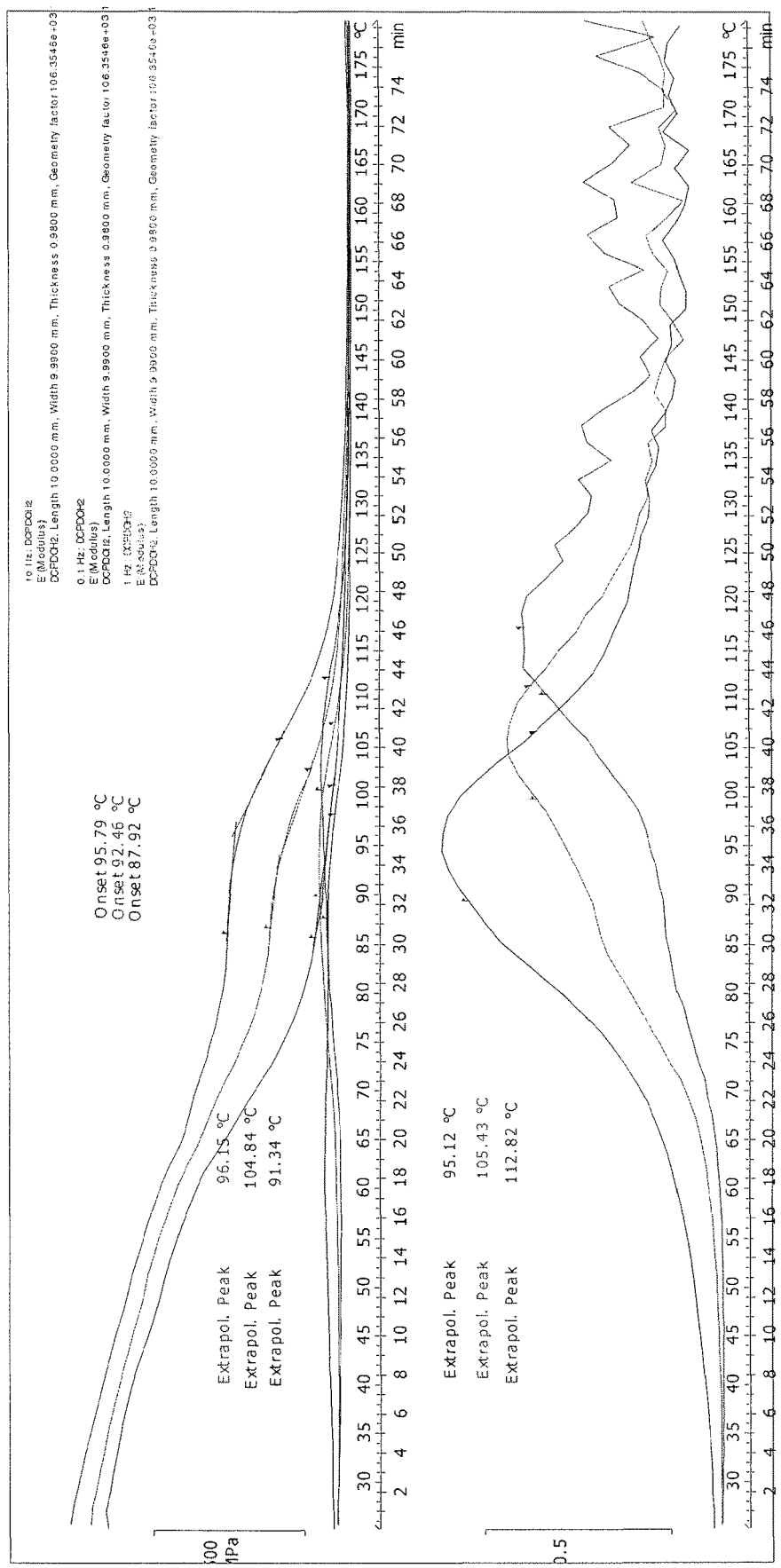
FIG. 28 provides a DMA plot for pDCPD-OH the polymer of DCPD-OH). DMA storage tensile modulus E' and mechanical loss factor tan δ as a function of temperature for pDCPD-OH.
Figure 29:
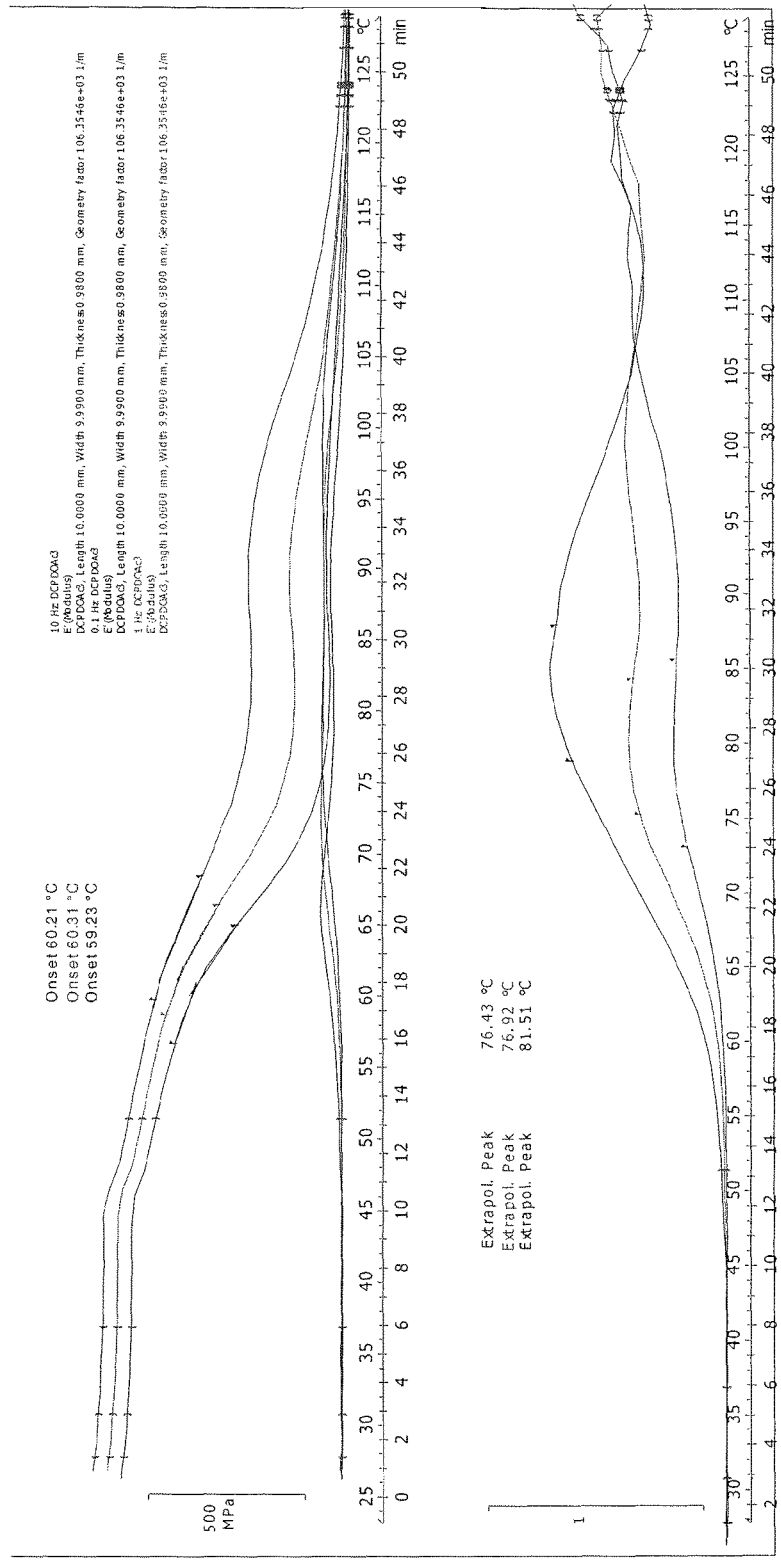
FIG. 29 provides a DMA plot for pDCPD-OAc (the polymer of compound of Formula 14). DMA storage tensile modulus E' and mechanical loss factor tan δ as a function of temperature for pDCPD-OAc.
Figure 30:
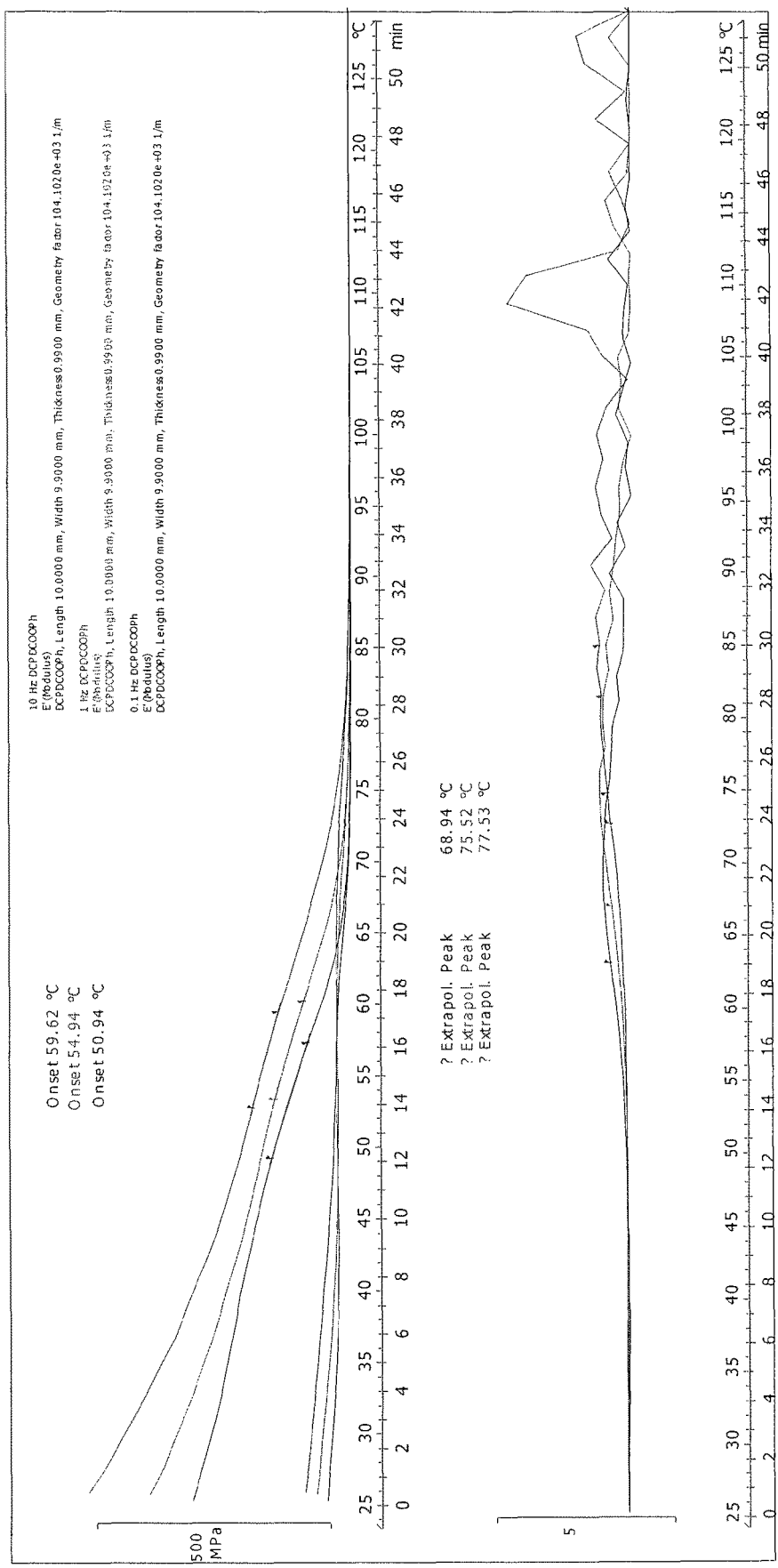
FIG. 30 provides a DMA plot for pDCPD-OBz (the polymer of compound of Formula 11). DMA storage tensile modulus E' and mechanical loss factor tan δ as a function of temperature for pDCPD-OBz.
Figure 31:
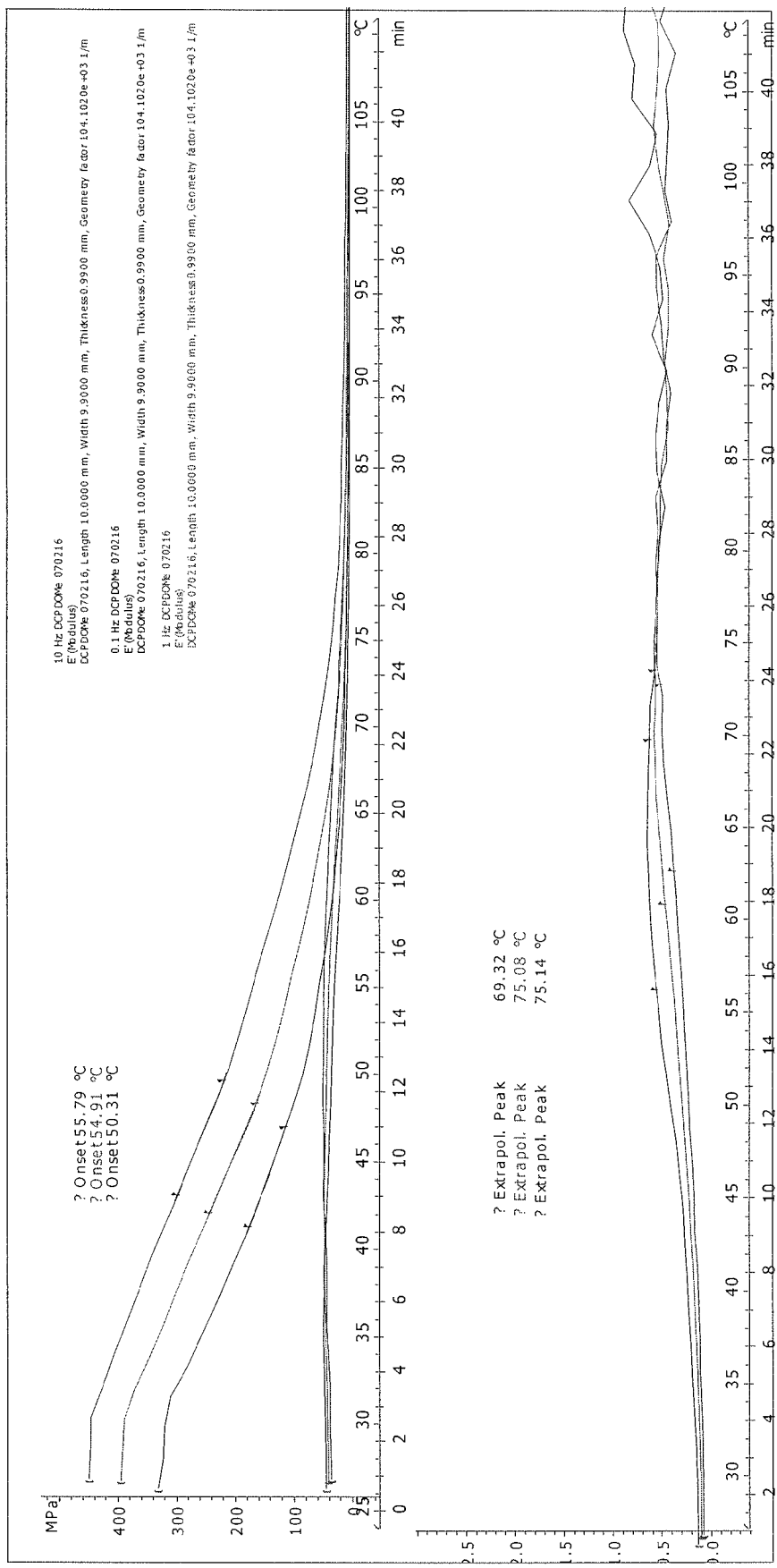
FIG. 31 provides a DMA plot for pDCPD-OMe (the polymer of compound of Formula 1). DMA storage tensile modulus E' and mechanical loss factor tan δ as a function of temperature for pDCPD-OMe.
Figure 32:
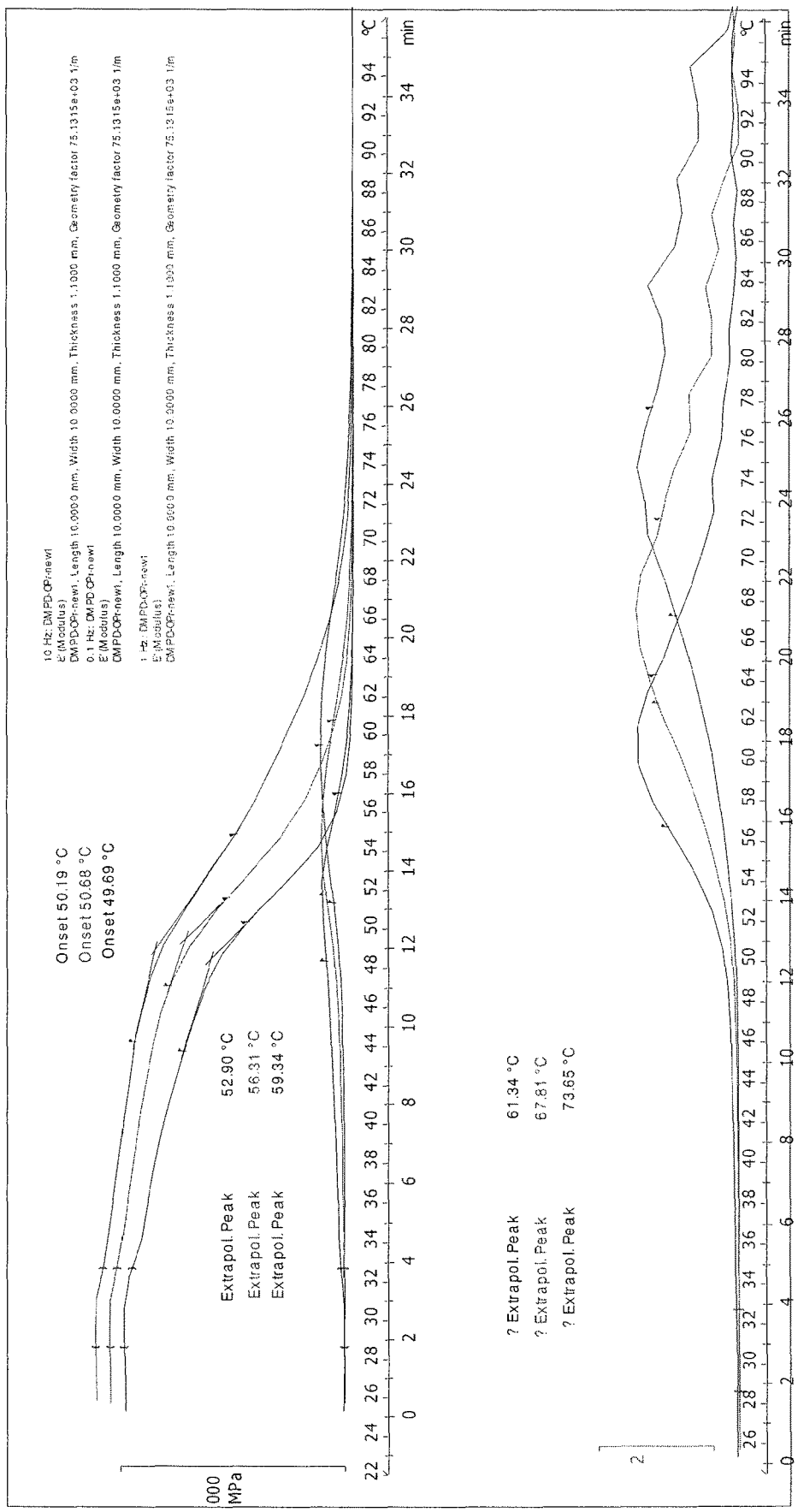
FIG. 32 provides a DMA plot for pDCPD-OPr (the polymer of compound of Formula 3). DMA storage tensile modulus E' and mechanical loss factor tan δ as a function of temperature for pDCPD-OPr.
Figure 33:
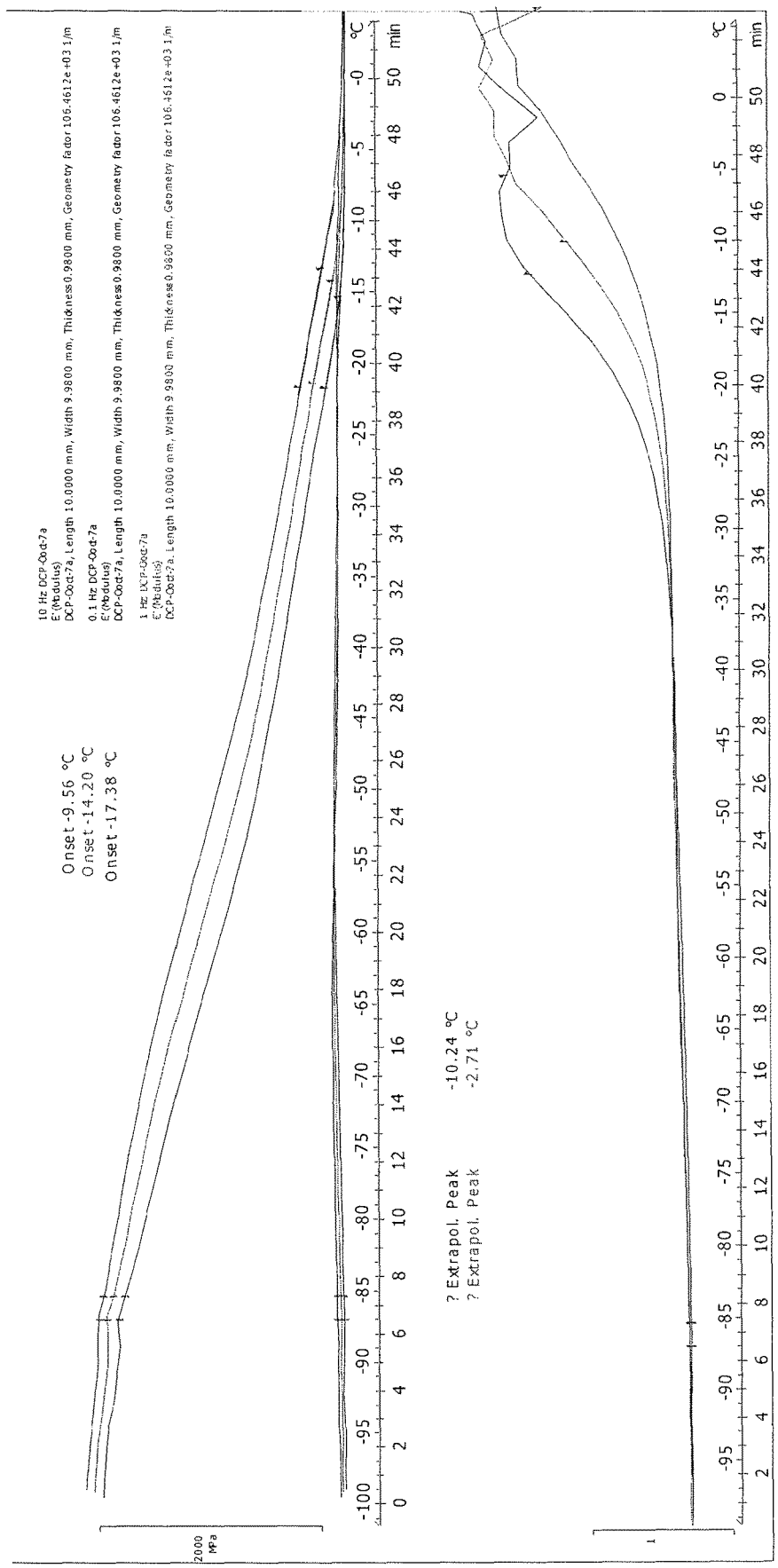
FIG. 33 provides a DMA plot for pDCPD-OOct (the polymer of compound of Formula 4). DMA storage tensile modulus E' and mechanical loss factor tan δ as a function of temperature for pDCPD-OOc.

A qualitative wetting contact angle test on pDCPD-OH, pDCPD-OPr (the polymer of compound of Formula 3) and a copolymer of both, nicely showed how changing the functional group of the monomer can affect the hydrophilic properties of the surface as expected. The image for wetting of pDPCD-OH, co-(pDCPD-OH-pDCPD-OPr) and pDCPD-OPr is provided in FIG. 26. The lines are visual aids, the differences in the contact angles are quite apparent. H.

In order to further study the thermal properties of the polymers, dynamic mechanical analysis (DMA) of the samples were performed at various fixed frequencies as a function of temperature to obtain the storage modulus (E'), loss modulus (E") and the tangent modulus (tan $\delta$=E"/E'). The glass transition temperatures (Tg) attendant with the a peaks are commonly defined either from the onset of the decrease of the E modulus or from the tan $\delta$ peak. The Tg on the onset curve elucidates the mechanical softening useful for load-bearing applications. These Tg values obtained at different frequencies are summarized in Table 6.

TABLE 6

Onset Tg and tan $\delta$ values obtained from DMA measurement

| | (10 Hz) | | (1 Hz) | | (0.1 Hz) | |
|---|---|---|---|---|---|---|
| Sample name | Onset Tg (° C.) | Tan $\delta$ Tg (° C.) | Onset Tg (° C.) | tan $\delta$ Tg (° C.) | Onset Tg (° C.) | tan $\delta$ Tg (° C.) |
| pDCPD | 64.0 | 77.2 | 62.1 | 75.0 | 59.3 | 70.4 |
| pDCPD-OH | 95.8 | 112.8 | 92.5 | 105.4 | 87.9 | 95.1 |
| pDCPD-OAc (the polymer of compound of Formula 14) | 59.7 | 77.1 | 59.5 | 75.2 | 59.4 | 83.4 |
| pDCPD-OBz (the polymer of compound of Formula 11) | 59.6 | 77.5 | 54.9 | 75.5 | 50.9 | 68.9 |
| pDCPD-OMe (the polymer of compound of Formula 1) | 42.3 | 52.7 | 39.3 | 58.7 | 37.8 | 62.7 |
| pDCPD-OPr (the polymer of compound of Formula 3) | 50.2 | 73.7 | 50.7 | 67.8 | 49.7 | 61.3 |
| pDCPD-OOc (the polymer of compound of Formula 4) | −9.6 | — | −14.2 | −2.7 | −17.4 | −10.2 |

As observed from the values in Table 6, glass transition temperatures were quite different from the Tg values obtained by DSC experiments because of the applied mechanical forces. Table 6 shows that the new polymer pDCPD-OH (the polymer of DCPD-OH) has the highest Tg values, while rubbery pDCPD-OOc (the polymer of compound of Formula 4) has the lowest. The DMA curves for each polymer are depicted in FIGS. 27-33. Overall it can be observed that the new polymers display thermal properties that fall in line with the parent polydicyclopentadiene material produced by the same ruthenium catalyst. Thus, it has now been shown that the new polymers disclosed herein possess useful physical properties, while lacking the irritating odour of the dicyclopentadiene parent monomer.

Example 13

Formation and Comparison of Linear and Cross-Linked Polymer Films of Neutral Monomers of Formula (I) and (II)

The formation of cross-linked polymers was studied by carrying out infrared spectroscopy analyses on polymer films prepared with Grubbs' $1^{st}$ and $2^{nd}$ generation catalysts. It has been reported that the use of Grubbs' $1^{st}$ generation catalyst leads to linear polymers with DCPD derivatives at low temperatures (Gong L. et al. RSC Adv., 2015, 5, 26185-26188), and it has also been shown that the catalyst devoid of the N-heterocyclic carbene ligand is much less reactive in reactions with doubly substituted olefins (such as the cyclopentene moiety in DCPD) (S. Elmer, N. G. Lemcoff and S. C. Zimmerman, Macromolecules, 2007, 40, 8114-8118). Thus, it was surmised that $1^{st}$ generation catalysts would give more linear polymers, while $2^{nd}$ generation catalysts should give more cross-linked material.

Thin polymer films were produced according to the following general procedure: 20 mg of monomer were mixed with 0.03 mg of ruthenium catalyst dissolved in 30 μL of dry $CH_2Cl_2$. The mixture was transferred onto microscope slide and was covered with second slide. Air bubbles were removed by applying pressure on the slides. For linear polymer films: Grubbs 1st generation catalyst was used [CAS Number 172222-30-9, Grubbs Catalyst, $1^{st}$ Generation purchased from Sigma-Aldrich]. The setup was kept at RT (25° C.) for 2 hours. For cross-linked polymer films: Grubbs' $2^{nd}$ generation catalyst was used [as specified hereinabove in Example 12A]. The setup was kept at 70° C. for 30 minutes.

All of the polymers thus formed were subjected to solubility testing in several organic solvents, including THF, ethyl acetate, chloroform, methylene chloride. It was found that the above-identified linear polymer films were soluble in organic solvents, whereas the above-identified cross-linked polymer films were insoluble in organic solvents. Without being bound by theory it is believed that the insolubility of the polymers made with the Grubb's $2^{nd}$ generation catalyst, in regular organic solvents, provides a proof for the formation of cross-linked polymers.

All films thus formed were analysed by FTIR.

Figure 34:
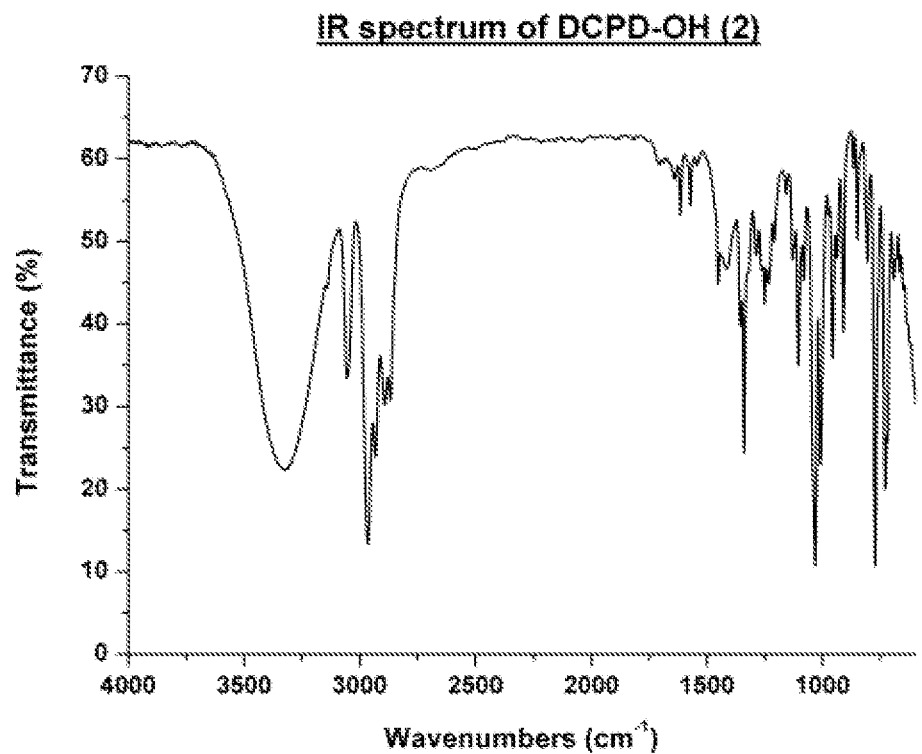
FIG. 34 provides the FTIR for DCPD-OH monomer.

A FTIR spectrum for DCPD-OH monomer is provided in FIG. 34.

Figure 35:
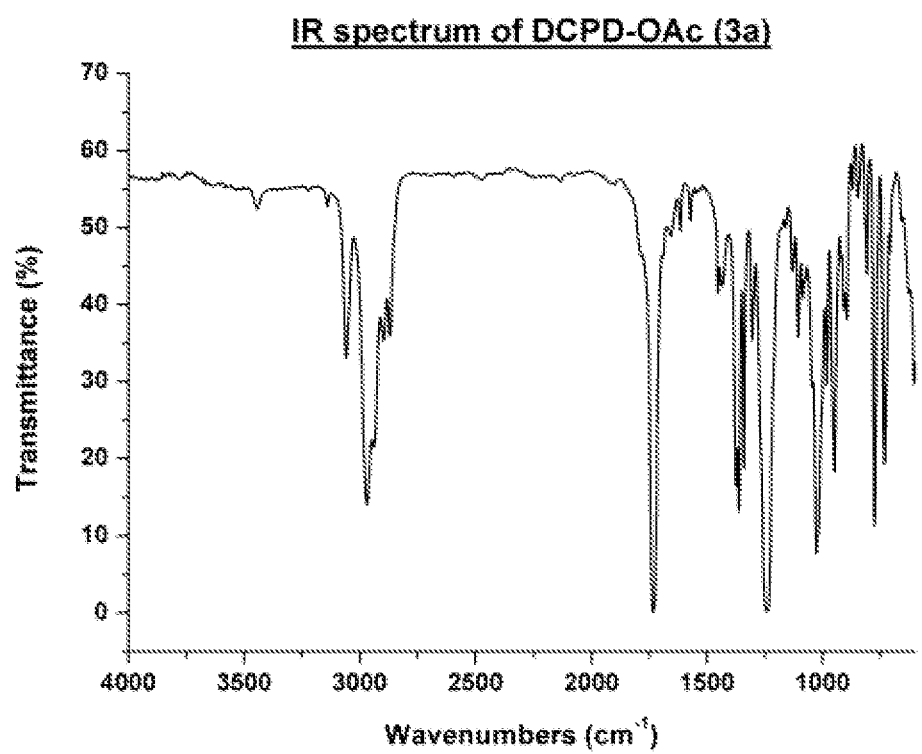
FIG. 35 provides the FTIR for DCPD-OAc monomer (compound of formula 14).

A FTIR spectrum for DCPD-OAc monomer (compound of Formula 14) is provided in FIG. 35.

Figure 36:
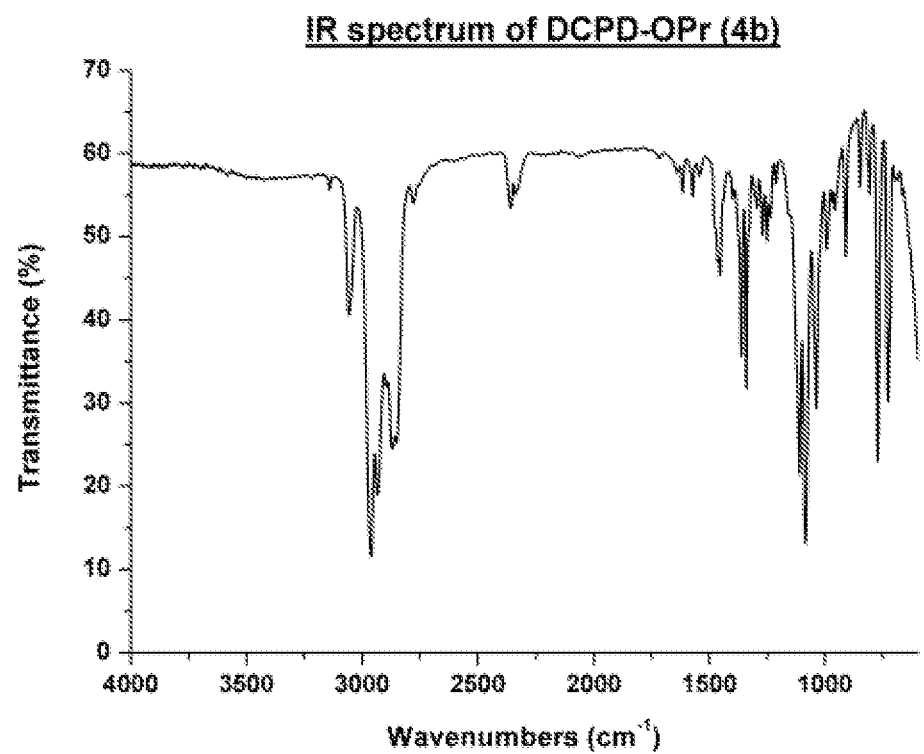
FIG. 36 provides the FTIR for DCPD-OPr monomer (compound of Formula 3).

A FTIR spectrum for DCPD-OPr monomer (compound of Formula 3) is provided in FIG. 36.

Figure 37:
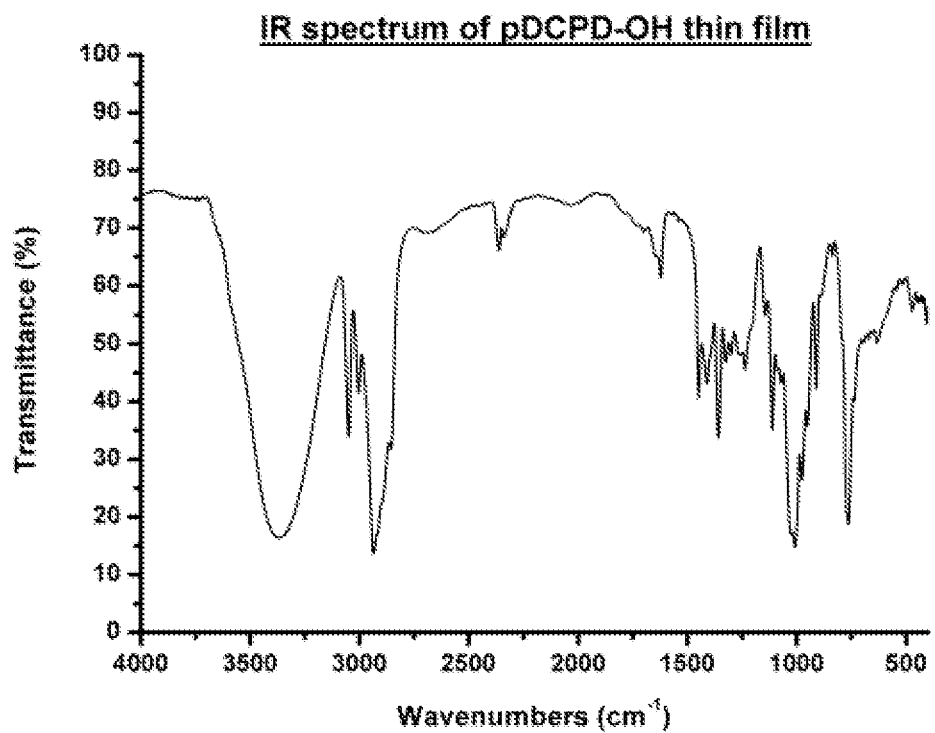
FIG. 37 provides the FTIR for cross-linked pDCPD-OH thin film (the polymer of DCPD-OH).

A FTIR spectrum for cross-linked pDCPD-OH thin film (the polymer of DCPD-OH) is provided in FIG. 37.

Figure 38:
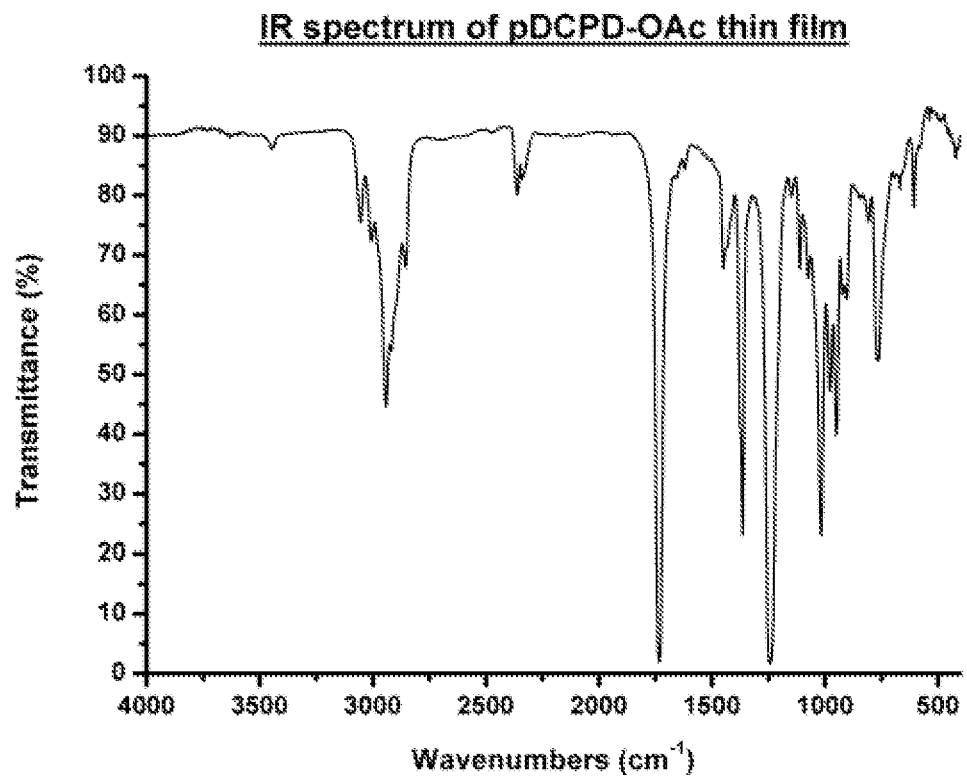
FIG. 38 provides the FTIR for cross-linked pDCPD-OAc thin film (the polymer of compound of Formula 14).

A FTIR spectrum for cross-linked pDCPD-OAc thin film (the polymer of compound of Formula 14) is provided in FIG. 38.

Figure 39:
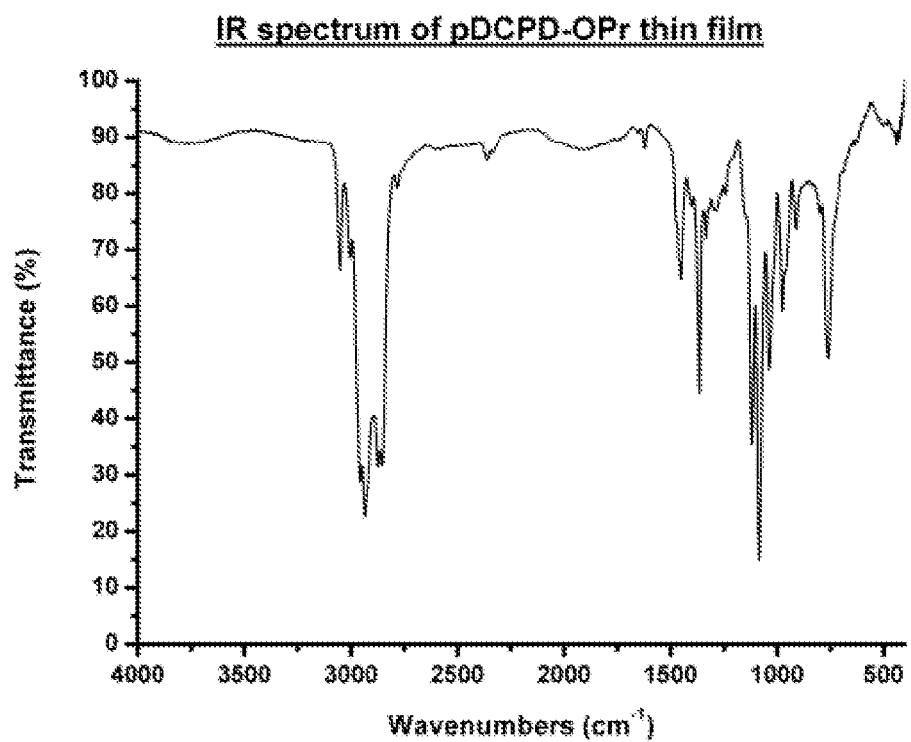
FIG. 39 provides the FTIR for cross-linked pDCPD-OPr thin film (the polymer of compound of Formula 3).

A FTIR spectrum for cross-linked pDCPD-OPr thin film (the polymer of compound of Formula 3) is provided in FIG. 39.

Figure 40:
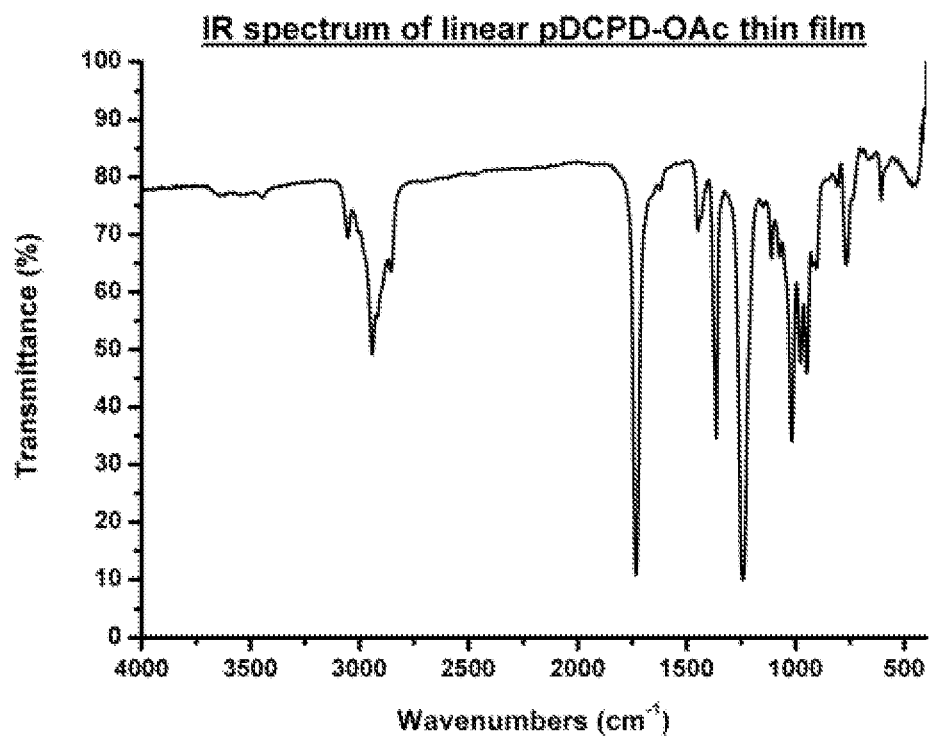
FIG. 40 provides the FTIR for linear pDCPD-OAc thin film (the polymer of compound of Formula 14).

A FTIR spectrum for linear pDCPD-OAc thin film (the polymer of compound of Formula 14) is provided in FIG. 40.

Figure 41:
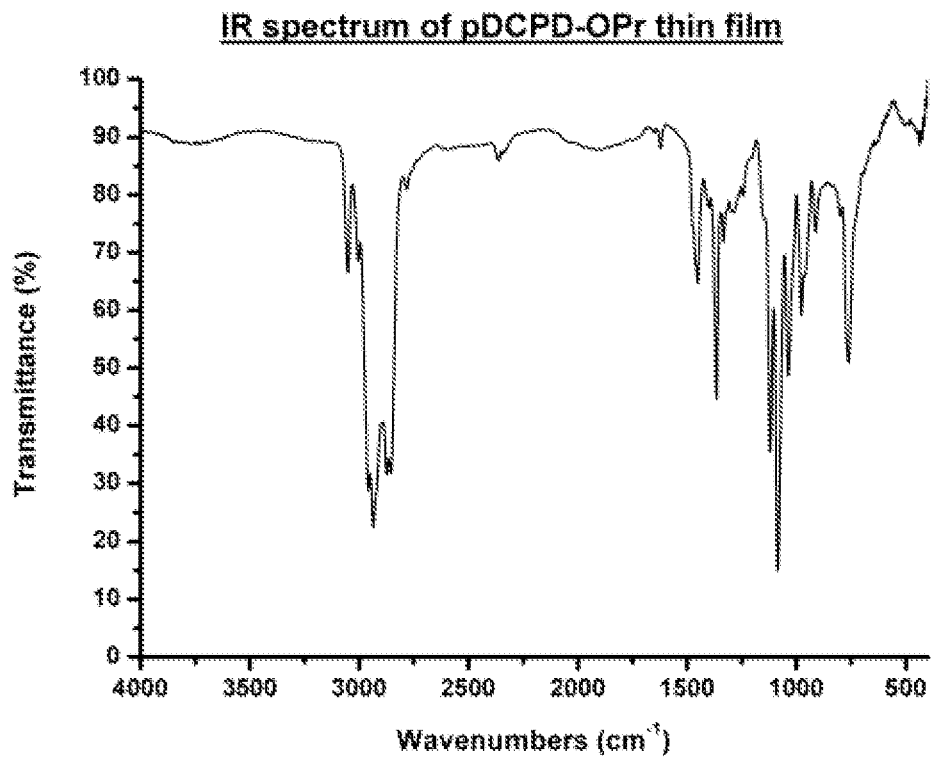
FIG. 41 provides the FTIR for linear pDCPD-OPr thin film (the polymer of compound of Formula 3).

A FTIR spectrum for linear pDCPD-OPr thin film (the polymer of compound of Formula 3) is provided in FIG. 41.

Figure 42:
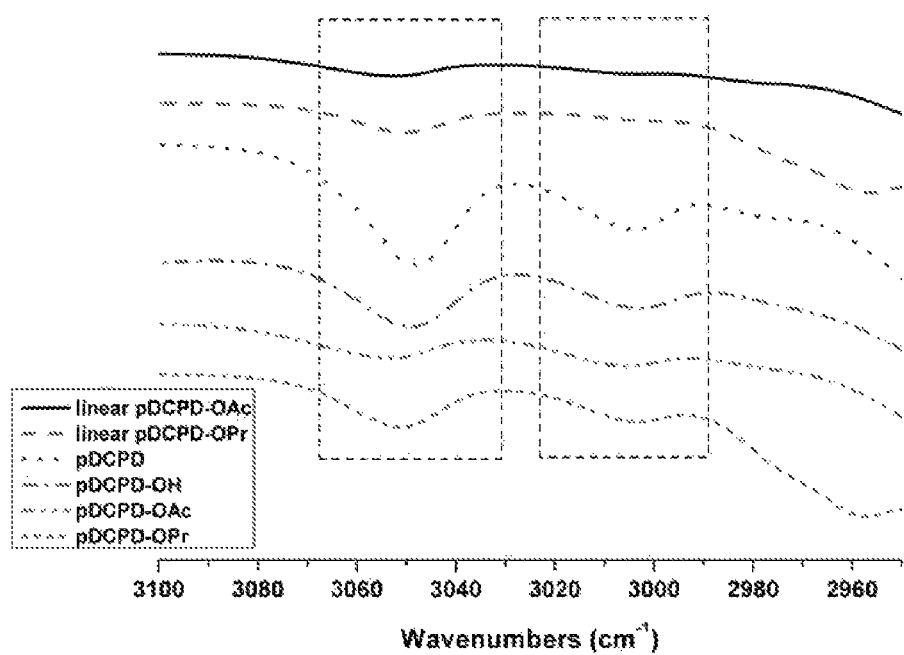
FIG. 42 shows the expanded FTIR spectra for polymeric films obtained using Grubb's $1^{st}$ and $2^{nd}$ generation catalysts.

Careful observation of the expanded spectra (3100-2950 $cm^{-1}$ region), shows that the IR absorption bands at ~3000 $cm^{-1}$ (assigned to =C—H acyclic bond) were present only for polymers made with the Grubb's $2^{nd}$ generation catalyst and almost negligible for those made with the Grubb's $1^{st}$ generation catalyst. FIG. 42 shows the expanded FTIR spectra for polymeric films obtained using Grubb's $1^{st}$ and $2^{nd}$ generation catalysts. The presence of an absorption band around 3000 $cm^{-1}$ is indicative of cross-linking.

Example 14

Polymerization of Some Ionic Monomers of Formula (I) and (II)

Polymerization of ionic monomers of general Formulae (I) and (II) was carried out according to the following procedure:

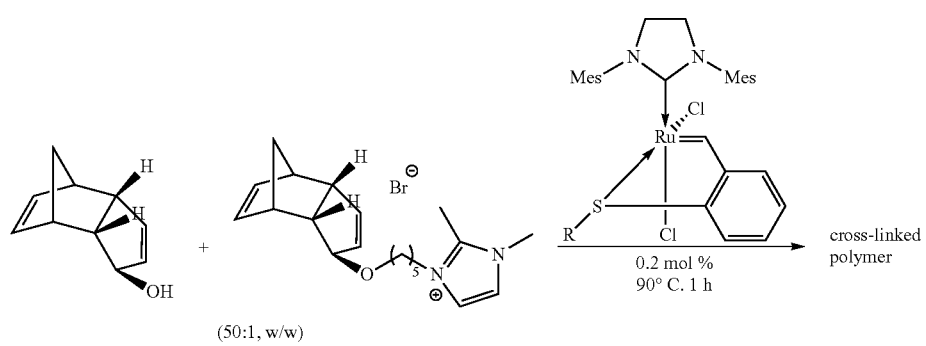

(50:1, w/w)

A mixture of hydroxydicyclopentadiene (200 mg, 1.35 mmol), ionic monomer (4 mg, 0.0105 mmol) and cis-phenyl-sulfur chelated ruthenium catalyst as shown in the scheme above (R in the cis-phenyl-sulfur chelated ruthenium catalyst is phenyl), described in Kost, T. et al, *Journal of Organometallic Chemistry*, 2008, 693, 2200-2203, (1.84 mg, 2.72 µmol) were dissolved in 100 µl of dry CHCl$_3$. Then solvent was removed by vacuum and the reaction mixture was placed in oven at 90° C. for 1 hour to get the covalent ionic crossed linked polymer.

Example 15

Polymerization Assisted with Catalysts Responsive to UV Irradiation

Polymerization of DCPD-OH was carried out with a catalyst responsive to UV irradiation according to the following procedure:

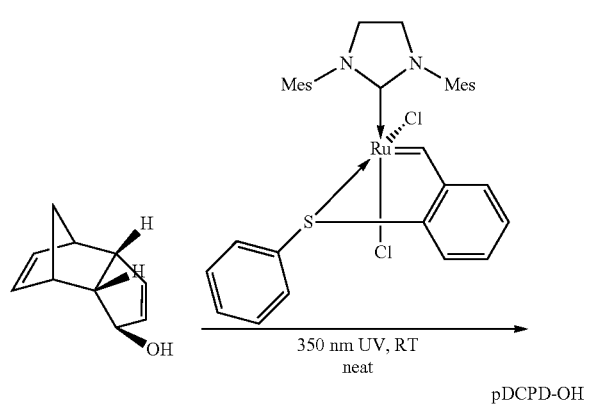

In a 4-ml vial, 0.228 g of DCPD-OH was mixed with 0.31 mg of S-Phenyl-Ru catalyst as shown in the scheme, (as ca. 20 methylene chloride solution). The solvent was evaporated and the mixture was layered on a template having dimensions 20 mm×10 mm×1 mm. The template was irradiated with 350-nm UV light for 1:40 hours, at room temperature. A hard cross-linked polymer was obtained.

The invention claimed is:

1. A crosslinked polymer or copolymer formed by polymerizing a compound of Formula (I):

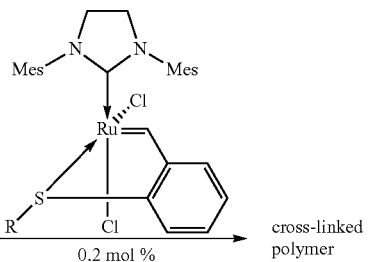

Formula (I)

wherein:

R is selected from the group consisting of a linear or branched alkyl (C$_n$H$_{2n+1}$); an aryl; an alkylaryl; a positively charged nitrogen-containing group in which case the compound of Formula I is provided in a form of a salt with a suitable counter-ion, wherein the positively charged nitrogen may form part of a ring system; CH$_2$—O-dicyclopentadiene; and an ester-forming group of a general formula —C(O)—R'; wherein R' is independently selected from the group consisting of a linear or branched alkyl (C$_n$H$_{2n+1}$), substituted or unsubstituted aryl; and a positively charged nitrogen-containing group, wherein the positively charged nitrogen may form part of a ring system; and the crosslinked polymer or copolymer is formed using a (1,3-Bis-(2,4,6-trimethylphenyl)-2-imidazolidinylidene)dichloro-(phenylmethylene)(tricyclohexylphosphine)ruthenium catalyst or a sulfur chelated ruthenium catalyst.

2. The crosslinked polymer or copolymer according to claim 1, having Formula (V)

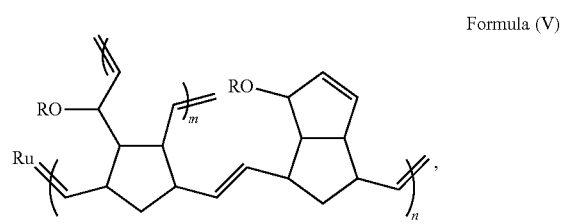

Formula (V)

wherein:
n indicates a degree of polymerization and m indicates a degree of cross-linking;
m is not zero; and
Ru is a catalyst residue.

3. The crosslinked polymer or copolymer according to claim 1, wherein R is a linear or branched alkyl ($C_nH_{2n+1}$).

4. The crosslinked polymer or copolymer according to claim 1, wherein R is an aryl.

5. The crosslinked polymer or copolymer according to claim 1, wherein R is an alkylaryl.

6. The crosslinked polymer or copolymer according to claim 1, wherein R is a positively charged nitrogen-containing group in which case the compound of Formula I is provided in a form of a salt with a suitable counter-ion, and wherein the positively charged nitrogen may form part of a ring system.

7. The crosslinked polymer or copolymer according to claim 1, wherein R is $CH_2$—O-dicyclopentadiene.

8. The crosslinked polymer or copolymer according to claim 1, wherein R is an ester-forming group of a general formula —C(O)—R';
wherein R' is independently selected from the group consisting of a linear or branched alkyl ($C_nH_{2n+1}$), substituted or unsubstituted aryl, and a positively charged nitrogen-containing group in which case the compound of Formula I is provided in a form of a salt with a suitable counter-ion, wherein the positively charged nitrogen may form part of a ring system.

9. The crosslinked copolymer according to claim 1, wherein the copolymer is formed by polymerizing a compound of Formula (I) and endo-hydroxydicyclopentadiene (DCPD-OH).

10. The crosslinked polymer or copolymer according to claim 1, wherein the compound of Formula (I) is selected from the group consisting of compounds of Formula 1, Formula 2, Formula 3, Formula 4, Formula 5, Formula 11 and Formula 14:

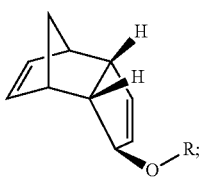

Formula 1

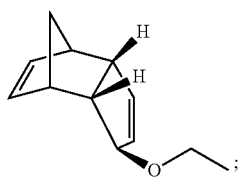

Formula 2

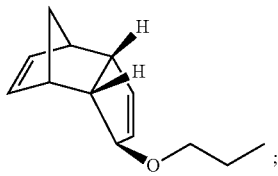

Formula 3

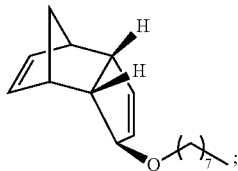

Formula 4

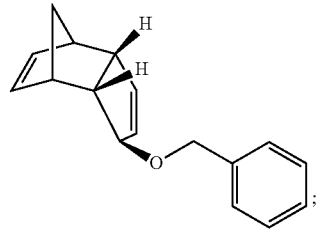

Formula 5

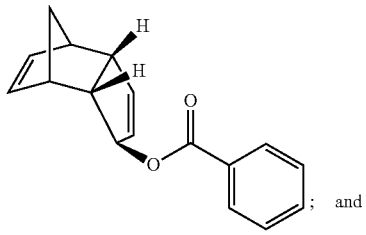

Formula 11
; and

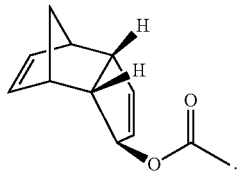

Formula 14

11. The crosslinked copolymer according to claim 10, wherein the copolymer is formed by polymerizing a compound of Formula (I) selected from the group consisting of compounds of Formula 1, Formula 2, Formula 3, Formula 4, Formula 5, Formula 11 and Formula 14; and endo-hydroxydicyclopentadiene (DCPD-OH).

12. The crosslinked copolymer according to claim 11, formed by polymerizing a compound of Formula 3 and endo-hydroxydicyclopentadiene (DCPD-OH).

* * * * *

UNITED STATES PATENT AND TRADEMARK OFFICE
CERTIFICATE OF CORRECTION

PATENT NO. : 11,059,939 B2
APPLICATION NO. : 15/769398
DATED : July 13, 2021
INVENTOR(S) : Gabriel N. Lemcoff et al.

Page 1 of 1

It is certified that error appears in the above-identified patent and that said Letters Patent is hereby corrected as shown below:

In the Claims

Column 39, Line 40, Claim 10, Formula 1, " 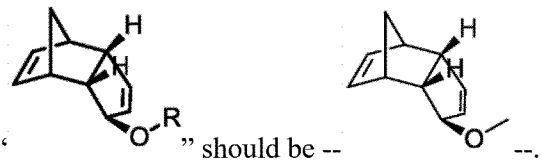 " should be --  --.

Signed and Sealed this
Ninth Day of November, 2021

Drew Hirshfeld
*Performing the Functions and Duties of the
Under Secretary of Commerce for Intellectual Property and
Director of the United States Patent and Trademark Office*